United States Patent [19]

Snitman et al.

[11] Patent Number: 4,537,904

[45] Date of Patent: Aug. 27, 1985

[54] COMPOSITIONS OF 7-OXABICYCLOHEPTANE AND 7-OXABICYCLOHEPTENE COMPOUNDS AND A METHOD FOR THEIR USE IN INHIBITING BRONCHOCONSTRICTION

[75] Inventors: David L. Snitman, Boulder, Colo.; Martin F. Haslanger, Lambertville; Peter W. Sprague, Pennington, both of N.J.

[73] Assignee: E. R. Squibb & Sons, Inc., Princeton, N.J.

[21] Appl. No.: 518,227

[22] Filed: Jul. 28, 1983

Related U.S. Application Data

[60] Division of Ser. No. 378,547, May 17, 1982, , which is a continuation-in-part of Ser. No. 319,511, Nov. 9, 1981, abandoned.

[51] Int. Cl.$^3$ ...................... A61K 31/34; A61K 31/41
[52] U.S. Cl. ..................... 514/469; 514/382
[58] Field of Search ............... 549/463; 424/278, 269; 548/252

[56] References Cited

U.S. PATENT DOCUMENTS

| | | | |
|---|---|---|---|
| 4,143,054 | 5/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,351,949 | 9/1982 | Larock | 548/359 X |
| 4,436,934 | 5/1984 | Larock | 564/188 X |

Primary Examiner—Glennon H. Hollrah
Assistant Examiner—D. B. Springer
Attorney, Agent, or Firm—Lawrence S. Levinson; Burton Rodney

[57] ABSTRACT

7-Oxabicycloheptane and 7-oxabicycloheptene prostaglandin analogs are provided having the structural formula

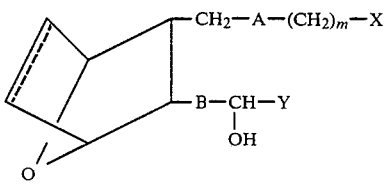

and including all stereoisomers thereof.

The compounds are cardiovascular agents useful, for example, in the treatment of thrombolytic disease.

20 Claims, No Drawings

COMPOSITIONS OF 7-OXABICYCLOHEPTANE AND 7-OXABICYCLOHEPTENE COMPOUNDS AND A METHOD FOR THEIR USE IN INHIBITING BRONCHOCONSTRICTION

This is a division of application Ser. No. 378,547, filed May 17, 1982, which is a continuation-in-part of application Ser. No. 319,511, filed Nov. 9, 1981, abandoned.

DESCRIPTION OF THE INVENTION

The present invention relates to 7-oxabicycloheptane and 7-oxabicycloheptene prostaglandin analogs which are cardiovascular agents useful, for example, in the treatment of thrombolytic disease. These compounds have the structural formula

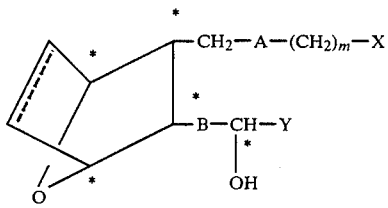

I and including all stereoisomers thereof, wherein
A and B may be the same or different and A is $CH=CH$ or $(CH_2)_2$; B is $CH=CH$, $C\equiv C$ or $(CH_2)_2$; m is 1 to 8;
X is OH;

$$-C\underset{\underset{H}{N-N}}{\overset{N=N}{\diagdown}}$$

;

$CO_2R^1$ wherein $R^1$ is H or lower alkyl; or $$\overset{O}{\underset{}{\|}}$$
$CNH-Z$ wherein Z is H, lower alkyl, aryl, $SO_2$—Q (with Q being lower alkyl or aryl), $$\overset{O}{\underset{}{\|}}$$
$C-Q$, or $OR^2$ wherein $R^2$ is H, and
Y is alkyl (where at least one of A and B is other than $CH=CH$ and X is other than $CO_2R^1$); substituted alkyl; aryl-lower alkyl; alkenyl; alkynyl, aryl; pyridyl; substituted pyridyl; pyridyl-lower alkyl; thienyl, substituted thienyl; thienyl-lower alkyl; cycloalkyl; cycloalkylalkyl; substituted cycloalkylalkyl; or phenoxymethyl and  represents a single bond or a double bond.

In the case where  is a double bond, A must be $CH=CH$ and B may be $CH=CH$ or $(CH_2)_2$; and Y is other than alkenyl and alkynyl.

Thus, the formula I compounds of the invention include the following:

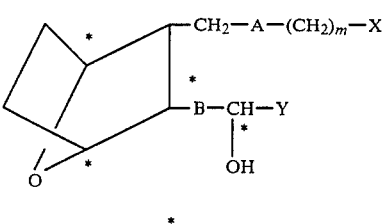

II

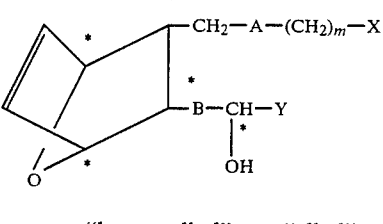

III

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "substituted pyridyl" refers to a pyridyl group substituted with one or two halogen or lower alkyl groups.

The term "substituted thienyl" refers to a thienyl group substituted with one or two halogen or lower alkyl groups.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogen, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The terms "aralkyl", "aryl-alkyl" or "aryl-lower alkyl" as used herein refer to lower alkyl groups as discussed above having an aryl substituent, such as benzyl.

The term "lower alkoxy" or "alkoxy" includes any of the above lower alkyl or alkyl groups linked to an oxygen atom.

The term "lower alkenyl" or "alkenyl" refers to an unsaturated hydrocarbon group having from 3 to 6 carbon atoms and a single carbon-carbon double bond. Typical lower alkenyl groups include, for example, 2-propenyl, 1-propenyl, 1-butenyl, 2-butenyl, 3-butenyl and the like.

The term "lower alkynyl" or "alkynyl" refers to an unsaturated hydrocarbon group having from 3 to 6 carbon atoms, and a single carbon-carbon triple bond. Typical alkynyl groups include, for example, 1-propynyl, 1-butynyl, 2-propynyl, 2-butynyl, 3-butynyl and the like. The term "halogen" or "halo" as used herein refers to chlorine, bromide, fluorine or iodine with fluorine being preferred. The term "$(CH_2)_m$" includes a straight or branched chain radical having from 1 to 8 carbons in the normal chain and may contain one or more lower alkyl substituents. Examples of $(CH_2)_m$ groups include $CH_2$, $CH_2CH_2$, $(CH_2)_3$, $(CH_2)_4$, $(CH_2)_5$, $(CH_2)_6$, $(CH_2)_7$,

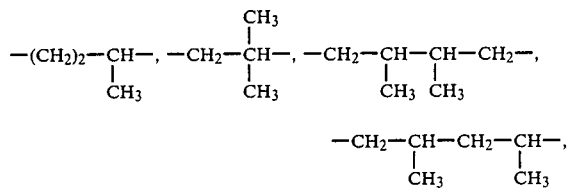

and the like.

Preferred are those compounds of formula II wherein A is $(CH_2)_2$ or $CH=CH$, m is 2 to 4, X is $CO_2H$ $CO_2$-lower alkyl, or

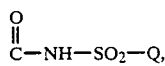

B is $(CH_2)_2$ or $CH=CH$, and Y is $(CH_2)_nCH_3$ (n is 2 to 4), $CH_2C_6H_5$,

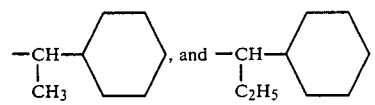

alkyl, cycloalkyl, especially cyclohexyl, 1-methylcyclohexyl, cycloalkylalkyl,

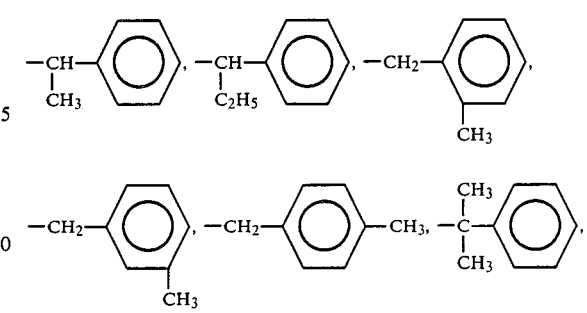

The various compounds of the invention may be prepared as outlined below.

Compounds of formula II wherein X is $CO_2R^1$, A is $(CH_2)_2$ or $—CH=CH—$ and B is $(CH_2)_2$ or $—CH=CH—$ may be prepared according to the following reaction sequence.

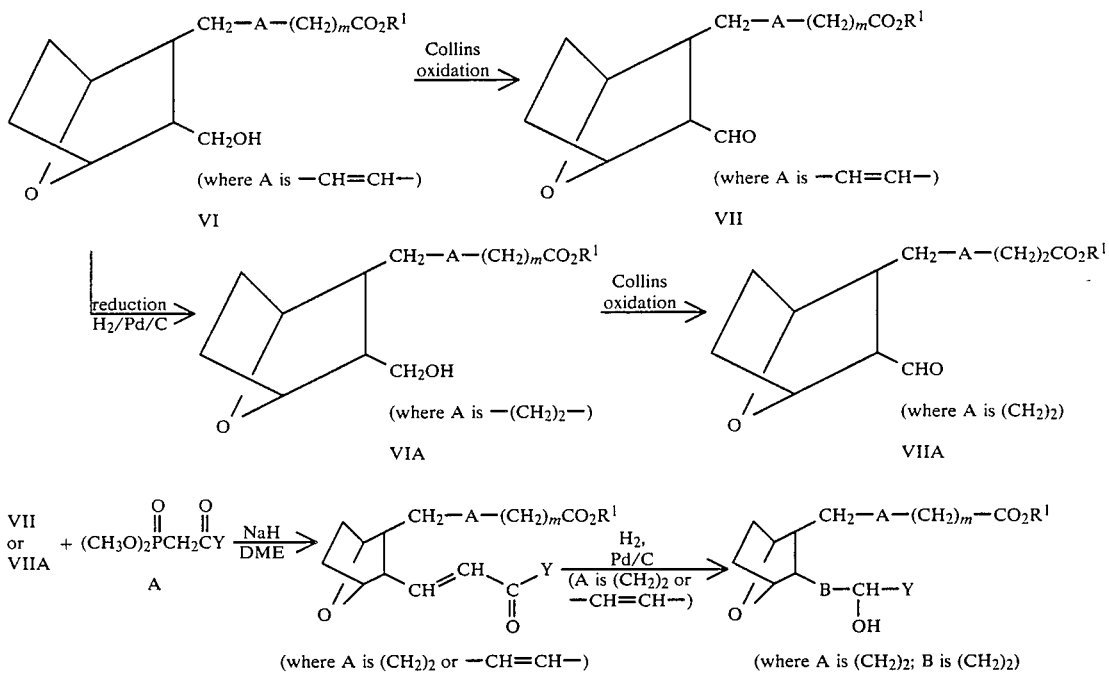

-continued (1) NaAl(OCH₂CH₂OCH₃)₂H, CuBr
(2) NaBH₄

(A is —CH=CH—)

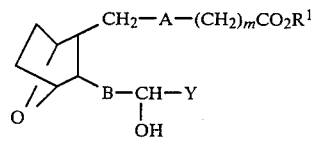

(where A is CH=CH; B is (CH₂)₂

IXB (R¹ is a lower alkyl group throughout)

NaBH₄—CeCl₃

(A) is (CH₂)₂ or —CH=CH—
B is —CH=CH—)

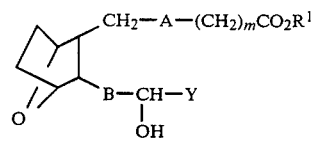

(where A is (CH₂)₂ or —CH=CH—;
B is —CH=CH—)

IXC

The starting lower alkyl ester containing the hydroxymethyl group (that is, compound VI) (prepared as described in U.S. Pat. No. 4,143,054) is used to form the aldehyde VII (where A is —CH=CH—) or VIIA (where A is —(CH₂)₂). Thus, to form aldehyde VII where A is —CH=CH—, compound VI is subjected to a Collins oxidation, for example, by reacting VI with chromium oxide in pyridine. To form the aldehyde VIIA (where A is (CH₂)₂), compound VI is reduced, for example with hydrogen over a palladium on carbon catalyst, to form hydroxymethyl compound VIA (where A is (CH₂)₂) and compound VIA is subjected to a Collins oxidation to form aldehyde VIIA (where A is (CH₂)₂).

Aldehyde VII or VIIA of the structure

VII (A is —CH=CH—) or VIIA (A is CH₂)₂)

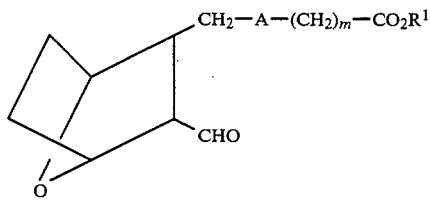

wherein R¹ is lower alkyl is reacted with a dialkoxy phosphonate, such as of the structure

employing a molar ratio of VII or VIIA:A of within the range of from about 1:1 to about 0.5:1, under basic conditions, such as in the presence of sodium hydride or lithium diisopropylamide and an inert organic solvent, such as dimethoxyethane (DME), ether, tetrahydrofuran or toluene to form a compound of the structure

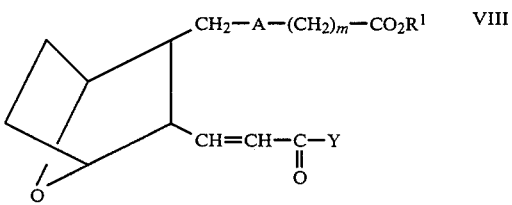

(where A is (CH₂)₂ or —CH=CH—).

Compound VIII may then be reduced in any of the three ways as outlined above to form compounds IXA, IXB or IXC.

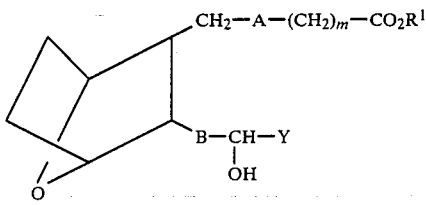

IXA—A is $(CH_2)_2$, B is $(CH_2)_2$
IXB—A is —CH=CH—, B is $(CH_2)_2$
IXC—A is $(CH_2)_2$ or —CH=CH—, B is —CH=CH—

The esters IXA, IXB or IXC can be converted to the free acid, that is, to

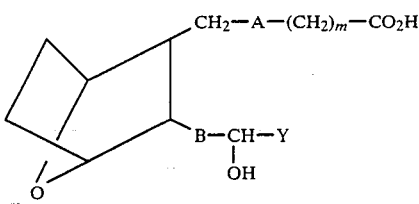

IIA—A is $(CH_2)_2$, B is $(CH_2)_2$
IIB—A is —CH=CH—, B is $(CH_2)_2$
IIC—A is $(CH_2)_2$ or —CH=CH—, B is —CH=CH— by treating the ester IXA, IXB or IXC with a base, such as lithium hydroxide, followed by neutralization with an acid, such as dilute hydrochloric acid or oxalic acid.

Compounds of formula II wherein X is

and Z is

may be prepared by reacting any of the acids IIA, IIB or IIC with p-nitrophenol, in the presence of a coupling agent, such as N,N'-dicyclohexylcarbodiimide, to generate an activated p-nitrophenyl ester which is then reacted with an alkali metal amide

   X such as sodium acetamide (prepared by reaction of sodium hydride and acetamide) employing a molar ratio of II:X of within the range of from about 1:1 to about 0.2:1

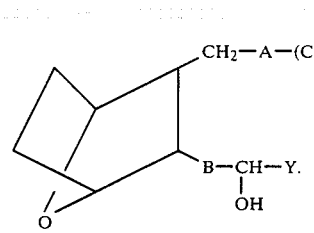   XI

Compounds of formula II wherein X is

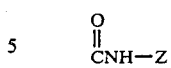

and Z is $SO_2$—Q may be prepared by reacting ester IX with a silyl protecting compound preferably having the structure

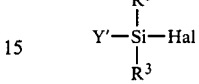   B wherein $R^3$ is lower alkyl or aryl, Y' can be lower alkyl or aryl, preferably t-butyl, and Hal is Cl or Br, such as t-butyldimethylsilyl chloride, employing a molar ratio of IX:B of within the range of from about 0.9:1 to about 0.3:1, in the presence of an inert solvent, such as dimethylformamide, acetonitrile, or dimethylacetamide, and a weak organic base such as imidazole, triethylamine or 4-(N,N-dimethylamino)pyridine, to form the protected silyl ester XII

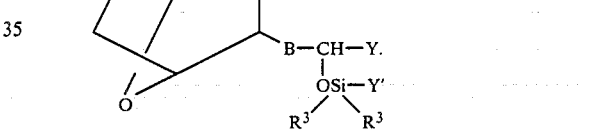   XII

The ester XII is converted to the corresponding acid XIII

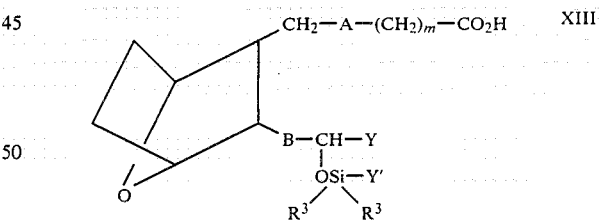   XIII by treating ester XII with a base, such as lithium hydroxide, followed by neutralization with an acid, such as oxalic acid or dilute hydrochloric acid.

The protected acid XIII is then reacted with a sulfonyl isocyanate

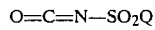   XIV employing a molar ratio of XIII:XIV of within the range of from about 1:1 to about 0.2:1, in the presence of an inert organic solvent, such as tetrahydrofuran, and an organic base, such as triethylamine, to form XV

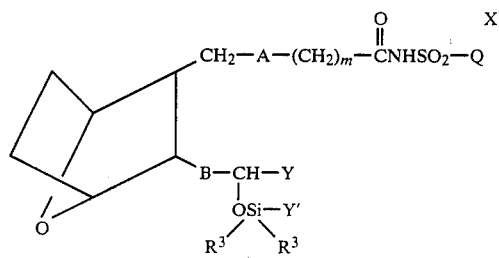
XV

Compound XV is treated to remove the silyl protecting group by treating XV with tetrabutyl ammonium fluoride to form the compound of the invention

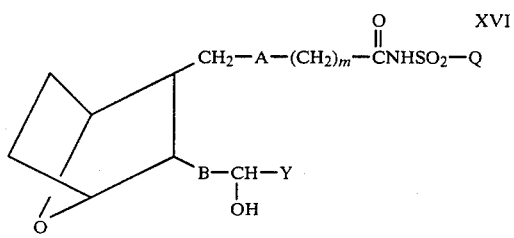
XVI

Compounds of formula II wherein X is

and Z is H, may be prepared by converting an acid of formula IIA, IIB or IIC, that is

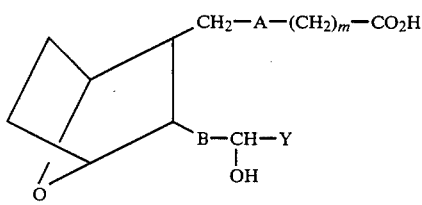

to the corresponding p-nitrophenol ester

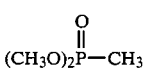
XVII by reacting the acid compound IIA, IIB or IIC with p-nitrophenol (PNP)(employing a molar ratio of acid:PNP of within the range of from about 1:1 to about 0.2:1) in the presence of catalytic amounts of a base, such as 4-dimethylaminopyridine and an equivalent amount of a coupling reagent, such as dicyclohexylcarbodiimide (DCC) and an inert solvent such as tetrahydrofuran. The p-nitrophenol ester XVII is then reacted with ammonia to form the amide XVIII

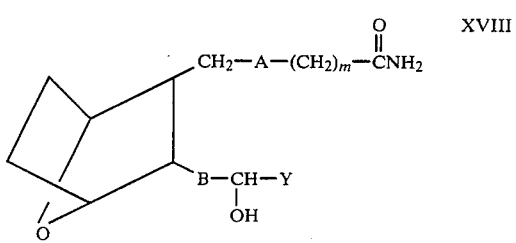
XVIII

Compounds of formula II wherein X is $$\overset{O}{\underset{\|}{C}}NH-Z$$

wherein Z is lower alkyl or aryl may be prepared by reacting the p-nitrophenol ester XVII with an alkylamine or arylamine employing a molar ratio of XVII:amine of within the range of from about 1:1 to about 0.1:1 to form

XIX (wherein Z' is alkyl or aryl).

The dialkoxy phosphonate VII may be prepared by reacting an acetate ester of the structure $$CH_3O\overset{O}{\underset{\|}{C}}-Y \qquad \underline{C}$$

with a phosphonate $$(CH_3O)_2\overset{O}{\underset{\|}{P}}-CH_3 \qquad \underline{D}$$

in the presence of n-butyl lithium employing a molar ratio of C:D of within the range of from about 1:1 to about 0.2:1.

Compounds of formula II wherein X is

and Z is OH may be prepared by reacting an ester of structure IXA, IXB or IXC with hydroxylamine in the presence of a strong base, such as potassium hydroxide, in an inert solvent, such as methanol and thereafter neutralizing with, for example, glacial acetic acid to form a compound of the structure

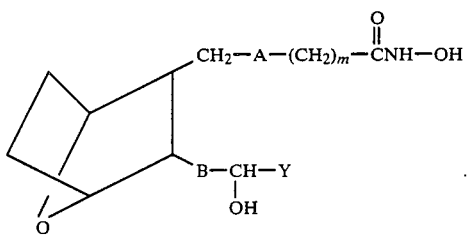
XX

Compounds of formula II wherein X is OH may be prepared by subjecting an ester of formula IXA, IXB or IXC to a lithium aluminum hydride reduction in the presence of an inert solvent, such as tetrahydrofuran, to form a corresponding compound of the structure

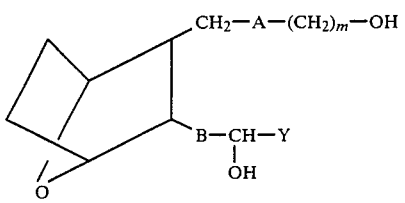
XXI (wherein A and B are as in IXA, IXB and IXC). Compounds of formula II wherein X is tetrazole

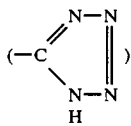

may be prepared by reacting a compound of the formula

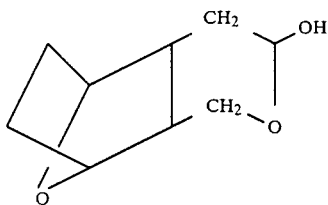
E prepared as described in U.S. Pat. No. 4,143,054 with a Wittig reagent of the structure

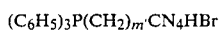
F (wherein m' is 1 to 8)
in the presence of a base, such as potassium t-butoxide or sodium hydride-dimethylsulfoxide, employing a molar ratio of E:F of within the range of from about 1:1 to about 0.2:1, to form a compound of the structure XXII

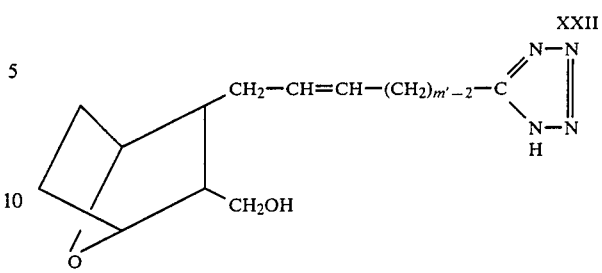
XXII which is subjected to a Collins oxidation to form

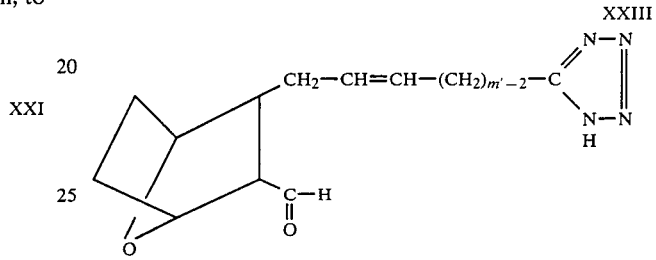
XXIII

The formula XXIII aldehyde is then reacted with a dialkoxy phosphonate of structure A, as described hereinbefore with respect to the preparation of aldehyde VII or VIIA, to form a compound of the structure

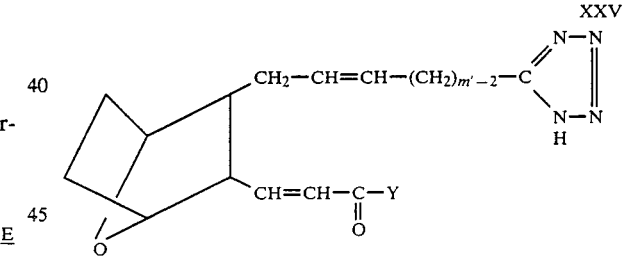
XXV which is then reduced as described hereinbefore to the product XXVI

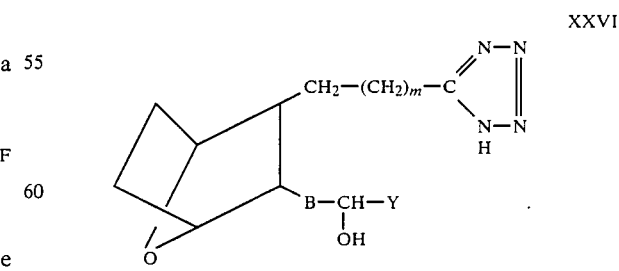
XXVI

The Wittig reagent F may be prepared according to the procedure outlined in *J. Med. Chem.* 22, 1341 (1979), page 1343 and the following reaction sequence:

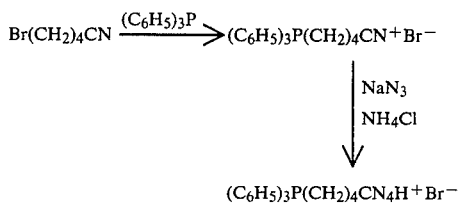

Compounds of formula II wherein B is —C≡C— and A is (CH₂)₂ or —CH=CH— may be prepared by reacting the aldehyde VIIA

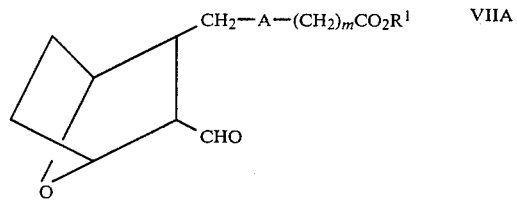

(wherein A is (CH₂)₂ or —CH=CH—) with a phosphonate G

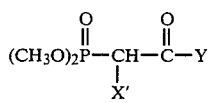

(wherein X' is Cl or Br, prepared as described in U.S. Pat. No. 4,169,145) employing a molar ratio of VIIA:G of within the range of from about 1:1 to about 0.2:1 in the presence of potassium t-butoxide in tetrahydrofuran or sodium hydride in dimethylsulfoxide. The resulting phosphonate product, an α-haloenone (which is a mixture of E and Z isomers) is then subjected to a base such as potassium t-butoxide in tetrahydrofuran to form

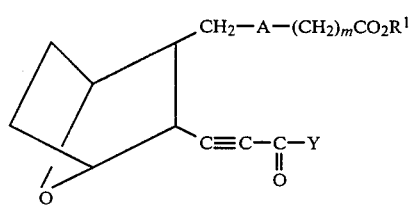

A = —(CH₂)₂— or —CH=CH—

A=—(CH₂)₂— or —CH=CH—
The ynone XXVIII is then reduced with NaBH₄-CeCl₃ to afford II. A similar technique is described in U.S. Pat. No. 4,169,145, Example 23 and is described in Il. Farmaco-Ed.Sc.O Vol. 31-fasc. 10, pp. 763-766 (1975) in the paper entitled "α-Halo-α,β-unsaturated ketones: a synthetic approach to 13-dehydroprostaglandins" by C. Gandolfi and coworkers.

Other compounds wherein B is —C≡C— may be prepared by following procedures outlined above for the preparation of compounds XI, XVI, XVII, XVIII, XIX, XX, XXI, XXVI and XXVII.

Compounds within the scope of formula V, that is

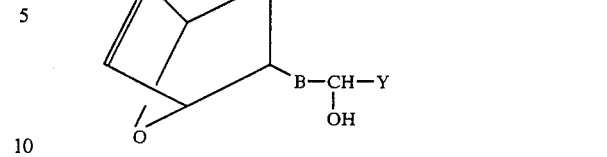

(wherein A is CH=CH and X is CO₂R¹) may be prepared starting with the unsaturated diacid compound

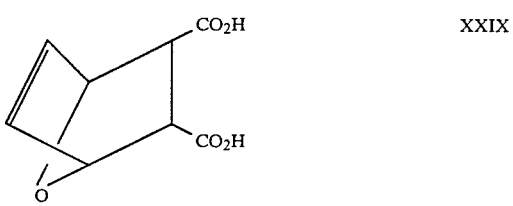

(which is prepared as described in U.S. Pat. No. 4,143,054) which is used to prepare

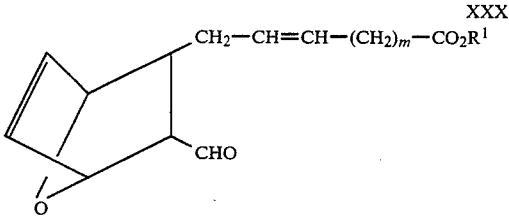

as described in U.S. Pat. No. 4,143,054. Compound XXX may then be used to prepare compound VA employing the procedures as outlined hereinbefore for the preparation of compounds XXB and XXC. Other unsaturated compounds wherein X is other than CO₂R¹ may be prepared following the procedure outlined above for the preparation of compounds XI, XVI, XVII, XVIII, XIX, XX, XXI, XXVI and XXVII, wherein A is —CH=CH— in all cases.

The compounds of this invention have five centers of asymmetry as indicated by the asterisks in formulas I, II and III. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

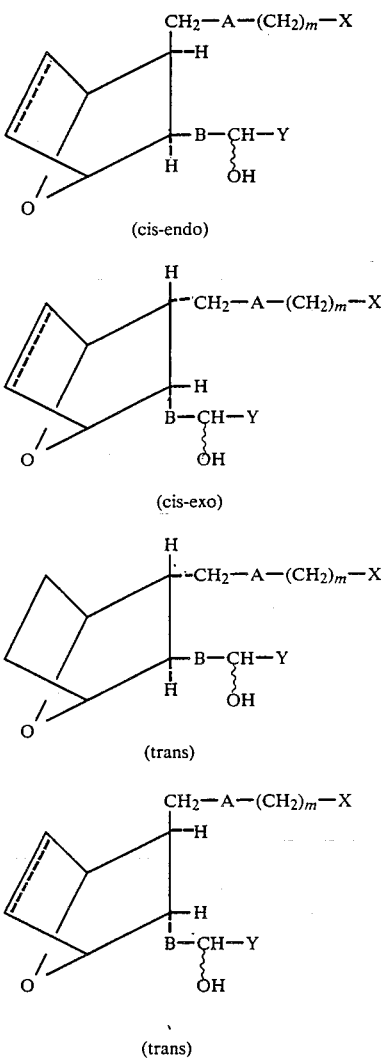

(cis-endo)

(cis-exo)

(trans)

(trans)

The wavy lines (⌇) in the above formulae indicate that the hydroxy group in each of formulae Ia, Ib, Ic and Id is either R($\beta$) or S($\alpha$).

The nucleus in each of the compounds of the invention is depicted as

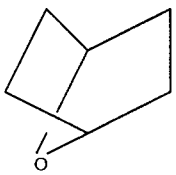

for matter of convenience; it will also be appreciated that the nucleus in the compounds of the invention may be depicted as

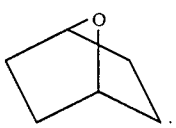

The compounds of this invention are cardiovascular agents useful as platelet aggregation inhibitors, such as in inhibiting arachidonic acid-induced platelet aggregation e.g., for treatment of thrombolytic disease, such as coronary or cerebral thromboses. In addition, the compounds of the invention are useful in inhibiting bronchoconstriction. They are also selective thromboxane $A_2$ synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 gm/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of this invention.

EXAMPLE 1

[1$\beta$,2$\beta$(5Z),3$\alpha$(1E,3S*),4$\beta$]-7-[3-(3-Cyclohexyl-3-hydroxy-1-propenyl)-7-oxabicyclo[2.2.1]hept-2-yl]-5-heptenoic acid A. [1$\beta$,2$\beta$(5Z),3$\alpha$,4$\beta$]-7-[3-Formyl-7-oxabicyclo[2.2.1]hept-2-yl]-5-heptenoic acid, methyl ester A solution of pyridine (8.7 ml) in dichloromethane (200 ml) was treated portionwise with chromium trioxide (5.38 g) with vigorous stirring. After addition was complete, the mixture was stirred at room temperature for 20 minutes then treated with celite (8 g) then [1$\beta$,2$\beta$(5Z),3$\beta$,4$\beta$]-7-[3-(hydroxymethyl)-7-oxabicyclo[2.2.1]hept-2-yl]-5-heptenoic acid, methyl ester prepared as described in U.S. Pat. No. 4,143,054 (2.58 g, 0.0096 moles) in dichloromethane (10 ml). The reaction mixture was stirred at room temperature for 20 minutes then filtered through celite. The filtrate was washed with 5% sodium bicarbonate (2×100 ml), 10% hydrochloric acid (2×100 ml) and again with 5% sodium bicarbonate (2×100 ml). The dichloromethane solution was dried over magnesium sulfate and concentrated in vacuo. The residue was chromatographed on silicar CC-7 (200 ml) eluting with 1) dichloromethane and 2) diethyl ether to yield 2 g of aldehyde. NMR (C-13 & proton) indicated the product to be a mixture of isomers (90% cis-endo and 10% trans-aldehyde). Drying in vacuo at room temperature for any extended period of time caused decomposition as evidenced by thin layer chromatography. TLC: silica gel; benzene/EtOAc (4:1) $R_f$=0.5; visualized with vanillin spray and heat.

B. [1$\beta$,2$\beta$(5Z),3$\alpha$(1E),4$\beta$]-7-[3-(3-Oxo-3-cyclohexyl-1-propenyl)-7-oxabicyclo[2.2.1]hept-2-yl]-5-heptenoic acid, methyl ester To a slurry of 180 mg of 50% sodium hydride (3.75 mmole, 1.44 equivalents) in 60 ml of anhydrous dimethoxyethane (DME) was added 870 mg of 2-oxo-2-cyclohexylethyldimethylphosphonate (3.75 mmole, 1.44 equivalents) in 10 ml of dimethoxyethane at 0° C.

under an argon atmosphere. The mixture was stirred at 25° C. for 1.5 hours. To this solution at 25° C. was added 700 mg of [1β,2β(5Z),3α,4β)]-7-[3-formyl-7-oxabicyclo[2.2.1]-hept-2-yl]-5-heptenoic acid, methyl ester (title A compound) (2.6 mmol) in 10 ml of dimethoxyethane. After 1 hour, the reaction was quenched with 0.5 ml of glacial acetic acid, concentrated, dissolved in 200 ml of ether and washed with 150 ml of 5% potassium bicarbonate and dried over anhydrous magnesium sulfate and concentrated. The residue was purified by flash chromatography on LP-1 silica gel, eluting with 3:7 ether/hexane to provide 515 mg (52% yield) of the title B compound.

$C_1$.  [1β,2β(5Z),3α(1E,3S*),4β]-7-[3-(3-Cyclohexyl-3-hydroxy-1-propenyl)-7-oxabicyclo[2.2.1]hept-2-yl]-5-heptenoic acid, methyl ester and $C_2$.  [1β,2β(5Z),3α(1E,3R*),4β]-7-[3-(3-Cyclohexyl-3-hydroxy-1-propenyl)-7-oxabicyclo[2.2.1]hept-2-yl]-5-heptenoic acid, methyl ester To a solution of 515 mg of the title B compound (1.38 mmole) in 15 ml of dry methanol was added at 25° C. under an argon atmosphere 513 mg of cerium chloride heptahydrate (1.38 mmole, 1 equivalent). The reaction was stirred for 10 minutes, cooled to 0° C. and 53.2 mg of sodium borohydride (1.38 mmole, 4 equivalents) was added. After stirring for 20 minutes at 0° C. the reaction was quenched with 1 ml of acetone, concentrated under high vacuum, diluted with 100 ml of ethyl acetate and washed with 100 ml of brine. The aqueous layer was reextracted with 100 ml of ethyl acetate. The combined organic layers were dried over anhydrous magnesium sulfate and concentrated. The residue was purified by flash chromatography on LP-1 silica gel column, eluting with 1:4 EtOAc-hexane to give 210 mg of the title $C_1$ compound and 191 mg of the title $C_2$ compound.

D.  [1β,2β(5Z),3α(1E,3S*),4β]-7-[3-(3-Cyclohexyl-3-hydroxy-1-propenyl)-7-oxabicyclo[2.2.1]hept-2-yl]-5-heptenoic acid 200 mg of the title $C_1$ alcohol ester (0.53 mmole) was dissolved in 30 ml of an 80% tetrahydrofuran-water solution, chilled to 0° C. and 5.3 ml of a 1 N lithium hydroxide solution was added dropwise. The reaction mixture was stirred at 0° C., then slowly warmed up to 25° C. and stirred for 18 hours. The THF was evaporated under high vacuum and the residue was diluted with 10 ml of water, acidified to pH 3 with a 10% aqueous oxalic acid solution, extracted with three 60 ml portions of ether and 50 ml of brine. The product was dried over anhydrous magnesium sulfate and concentrated to give an oil.

This oil was purified on CC7 silica gel, eluting with a gradient of distilled pentane/ether and filtered through a polycarbonate memberane. The solvents were evaporated under high vacuum for 10 days to give 165 mg of the title compound (86%).

TLC:silica gel; EtOAc/hexane (4:1 $R_f$~0.58).

Analysis calc'd for C, 72.89; H, 9.45. Found: C, 72.68; H, 9.15.

EXAMPLE 2

[1β,2β(5Z),3α(1E,3R*),4β]-7-[3-(3-Cyclohexyl-3-hydroxy-1-propenyl)-7-oxabicyclo[2.2.1]hept-2-yl]-5-heptenoic acid To 166 mg (0.044 mmole) of the $C_2$ alcohol ester (prepared in Example 1) in 30 ml of an 80% tetrahydrofuran (THF)-water solution at 0° C. was slowly added 4.4 ml of a 1 M lithium hydroxide solution. The reaction was stirred at 0° C. and allowed to warm to 25° while stirring for 18 hours. The THF was evaporated and the residue was diluted with 10 ml of water, acidified to pH 3 with a 10% aqueous oxalic acid solution, and extracted with three 60 ml portions of ether and 50 ml of brine. The product was dried over anhydrous magnesium sulfate and concentrated to give an oil. This oil was chromatographed on a CC-7 silica gel column using a pentane-ether gradient, filtered through a polycarbonate membrane, and the solvents were then removed in vacuo to provide 43 mg (27%) of the title compound as an oil.

TLC:silica gel; EtOAc/hexane (4:1) $R_f$=0.38.

Analysis calc'd for: C, 72.89; H, 9.45. Found: C, 72.33, H, 9.36.

Calculated value corrected for 0.16 mole of $H_2O$ per mole of the title slow moving isomer: C, 72.33; H, 9.47.

EXAMPLE 3

[1β,2β(5Z),3α(1E,3S*),4β]-7-[3-(3-Hydroxy-4,4-dimethyl-1-octenyl)-7-oxabicyclo[2.2.1]hept-2-yl]-5-heptenoic acid A.  [1β,2β(5Z),3α(1E),4β]-7-[3-Oxo-4,4-dimethyl-1-octenyl)-7-oxabicyclo[2.2.1]hept-2-yl]-5-heptenoic acid, methyl ester To a slurry of 41.8 mg of 50% sodium hydride in mineral oil (0.87 mmole, 1.1 equivalent) in 60 ml of anhydrous dimethoxyethane (DME) was added 237 mg of 2-oxo-3,3-dimethyl heptyl dimethyl phosphonate (0.95 mmole, 1.2 equiv.) in 10 ml of DME at 0° C. under an argon atomsphere. The mixture was stirred under argon at 25° C. for 1 hour. To this solution at 25° C. was added 212 mg of [1β,2β-(5Z),3α,4β)]-7-[3-formyl-7-oxabicyclo[2.2.1]-hept-2-yl]-5-heptenoic acid, methyl ester prepared as described in Example 1 (0.79 mmole) in 5 ml of DME. After 45 minutes, the reaction was quenched with 0.5 ml of glacial acetic acid, concentrated, dissolved in 150 ml of ether. The ethereal solution was washed with three 40 ml portions of 5% potassium bicarbonate and dried over anhydrous magnesium sulfate and concentrated. The residue was purified by flash chromatography on LP-1 silica gel, eluting with 3:7 ether/hexane to provide 290 mg (93.7%) yield) of the title A compound.

B.  [1β,2β(5Z),3α(1E,3S*),4β]-7-[3-(3-Hydroxy-4,4-dimethyl-1-octenyl)-7-oxabicyclo[2.2.1]hept-2-yl]-5-heptenoic acid, methyl ester and C.  [1β,2β(5Z),3α(1E,3R*),4β]-7-[3-(3-Hydroxy-4,4-dimethyl-1-octenyl)-7-oxabicyclo[2.2.1]hept-2-yl]-5-heptenoic acid, methyl ester To a solution of 1.25 g of the title A compound (3.2 mmole) in 30 ml of dry methanol was added at 25° C. under an argon atomsphere 1.19 g of cerium chloride heptahydrate (3.2 mmole, 1 equivalent). The reaction was stirred for 10 minutes at 25° C., cooled to 0° C. and 123.4 mg of sodium borohydride (3.2 mmole) was slowly added. After stirring for 10 minutes at 0° C., the reaction was poured into 200 ml of saturated ammonium chloride. The mixture was extracted with three 100 ml portions of ether. The ethereal extracts were washed with three 100 ml portions of water and 100 ml of brine. The organic layer was dried over anhydrous magnesium sulfate and concentrated.

The residue was purified by flash chromatography on LP-1 silica gel column, eluting with 1:4 EtOAc/hexane to give 633 mg of the title B compound and 400 mg of the title C compound (83%).

TLC of B: silica gel, hexane/ethyl acetate (2:1) R$_f$~0.51.

TLC of C: R$_f$~0.39.

D. [1β,2β(5Z),3α(1E,3S*),4β]-7-[3-(3-Hydroxy-4,4-dimethyl-1-octenyl)-7-oxabicyclo[2.2.1]hept-2-yl]-5-heptenoic acid 633 mg of alcohol ester the title B compound (1.61 mmole) was dissolved in 90 ml of an 80% tetrahydrofuran-water solution, chilled to 0° C. and 16.1 ml of a 1N lithium hydroxide solution was added dropwise. The reaction mixture was stirred at 0° C., then slowly warmed up to 25° C. and stirred for 15 hours. The THF was evaporated under high vacuum and the residue was diluted with 30 ml of water, acidified to pH 3 with a 10% aqueous oxalic acid solution, and extracted with three 100 ml portions of ether. The organic layer was washed with three 100 ml portions of water and 100 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 4 days to give 429 mg of [1β,2β(5Z),3α(1E,3S*),4β]-7-[3-(3-hydroxy-4,4-dimethyl-1-octenyl)-7-oxabicyclo[2.2.1]hept-2-yl]-5-heptenoic acid (70.6%).

TLC: silica gel; EtOAc/hexane (3:2) R$_f$~0.42.

Analysis calc'd for C, 72.97; H, 10.12. Found: C, 73.02; H, 10.03.

EXAMPLE 4

[1β,2β(5Z),3α(1E,3R*),4β]-7-[3-(3-Hydroxy-4,4-dimethyl-1-octenyl)-7-oxabicyclo[2.2.1]hept-2-yl]-5-heptenoic acid To 285 mg (0.73 mmole) of the title C alcohol ester (prepared in Example 3) in 40 ml of an 80% tetrahydrofuran-water solution at 0° C. was slowly added 7.4 ml of a 1M lithium hydroxide solution. The reaction was stirred at 0° C. and allowed to warm to 25° C. while stirring for 15 hours. The THF was evaporated and the residue was diluted with 20 ml of water, acidified to pH 3 with a 10% aqueous oxalic acid solution, and extracted with three 100 ml portions of ether and 100 ml of brine. The product was dried over anhydrous magnesium sulfate and concentrated to give an oil.

This oil was purified on a CC-7 silica gel column, eluting with a gradient of distilled pentane/ether, filtered through a polycarbonate membrane, and the solvents were evaporated under high vacuum for 4 days to give 248 mg (89.8%) of the title compound as an oil.

TLC: silica gel; EtOAc/hexane (3:2) R$_f$~0.31.

Analysis calc'd for C, 72.97; H, 10.12. Found: C, 72.96; H, 9.84.

EXAMPLE 5

[1β,2β,3α(1E,3S*),4β]-7-[3-(3-Hydroxy-1-octenyl)-7-oxabicyclo[2.2.1]hept-2-yl]heptanoic acid A. [1β,2β,3β,4β]-7-[3-(Hydroxymethyl)-7-oxabicyclo[2.2.1]hept-2-yl]-heptanoic acid, methyl ester To 800 mg (3.0 mmole) of the [1β,2β(5Z),3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 400 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. (1β,2β,3β,4β)-7-[3-Formyl-7-oxabicyclo[2.2.1]hept-2-yl]heptanoic acid, methyl ester To 1.21 g (5.6 mmole, 2.0 equiv.) of pyridinium-chlorochromate (PCC) and 20 ml of anhydrous CH$_2$Cl$_2$ was added, under an argon atmosphere, 730 mg (2.8 mmole) of the title A alcohol in 2 ml of CH$_2$Cl$_2$. The reaction was stirred for 2 hours at 25°, diluted with 100 ml of ether, filtered through a pad of florisil, and evaporated to furnish 670 mg (88%) of the title B compound as a white crystalline solid.

C. (1β,2β,3α,4β)-7-[3-Formyl-7-oxabicyclo[2.2.1]hept-2-yl]heptanoic acid, methyl ester To 800.0 mg of the title B aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine dried over anhydrous magnesium sulfate and concentrated to afford 765.0 mg (98%) of the title C aldehyde.

D. [1β,2β,3α(1E),4β]-7-[3-(3-Oxo-1-octenyl)-7-oxabicyclo[2.2.1]hept-2-yl]heptanoic acid, methyl ester To a slurry of 149.2 mg of 50% sodium hydride (3.1 mmole, 1.1 equivalents) in 50 ml of anhydrous dimethyloxyethane (DME) was added 697 mg (3.1 mmole, 1.1 equivalents) of dimethyl-2-oxoheptylphosphonate in 10 ml of DME at 0° C. under an argon atmosphere. The mixture was stirred at 25° for 1.5 hours. To this solution at 25° C. was added 765 mg (2.8 mmole) of title C compound in 10 ml of DME. After 3 hours, the reaction was quenched with 0.5 ml of glacial acetic acid, concentrated, dissolved in 150 ml of 5% potassium bicarbonate and dried over anhydrous magnesium sulfate and concentrated. The residue was purified by flash chromatography on LP-1 silica gel, eluting with 1:10 ethyl acetate/hexane solution to provide 654 mg of the title D compound.

E. [1β,2β,3α(1E,3S*),4β]-7-[3-(3-Hydroxy-1-octenyl)-7-oxabicyclo[2.2.1]hept-2-yl]heptanoic acid, methyl ester and F. [1β,2β,3α(1E,3R*),4β]-7-[3-(3-Hydroxy-1-octenyl)-7-oxabicyclo[2.2.1]hept-2-yl]heptanoic acid, methyl ester To 654 mg (1.9 mmole) of title D compound in 40 ml of anhydrous methanol at 0° C. was added 708 mg (1.9 mmole, 1 equivalent) of cerium chloride heptahydrate. The reaction was stirred for 10 minutes and 72 mg (1.9 mmole) of sodium borohydride was added. After stirring for 20 minutes at 0° C., the reaction was poured into 50 ml of saturated ammonium chloride and extracted with three 100 ml portions of ethyl acetate, washed successively with 50 ml of water and 50 ml of brine, and dried over anhydrous magnesium sulfate to provide, following purification by flash chromatography on a LP-1 silica gel, eluting with 1:10 ethyl acetate/hexane, 292 mg of the title E compound and 300 mg of the title F compound.

G. [1β,2β,3α(1E,3S*),4β]-7-[3-(3-Hydroxy-1-octenyl)-7-oxabicyclo[2.2.1]hept-2-yl]heptanoic acid To 292 mg (1.1 mmole) of the title F ester in 30 ml of an 80% THF-H$_2$O solution at 0°, under an argon atmosphere, was slowly added 8.5 ml of a 1M LiOH solution. The reaction was stirred for 4 hours at 25°, acidified to pH 3 with a saturated aqueous oxalic acid solution and diluted with 70 ml of water. This aqueous solution was extracted with three 100 ml portions of ether. The combined ethereal layers were washed with 50 ml of water and 50 ml of brine, dried over anhydrous MgSO₄ and the solvent was removed to afford a light yellow oil. This oil was diluted with freshly distilled ether and filtered through a plug of Silicar CC-7 and a polycarbonate membrane to furnish 288 mg (99%) of the title compound as an off-white crystalline solid: m.p. 64.0°–64.5°.

Analysis Calc'c for $C_{21}H_{36}O_4$: C, 71.55; H, 10.29. Found: C, 70.70; H, 9.98.

Calculated value corrected to 0.23 mole of water per mole of the title compound: C, 70.70; H, 10.30.

EXAMPLE 6

[1β,2β,3α(1E,3R*),4β]-7-[3-(3-Hydroxy-1-octenyl)-7-oxabicyclo[2.2.1]hept-2-yl-heptanoic acid To 192 mg (0.72 mmole) of the title E ester (prepared as described in Example 5, part E), in 20 ml of an 80% THF-H₂O solution at 0° under an argon atmosphere, was slowly added 5.5 ml of a 1M LiOH solution. The reaction was stirred for 4 hours at 25°, acidified to pH 3 with a saturated aqueous oxalic acid solution, and diluted with 70 ml of water. This aqueous solution was extracted with three 100 ml portions of ether. The combined ethereal layers were washed with 50 ml of water and 50 ml of brine, dried over anhydrous MgSO₄, and the solvent was removed to afford a light yellow oil. This oil was diluted with freshly distilled ether and filtered through a plug of Silicar CC-7 and a polycarbonate membrane to afford 190 mg of the title compound as a light yellow oil.

EXAMPLE 7

[1β,2β,3α(3S*),4β]-7-[3-(3-Hydroxy-1-octyl)-7-oxabicyclo[2.2.1]hept-2-yl]-heptanoic acid A. [1β,2β,3α(3S*),4β]-7-[3-(3-Hydroxy-1-octyl)-7-oxabicyclo[2.2.1]hept-2-yl]-heptanoic acid, methyl ester To 98.0 mg (0.28 mmole) of the acid product of Example 5 (prepared as described in Example 5, part G) in 3 ml of anhydrous methanol was added 50 mg of 5% Rh-Al₂O₃ and stirred under an atmospheric pressure of hydrogen for 24 hours. The crude product was filtered through a Celite plug, concentrated, esterified with an ethereal solution of diazomethane, and flash chromatographed on a 1×8" LP-1 silica gel column using 10% EtOAc in hexane as the eluent to provide 43.8 mg (44%) of the title A compound as a clear colorless oil.

B. [1β,2β,3α(3S*),4β]-7-[3-(3-Hydroxy-1-octyl)-7-oxabicyclo[2.2.1]hept-2-yl]-heptanoic acid To 43.8 mg (0.12 mmole) of the title A ester in 10 ml of 80% THF in water at 0° under an argon atmosphere was added 2 ml of a 1M LiOH solution and stirred for 5 hours at 25°. The reaction was acidified to pH 3 with a saturated aqueous oxalic acid solution, diluted with 25 ml of water and extracted with three 50 ml portions of ether. The combined ethereal layers were washed with 50 ml of water and 50 ml of brine, dried over anhydrous magnesium sulfate, and flash chromatographed on a 1×6" LP-1 silica gel column using a 3% methanol in methylene chloride eluent to provide 21.1 mg (48%) of the title compound as an oil.

Analysis calc'd for $C_{21}H_{38}O_4$: C, 71.14; H, 10.80. Found: C, 70.65; H, 10.54.

Calculated value corrected for 0.14 moles of water per mole of title compound: C, 70.65; H, 10.81.

EXAMPLE 8

[1β,2β,3α(3R*),4β]-7-[3-(3-Hydroxy-1-octyl)-7-oxabicyclo[2.2.1]hept-2-yl]-heptanoic acid To 71.0 mg (0.20 mmole) of [1β,2β,3α(3S*),4β]-7-[3-(3-hydroxy-1-octy)-7-oxabicyclo [2.2.1]hept-2-yl]-heptanoic acid (prepared as described in Example 7) in 5 ml of methanol was added 35 mg of 5% Rh-Al₂O₃ and stirred under an atmospheric pressure of hydrogen for 6 hours. The crude product was filtered through a plug of Silicar CC-7, concentrated and flash chromatographed on a 1×6" LP-1 silica gel column using 3% methanol in methylene chloride to provide 13.3 mg of the title compound as an oil.

Analysis calc'd for $C_{21}H_{38}O_4$: C, 71.14; H, 10.80. Found: C, 70.05; H, 10.46.

Calculated value corrected for 0.31 mole of water per mole of the title compound C, 70.05; H, 10.81.

EXAMPLE 9

[1β,2β(5Z),3α(1E,3S*),4β]-7-[3-(4-Cyclopentyl-3-hydroxy-1-butenyl)-7-oxabicyclo[2.2.1]hept-2-yl]-5-heptenoic acid A. [1β,2β(5Z),3α(1E),4β]-7-[3-(3-Oxo-4-cyclopentyl-1-butenyl)-7-oxabicyclo[2.2.1]hept-2-yl]-5-heptenoic acid, methyl ester To a slurry of 240 mg of 50% sodium hydride in mineral oil (4.76 mmole, 1.1 equivalent) in 60 ml of dimethoxyethane (DME) was added 1.26 g of 2-oxo-3-cyclopentyl propyl dimethylphosphonate (5.41 mmole, 1.2 equivalents) in 10 ml of DME at 0° C. under an argon atmosphere. The mixture was stirred under argon at 25° C. for 1 hour. To this solution at 25° C. was added 1.2 g of [1β,2β-(5Z),3α,4β)]-7-[3-formyl-7-oxabicyclo[2.2.1]-hept-2-yl]-5-heptenoic acid, methyl ester prepared as described in Example 1, part A, (4.53 mmole) in 10 ml of DME. After 1 hour, the reaction was quenched with 1 ml of glacial acetic acid, concentrated, dissolved in 300 ml of ether. The ethereal solution was washed with three 100 ml portions of 5% potassium bicarbonate and 100 ml of brine. The organic layer was dried over anhydrous magnesium sulfate and concentrated to give 1.76 g of crude title A compound. This crude oil was used directly in the next reaction without purification.

B. [1β,2β(5Z),3α(1E,3S*),4β]-7-[3-(4-Cyclopentyl-3-hydroxy-1-butenyl)-7-oxabicyclo[2.2.1]hept-2-yl]-5-heptenoic acid, methyl ester and C. [1β,2β(5Z),3α(1E,3R*),4β]-7-[3-(4-Cyclopentyl-3-hydroxy-1-butenyl)-7-oxabicyclo[2.2.1]hept-2-yl]-5-heptenoic acid, methyl ester To a solution of 1.76 g of crude title A compound in 30 ml of dry methanol was added at 25° C. under an argon atmosphere 1.73 g cerium chloride containing 35% water (4.53 mmole, 1 equiv.). The reaction was stirred for 10 minutes at 25° C., cooled to 0° C. and 175 mg of sodium borohydride (4.53 mmole, 4 equiv.) was slowly added. After stirring for 10 minutes at 0° C., the reaction was poured into 200 ml of saturated ammonium chloride. The mixture was extracted with three 100 ml portions of ether. The ethereal extracts were washed with three 100 ml portions of water and 100 ml of brine. The organic layer was dried over anhydrous magnesium sulfate and concentrated.

The residue was purified and separated on Waters HPLC, eluting with 1:3 EtOAc/hexane to give 276 mg of the title B compound and 225 mg of the title C compound.

TLC of title B: Silica gel; hexane/ethyl acetate (1:1) $R_f \sim 0.50$.

TLC of title C: $R_f \sim 0.45$.

D. [1β,2β(5Z),3α(1E,3S*),4β]-7-[3-(4-Cyclopentyl-3-hydroxy-1-butenyl)-7-oxabicyclo[2.2.1]hept-2-yl]-5-heptenoic acid 161 mg of the title B alcohol ester (0.42 mmole) was dissolved in 20 ml of an 80% tetrahydrofuran-water solution, chilled to 0° C. and 4.2 ml of a 1N lithium hydroxide solution was added dropwise. The reaction was stirred at 0° C., then slowly warmed up to 25° C. while stirring over an 18 hour period. The THF was evaporated under high vacuum and the residue was diluted with 10 ml of water, acidified to pH 3 with a 10% aqueous oxalic acid solution, and extracted with three 50 ml portions of ether. The organic layer was washed with three 50 ml portions of water and 50 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 10 days to give 151 mg of [1β,2β(5Z),3α(1E,3S*),4β]-7-[3-(3-cyclopentyl-3-hydroxy-1-butenyl-7-oxabicyclo[2.2.1-]hept-2-yl]-5-heptenoic acid (99.3%).

TLC: Silica gel; EtOAc/hexane (4:1) $R_f \sim 0.48$.

Analysis: Cal'd for: C, 72.89; H, 9.45. Found: C, 72.59; H, 9.26.

EXAMPLE 10

[1β,2β(5Z),3α(1E,3R*),4β]-7-[3-(4-Cyclopentyl-3-hydroxy-1-butenyl)-7-oxabicyclo[2.2.1]hept-2-yl]-5-heptenoic acid 100 mg of the title C alcohol ester (prepared as described in Example 9), (0.27 mmole) was dissolved in 10 ml of an 80% tetrahydrofuran-water solution, chilled to 0° C. and 2.7 ml of a 1N lithium hydroxide solution was added dropwise. The reaction mixture was stirred at 0° C. then slowly warmed up to 25° C. while stirring over an 18 hour period. The THF was evaporated under high vacuum and the residue was diluted with 10 ml of water, acidified to pH 3 with a 10% aqueous oxalic acid solution, and extracted with three 50 ml portions of ether. The organic layer was washed with three 50 ml portions of water and 50 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 10 days to give 90 mg of the title compound (92.0%).

TLC: Silica gel; EtOAc/hexane (4:1); $R_f \sim 0.38$.

Analysis: Cal'd for: C, 72.89; H, 9.45. Found: C, 72.73; H, 9.70.

EXAMPLE 11

[1β,2β(5Z),3α(1E,3S*),4β]-7-[3-(4-Cyclopentyl-3-hydroxy-1-butenyl)-7-oxabicyclo[2.2.1]hept-2-yl]-5-heptenoic acid, methyl ester The synthesis of the title compound was described in Example 9, part B.

Purification of the title compound was done on a CC-7 silica gel column, eluting with a gradient of distilled pentane/ether, filtered through a polycarbonate membrane. The solvents were evaporated under high vacuum for 12 days.

TLC: Silica gel; EtOAc/hexane (1:1); $R_f \sim 0.50$.

Analysis: Cal'd (includes 0.16 mole of water): C, 72.79; H, 9.64. Found: C, 72.79; H, 9.58.

EXAMPLE 12

[1β,2β(5Z),3α(1E,3R*),4β]-7-[3-(4-Cyclopentyl-3-hydroxy-1-butenyl)-7-oxabicyclo[2.2.1]hept-2-yl]-5-heptenoic acid, methyl ester The synthesis of the title compound was described in Example 9, part C.

Purification of the title compound was done on a CC-7 silica gel column, eluting with a gradient of distilled pentane/ether, filtered through a polycarbonate membrane. The solvents were evaporated under high vacuum for 12 days.

TLC: Silica gel; EtOAc/hexane (1:1); $R_f \sim 0.45$.

Analysis: Cal'd (includes 0.21 mole of water): C, 72.61; H, 9.64. Found: C, 72.61; H, 9.62.

EXAMPLE 13

[1β,2β(5Z),3α(1E,3S*),4β]-7-[3-(3-Hydroxy-4-phenyl-1-butenyl)-7-oxabicyclo[2.2.1]hept-2-yl]-5-heptenoic acid A. [1β,2β(5Z),3α(1E),4β]-7-[3-(3-Oxo-4-phenyl-1-butenyl)-7-oxabicyclo[2.2.1]hept-2-yl]-5-heptenoic acid, methyl ester To 411.6 mg of freshly distilled diisopropylamine in 80 ml of dry toluene at −78° C. was added 2.3 ml of a 1.6M solution of n-butyllithium in hexane (3.71 mmole). The mixture was stirred for 5 minutes, and to this mixture at −78° C. was added 952.5 mg of 2-oxo-3-phenyl-propyldimethylphosphonate (3.91 mmole, 1.1 equivalent). The mixture was warmed up to 25° C. while stirring. To this mixture at 25° C. was added 938 mg of [1β,2β(5Z),3α,4β]-7-[3-formyl-7-oxabicyclo[2.2.1]hept-2-yl]-5-heptenoic acid, methyl ester prepared as described in Example 1, part A (3.55 mmole). After 2.5 hours, the reaction was quenched with 0.5 ml of glacial acetic acid, diluted with 300 ml of ether. The ethereal solution was washed with three 100 ml portions of a 5% sodium bicarbonate solution and 100 ml of brine. The organic layer was dried over anhydrous magnesium sulfate, concentrated to give 1.22 g of a crude oil. This oil was used in the next step without purification.

B. [1β,2β(5Z),3α(1E,3S*),4β]-7-[3-(3-Hydroxyl-4-phenyl-1-butenyl)-7-oxabicyclo[2.2.1]hept-2-yl]-5-heptenoic acid, methyl ester and C. [1β,2β(5Z),3α(1E,3R*),4β]-7-[3-(3-Hydroxyl-4-phenyl-1-butenyl)-7-oxabicyclo[2.2.1]hept-2-yl]-5-heptenoic acid, methyl ester To a solution of 1.22 g of the crude title A compound in 30 ml of dry methanol was added at 25° C. under an argon atmosphere 1.18 g of cerium chloride containing 35% water (2.64 mmole, 1 equiv.). The reaction was stirred for 10 minutes at 25° C., cooled to 0° C. and 119 mg of sodium borohydride (2.64 mmole, 4 equiv.) was slowly added. After stirring for 10 minutes at 0° C., the reaction was poured into 200 ml of saturated ammonium chloride. The mixture was extracted with three 100 ml portions of ether. The ethereal extracts were washed with three 100 ml portions of water and 100 ml of brine.

The organic layer was dried over anhydrous magnesium sulfate and concentrated.

Separation and purification was done on Waters HPLC, eluting with 30% ethyl-acetate in hexane to give 299 mg of the title B compound and 272 mg of the title C compound.

TLC of title B: Silica gel; EtOAc/hexane (1:1); $R_f\sim 0.44$.

TLC of title C: $R_f\sim 0.35$.

D. [1$\beta$,2$\beta$(5Z),3$\alpha$(1E,3S*),4$\beta$]-7-[3-(3-Hydroxy-4-phenyl-1-butenyl)-7-oxabicyclo[2.2.1]hept-2-yl]-5-heptenoic acid 299 mg of the title B alcohol ester (0.78 mmole) was dissolved in 50 ml of an 80% tetrahydrofuran-water solution, chilled to 0° C. and 7.8 ml of a 1N lithium hydroxide solution was added dropwise. The reaction mixture was stirred at 0° C., then slowly warmed up to 25° C. over a 15 hour period. The THF was evaporated under high vacuum and the residue was diluted with 10 ml of water, acidified to pH 3 with a 10% aqueous oxalic acid solution, extracted with three 100 ml portions of ether. The organic layer was washed with three 100 ml portions of water and 100 ml of brine. The product was dried over anhydrous magnesium sulfate and concentrated to give an oil.

This oil was purified on a CC-7 column, eluting with a gradient of distilled pentane/ether and filtered through a polycarbonate membrane. The solvents were evaporated under high vacuum for 12 days to give 131 mg of [1$\beta$,2$\beta$(5Z),3$\alpha$(1E,3S*),4$\beta$]-7-[3-(3-(hydroxy-4-phenyl-1-butenyl)-7-oxabicyclo-[2.2.1]hept-2-yl]-5-heptenoic acid.

Analysis: Calc'd for: C, 74.55; H, 8.16. Found: C, 74.42; H, 8.21.

EXAMPLE 14

[1$\beta$,2$\beta$(5Z),3$\alpha$(1E,3R*),4$\beta$]-7-[3-(3-Hydroxy-4-phenyl-1-butenyl)-7-oxabicyclo[2.2.1]hept-2-yl]-5-heptenoic acid 272 mg of the title C alcohol ester (prepared as described in Example 13) (0.71 mmole) was dissolved in 40 ml of an 80% tetrahydrofuran-water solution, chilled to 0° C. and 7.1 ml of a 1N lithium hydroxide solution was added dropwise. The reaction mixture was stirred at 0° C., then slowly warmed up to 25° C. over a 15 hour period. The THF was evaporated under high vacuum and the residue was diluted with 10 ml of water, acidified to pH 3 with a 10% aqueous oxalic acid solution, extracted with three 100 ml portions of ether. The organic layer was washed with three 100 ml portions of water and 100 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 12 days to give 176 mg of [1$\beta$,2$\beta$(5Z),3$\alpha$(1E,3R*),4$\beta$]-7-[3-(3-hydroxy-4-phenyl-1-butenyl)-7-oxabicyclo[2.2.1]hept-2-yl]-5-heptenoic acid.

Analysis: Calc'd (includes 0.17 moles of water): C, 73.93; H, 8.19. Found: C, 73.93; H, 7.94.

EXAMPLE 15

[1$\beta$,2$\beta$(5Z),3$\alpha$(1E,3S*),4$\beta$]-7-[3-(3-Cyclopentyl-3-hydroxy-1-propenyl)-7-oxabicyclo[2.2.1]hept-2-yl]-5-heptenoic acid A. [1$\beta$,2$\beta$(5Z),3$\alpha$(1E),4$\beta$]-7-[3-(3-Oxo-3-cyclopentyl-1-propenyl)-7-oxabicyclo[2.2.1]hept-2-yl]-5-heptenoic acid To 375.6 mg of freshly distilled diisopropylamine (3.71 mmole, 1.1 equiv.) in 80 ml of dry toluene at $-78°$ C. was added 2.3 ml of a 1.6M solution of n-butyllithium in hexane (3.71 mmole, 1.1 equiv.). The mixture was stirred for 5 minutes, and to this mixture at $-78°$ C. was added 891.7 mg of 2-oxo-2-cyclopentyl ethyl dimethyl phosphonate (4.05 mmole, 1.2 equiv.). The mixture was warmed up to 25° C. while stirring. To this mixture at 25° C. was added 900 mg of [1$\beta$,2$\beta$(5Z),3$\beta$, 4$\alpha$]-7-[3-formyl-7-oxabicyclo[2.2.1]-hept-2-yl]-5-heptenoic acid, methyl ester (prepared as described in Example 1) (3.41 mmole). After 2.5 hours, the reaction was quenched with 0.5 ml of glacial acetic acid, diluted with 300 ml of ether. The ethereal solution was washed with three 100 ml portions of a 5% sodium bicarbonate solution and 100 ml of brine. The organic layer was dried over anhydrous magnesium sulfate, concentrated to give 1.26 g of a crude oil. This oil was used in the next step without purification.

B. [1$\beta$,2$\beta$(5Z),3$\alpha$(1E,3S*),4$\beta$]-7-[3-(3-Hydroxyl-3-cyclopentyl-1-propenyl)-7-oxabicyclo[2.2.1]hept-2-yl]-5-heptenoic acid, methyl ester and C. [1$\beta$,2$\beta$(5Z),3$\alpha$(1E,3R*),4$\beta$]-7-[3-(3-Hydroxyl-3-cyclopentyl-1-propenyl)-7-oxabicyclo[2.2.1]hept-2-yl]-5-heptenoic acid, methyl ester To a solution of 1.25 g of crude title A compound in 30 ml of dry methanol was added at 25° C. under an argon atmosphere 1.29 g of cerium chloride containing 35% water (3.41 mmole, 1 equiv.). The reaction was stirred for 10 minutes at 25° C., cooled to 0° C. and 130 mg of sodium borohydride (3.41 mmole, 4 equiv.) was slowly added. After stirring for 10 minutes at 0° C., the reaction was poured into 200 ml of saturated ammonium chloride. The mixture was extracted with three 100 ml portions of ether. The ethereal extracts were washed with three 100 ml portions of water and 100 ml of brine. The organic layer was dried over anhydrous magnesium sulfate and concentrated.

Separation and purification was done on Waters HPLC, eluting with 30% ethylacetate in hexane to give 426 mg of title B compound and 297 mg of title C compound.

TLC of title B: Silica gel; EtOAc/hexane (1:1); $R_f\sim 0.55$.

TLC of title C: $R_f\sim 0.42$.

D. [1$\beta$,2$\beta$(5Z),3$\alpha$(1E,3S*),4$\beta$]-7-[3-(3-Cyclopentyl-3-hydroxy-1-propenyl)-7-oxabicyclo[2.2.1]hept-2-yl]-5-heptenoic acid 426 mg of title B alcohol ester (1.18 mmole) was dissolved in 50 ml of an 80% tetrahydrofuran-water solution, chilled to 0° C. and 11.8 ml of a 1N lithium hydroxide solution was added dropwise. The reaction mixture was stirred at 0° C., then slowly warmed up to 25° C. over a 15 hour period. The THF was evaporated under high vacuum and the residue was diluted with 10 ml of water, acidified to pH 3 with a 10% aqueous oxalic acid solution, extracted with three 100 ml portions of ether. The organic layer was washed with three 100 ml portions of water and 100 ml of brine. The product was dried over anhydrous magnesium sulfate and concentrated to give an oil.

This oil was purified on a CC-7 column, eluting with a gradient of distilled pentane/ether and filtered through a polycarbonate membrane. The solvents were evaporated under high vacuum for 11 days to give 252 mg of [1β,2β(5Z),3α(1E,3S*),4β]-7-[3-(3-cyclopentyl-3-hydroxy-1-propenyl)-7-oxabicyclo[2.2.1]hept-2-yl]-5-heptenoic acid.

Analysis: Calcd. for: C, 72.39; H, 9.25. Found: C, 72.49, H, 9.29.

EXAMPLE 16

[1β,2β(5Z),3α(1E,3R*),4β]-7-[3-(3-Cyclopentyl-3-hydroxy-1-propenyl)-7-oxabicyclo[2.2.1]hept-2-yl]-5-heptenoic acid 297 mg of the title C alcohol ester (prepared as described in Example 15) (0.82 mmole) was dissolved in 40 ml of an 80% tetrahydrofuran-water solution, chilled to 0° C. and 8.2 ml of a 1N lithium hydroxide solution was added dropwise. The reaction mixture was stirred at 0° C., then slowly warmed up to 25° C. over a 15 hour period. The THF was evaporated under high vacuum and the residue was diluted with 10 ml of water, acidified to pH 3 with a 10% aqueous oxalic acid solution, extracted with three 100 ml portions of ether. The organic layer was washed with three 100 ml portions of water and 100 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 11 days to give 304 mg of the title compound.

Analysis: Calcd. for: C, 72.39; H, 9.25. Found: C, 72.31; H, 9.45.

EXAMPLE 17

[1β,2β(5Z),3α(1E,3S*),4β]-N-Acetyl-7-[3-(3-cyclohexyl-3-hydroxyl-1-propenyl)-7-oxabicyclo[2.2.1]-hept-2-yl]-5-heptenamide To 182.6 mg (0.50 mmole) of [1β,2β(5Z),3α(1E),3S*),4β]-7-[3-(3-cyclohexyl-3-hydroxy-1-propenyl)-7-oxabicyclo[2.2.1]hept-2-yl]-5-heptenoic acid (prepared as described in Example 1) in 3 ml of anhydrous THF was added 76.5 mg (0.55 mmole, 1.1 equiv.) of p-nitrophenol (PNP), ca. 5 mg of 4-dimethylaminopyridine, and 113.3 mg (0.55 mmole, 1.1 equiv.) of N,N'-dicyclohexylcarbodiimide (DCC). The reaction was stirred under an argon atmosphere at 25° for 2 hours, an additional 35.0 mg (0.25 mmole, 0.5 equiv.) of PNP and 52.0 mg (0.25 mmole, 0.5 equiv.) of DCC was added, and the reaction was stirred for 1 hour. This p-nitrophenolic ester solution was added via syringe to a solution of 60 mg of 50% NaH in mineral oil (1.25 mmole, 2.5 equiv.; washed three times with dry pentane), and 92.3 mg (1.25 mmole, 2.5 equiv.) of acetamide in 3 ml of anhydrous THF under an argon atmosphere at 25°, which had been stirred for 3 hours. This bright orange reaction mixture was stirred for 1 hour, and then slowly added to a solution of 50 ml saturated NH4Cl and 5 ml of 2NHCl, extracted with two 50 ml portions of ethyl acetate, washed with 20 ml of water and 20 ml brine, and dried over anhydrous magnesium sulfate. This ethyl acetate solution was cooled to 0° for 18 hours, the PNP crystallized out of solution, filtered and evaporated to provide ca. 200 mg of a crude oil.

Flash chromatography on LP-1 SiO2 (1:1 hexane/EtOAc) followed by preparative thin layer chromatography on a 20×20 cm Whatman 1 mm PKGF silica gel plate using a 1:2 hexane:ethyl acetate eluent provide 39 mg (19%) of [1β,2β(5Z),3α(1E,3S*),4β]-N-acetyl-7-[3-(3-cyclohexyl-3-hydroxyl-1-propenyl)-7-oxabicyclo[2.2.1]-hept-2-yl]-5-heptenamide as a clear colorless oil.

Analysis: Calcd. for C24H37NO4: C, 71.43; H, 9.24; N, 3.47.

Found: C, 71.30; H, 9.31; N, 3.63.

EXAMPLE 18

[1β,2β(5Z),3α(1E,3S*),4β]-7-[3-(3-Cyclohexyl-3-hydroxy-1-propenyl)-7-oxabicyclo[2.2.1]hept-2-yl]-N-(phenylsulfonyl)-5-heptenamide A. [1β,2β(5Z),3α(1E,3S*),4β]-7-[3- Cyclohexyl-3-t-butyldimethylsilyloxy-1-propenyl)-7-oxabicyclo[2.2.1]hept-2-yl]-5-heptenoic acid, methyl ester To 540.8 mg (1.44 mmole) of [1β,2β(5Z),3α(1E,3S*),4β]-7-[3-cyclohexyl-3-hydroxy-1-propenyl)-7-oxabicyclo[2.2.1]hept-2-yl]-5-heptenoic acid, methyl ester (prepared as described in Example 1) in 5 ml of anhydrous DMF under an argon atmosphere at 25° was added 433.5 mg of (2.9 mmole, 2 equiv.) of dimethyl-tert-butylsilylchloride and 392.3 mg (5.76 mmole, 4 equiv.) of imidazole and stirred for 2 hours. The solvents were evaporated, the residual oil was diluted with 150 ml of ether and washed with 25 ml of saturated NH4Cl and 25 ml of saturated NaHCO3, dried over anhydrous magnesium sulfate and evaporated to afford 760 mg of the title A compound.

B. [1β,2β(5Z),3α(1E,3S*),4β]-7-[3-cyclohexyl-3-t-butyldimethylsilyloxy-1-propenyl)-7-oxabicyclo[2.2.1]hept-2-yl]-5-heptenoic acid To 760 mg (1.4 mmole) of title A ester in 80 ml of 80% THF in water was added 20 ml of 1N LiOH in water and stirred for 30 hours under argon at 25°. The reaction mixture was acidified to pH~3 with oxalic acid, diluted with 500 ml of water and extracted with three 250 ml portions of ether. The ethereal layer was washed with 100 ml of water and 100 ml of brine, dried over anhydrous magnesium sulfate and evaporated to provide an oil.

C. [1β,2β(5Z),3α(1E,3S*),4β]-7-[3-cyclohexyl-3-t-butyldimethylsilyloxy-1-propenyl)-7-oxabicyclo[2.2.1]hept-2-yl]-N-(phenylsulfonyl)-5-heptenamide To 161 mg (0.34 mmole) of the title B acid in 3 ml of anhydrous THF under argon at 25° was slowly added 68.7 mg (0.68 mmole, 2.0 equiv.) of triethylamine and 124.5 mg (0.68 mmole, 2.0 equiv.) of benzenesulfonyl isocyanate. The reaction was stirred for 1 hour, diluted with 50 ml of ethyl acetate, washed successively with 10 ml of saturated NH4Cl, 10 ml of water and 10 ml of brine, and dried over anhydrous magnesium sulfate to furnish 260 mg of an oil. This material was purified by flash chromatography on LP-1 SiO2 using 1% methanol in methylene chloride as an eluent to yield 212.8 mg (99%) of the title C compound as an off-white solid.

D. [1β,2β(5Z),3α(1E,3S*),4β]-7-[3-(3-Cyclohexyl-3-hydroxy-1-propenyl)-7-oxabicyclo[2.2.1]hept-2-yl]-N-(phenylsulfonyl)-5-heptenamide To 212.8 mg (0.35 mmole) of the title C compound in 3 ml of THF was added 1.1 g (3.5 mmole, 10 equiv.) of tetrabutyl ammonium fluoride and this solution was refluxed at 45° under argon for 66 hours. The reaction mixture was cooled, diluted with 50 ml of ether and washed with 10 ml of saturated NH$_4$Cl and the aqueous layer was extracted with 20 ml of ether. The combined ethereal solutions were washed with 10 ml of water and 10 ml of brine and dried over anhydrous magnesium sulfate. The crude product was purified by flash chromatography using LP-1 SiO$_2$ and a 1:1-hexane:ethyl acetate eluent to yield 95 mg (54% yield) of [1β,2β(5Z),3α(1E,3S*),4β]-7-[3-(3-cyclohexyl-3-hydroxy-1-propenyl)-7-oxabicyclo[2.2.1]hept-2-yl]-N-(phenylsulfonyl)-5-heptenamide as a white foam.

Analysis: Calcd for: C, 67.11; H, 8.10; N, 2.65. Found: C, 67.03; H, 7.83; N, 2.79.

EXAMPLE 19

[1β,2β(5Z),3α(1E,3S*),4β]-7-[3-(3-Cyclohexyl-3-hydroxy-1-propenyl)-7-oxabicyclo[2.2.1]hept-2-yl]-N-(methylsulfonyl)-5-heptenamide A. [1β,2β(5Z),3α(1E,3S*),4β]-7-[3-(3-Cyclohexyl-3-t-butyldimethylsiloxy-1-propenyl)-7-oxabicyclo[2.2.1]hept-2-yl]-N-(methylsulfonyl)-5-heptenamide To 176 mg (0.38 mmole) of [1β,2β(5Z),3α(1E,3S*),4β]-7-[3-cyclohexyl-3-t-butyldimethylsilyloxy-1-propenyl)-7-oxabicyclo[2.2.1]hept-2-yl]-5-heptenoic acid (prepared as described in Example 18, part B) in 3 ml of anhydrous THF was added 187 mg (1.85 mmole, 5 equiv.) of triethylamine and 224 mg (1.85 mmole, 5 equiv.) of methylsulfonyl isocyanate. The reaction mixture was stirred for 1 hour under argon at 25°, diluted with 50 ml of ethyl acetate and was successively washed with 10 ml of saturated NH$_4$Cl, 10 ml of water and 10 ml of brine, and dried over anhydrous magnesium sulfate. The crude product was purified by flash chromatography on LP-1 SiO$_2$ using a ½ ethyl acetate:hexane solution as an eluent to provide 125 mg (61% yield) of title A compound as a clear oil.

B. [1β,2β(5Z),3α(1E,3S*),4β]-7-[3-(3-Cyclohexyl-3-hydroxy-1-propenyl)-7-oxabicyclo[2.2.1]hept-2-yl]-N-(methylsulfonyl)-5-heptenamide To 125 mg (0.23 mmole) of title A compound in 3 ml of anhydrous THF under argon at 25° was added 725.6 mg (2.3 mmole, 10 equiv.) of tetrabutyl ammonium fluoride. The reaction mixture was refluxed at 45° for 15 hours, cooled, diluted with 50 ml of ether and washed with 10 ml of saturated NH$_4$Cl. The aqueous layer was extracted with 20 ml of ether and the combined ethereal solutions were washed with 10 ml of water and 10 ml of brine and dried over anhydrous magnesium sulfate. The crude product was purified by flash chromatography using LP-1 SiO$_2$ using a 2:3 hexane:ethyl acetate solution as an eluent to provide 32.1 mg (32% yield) of [1β,2α(5Z),3α(1E,3S*),4β]-7-[3-(3-cyclohexyl-3-hydroxy-1-propenyl)-7-oxabicyclo[2.2.1]hept-2-yl]-N-(methylsulfonyl)-5-heptenamide as a clear colorless oil.

Analysis: Calcd. for: C, 62.84, H, 8.48; N, 3.19. Found: C, 62.72, H, 8.47; N, 3.22.

EXAMPLE 20

[1β,2α(5Z),3α(1E,3S*),4β]-7-[3-(3-Cyclohexyl-3-hydroxy-1-propenyl)-7-oxabicyclo[2.2.1]hept-2-yl]-5-heptenoic acid A. [1β,2α(5Z),3α(1E,3S*),4β]-7-[3-(3-Cyclohexyl-3-hydroxy-1-propenyl)-7-oxabicyclo[2.2.1]hept-2-yl]-5-heptenoic acid A slurry of sodium hydride (50% in oil, 280 mg, 0.0059 mole) in anhydrous dimethoxyethane (100 ml) was treated with a solution of dimethyl 2-oxo-2-cyclohexylethylphosphonate (1.37 g, 0.0059 mole) in DME (10 ml) at 0° C. The mixture was stirred at room temperature for two hours then treated with a solution of [1β,2α(5Z),3α,4β]-7-[3-formyl-7-oxabicyclo[2.2.1]hept-2-yl]-5-heptenoic acid, methyl ester (prepared as described in Example 5) (1.1 g, 0.0041 mole) in DME (10 ml). The mixture was stirred at room temperature for 1.5 hours, quenched with glacial acetic acid (354 mg, 0.0059 mole), then concentrated in vacuo. The residue was dissolved in ether and washed with 5% potassium bicarbonate (1×100 ml). The ether layer was dried over magnesium sulfate and concentrated in vacuo. The residue was purified by chromatography on LP-1 silica gel, eluting with hexane/ether (7:3) to yield 1.1 g of an oil.

A solution of the above crude oil (1.1 g) and cerium chloride heptahydrate (1.1 g, 0.0029 mole) in methanol (30 ml) was chilled in an ice bath and treated portionwise over thirty seconds with sodium borohydride (112 mg, 0.0029 mole). The mixture was stirred at room temperature for ten minutes, then poured into saturated ammonium chloride solution (200 ml) and extracted with ethyl acetate (5×100 ml). The combined extracts were dried over magnesium sulfate and concentrated. The residue was purified by column chromatography on LP-1 silica gel eluting with hexane/ethyl acetate (4:1) to yield 0.33 g of the title A compound.

TLC of title A: silica gel; hexane/ethyl acetate (1:1) R$_f$≈0.5.

B. [1β,2α(5Z),3α(1E,3S*),4β]-7-[3-(3-Cyclohexyl-3-hydroxy-1-propenyl)-7-oxabicyclo[2.2.1]hept-2-yl]-5-heptenoic acid The title A alcohol ester (prepared in part A) (0.33 g, 0.0009 mole) was dissolved in tetrahydrofuran/water (65 ml/15 ml), chilled to 0° C. and treated dropwise with a solution of lithium hydroxide (0.009 mole) in water (9 ml). The reaction mixture was stirred at 0° C. for one hour then seven hours at room temperature and left for the weekend in the cold room. The mixture was then acidified to pH=3 with 10% oxalic acid, poured into water (500 ml) and extracted with ether (3×200 ml). The combined ether extracts were washed with brine and dried over magnesium sulfate and concentrated in vacuo. The residue was purified by flash chromatography on LP-1 silica gel eluting with 2% methanol/dichloromethane to yield 200 mg of the title compound.

This was further purified on CC7 silica gel eluting with distilled pentane (300 ml), pentane/ether (dist.) (1:1) (~200 ml) and ether (dist.) (300 ml) and filtered through millipore filter.

TLC: silica gel; EtOAc R$_f$~0.33; PMA spray and heat.

EXAMPLE 21

1β,2β(5Z),3α(1E,3S*),4β]-7-[3-(3-Cyclohexyl-3-hydroxyl-1-propenyl)-7-oxabicyclo[2.2.1]hept-2-yl]-5-heptenol To 400 mg (1.1 mmol) of [1β,2β(5Z),3α,4β]-7-[3-(3-cyclohexyl-3-hydroxyl-1-propenyl)-7-oxabicyclo[2.2.1]-hept-2-yl]-5-heptenoic acid, methyl ester prepared as described in Example 1 in 10 ml of anhydrous tetrahydrofuran (THF) at 0° is slowly added 0.6 ml of a 1M solution of LiAlH$_4$ in THF. The reaction is stirred for 30 minutes at 0°, and then slowly quenched in a 3% water in THF solution. 500 mg of dry celite is added.

This mixture is stirred for 1 hour, diluted with 100 ml of ether and filtered to provide 325 mg of the title compound.

EXAMPLE 22

[1β,2β(5Z),3α(1E,3S*),4β]-7-[3-(3-Hydroxy-3-cyclohexyl-1-propenyl)-7-oxabicyclo[2.2.1]-hept-2-yl]-5-heptenamide To 456.5 mg (1.3 mmole) of the acid product prepared in Example 1 in 10 ml of anhydrous THF is added 191.3 mg (1.4 mmole) of p-nitrophenol, ca. 10 mg of 4,4-dimethylaminopyridine and 283.3 mg (1.4 mmole) of N,N'-dicyclohexylcarbodiimide. The reaction is stirred for 2 hours under argon at 25° C., then anhydrous ammonia is slowly bubbled through this solution for 1 hour. The solvents are evaporated. The crude oil is purified by column chromatography on silica gel using a 5% methanol in dichloromethane eluent to furnish 333.2 mg of the title compound.

EXAMPLE 23

[1β,2β(5Z),3α(1E,2S*),4β]-N-propyl-7-[3-(3-hydroxy-3-cyclohexyl-1-propenyl)-7-oxabicyclo[2.2.1]hept-2-yl]-5-heptenamide The p-nitrophenol ester is prepared as described in Example 22; 590 mg (10 mmole) of propylamine is added and the reaction is stirred for 3 hours. The solvent is removed in vacuo and the resulting crude oil is purified by column chromatography on silica gel using a 1:2 hexane/ethyl acetate solution as the eluent to afford 219.5 mg of the title compound.

EXAMPLE 24

[1β,2β(5Z),3α(1E,2S*),4β]-N-phenyl-7-[3-(3-hydroxy-3-cyclohexyl-1-propenyl)-7-oxabicyclo[2.2.1]hept-2-yl]-5-heptenamide Following the procedure described in Example 23, substituted aniline for propylamine, the above title compound is obtained.

EXAMPLE 25

[1β,2β(5Z),3α(1E,3S*),4β]-7-[3-(3-Cycloheptyl-3-hydroxy-1-propenyl)-7-oxabicyclo[2.2.1]hept-2-yl]-5-heptenoic acid A. [1β,2β(5Z),3α(1E,3S*),4β]-7-[3-(3-Oxo-3-cycloheptyl-3-hydroxy-1-propenyl)-7-oxabicyclo[2.2.1]hept-2-yl]-5-heptenoic acid To a slurry of 199.4 mg of 50% sodium hydride in mineral oil (4.15 mmole, 1.1 equiv) in 100 ml of anhydrous dimethoxyethane (DME) was added 1.108 g of 2-oxo-2-cycloheptyl propyl dimethyl phosphonate (4.49 mmole, 1.2 equiv.) in 20 ml of DME at 0° C. under an argon atmosphere. The mixture was stirred under argon at 25° C. for one hour. To this solution at 25° C. was added 1.013 g of 1β,2β(5Z),3α,4β]-7-[3-formyl-7-oxabicyclo[2.2.1]hept-2-yl]-5-heptenoic acid, methyl ester prepared as described in Example 1 (3.77 mmole) in 20 ml of DME. After 30 minutes, the reaction was quenched with 1 ml of glacial acetic acid, concentrated, dissolved in 500 ml of ether. The ethereal solution was washed with three 100 ml portions of 5% potassium bicarbonate and 100 ml of brine and dried over anhydrous magnesium sulfate and concentrated. The residue was purified by flash chromatography on LP-1 silica gel column, eluting with 3:7 ether/hexane to provide 898 mg (61.7% yield) of the title A compound.

B. [1β,2β(5Z),3α(1E,2S*),4β]-7-[3-(3-Cycloheptyl-3-hydroxy-1-propenyl)-7-oxabicyclo[2.2.1]-hept-2-yl]-5-heptenoic acid, methyl ester and C. [1β,2β(5Z),3α(1E,3R*),4β]-7-[3-(3-Cycloheptyl-3-hydroxy-1-propenyl)-7-oxabicyclo[2.2.1]-hept-2-yl]-5-heptenoic acid, methyl ester To a solution of 898 mg of the title A compound (2.32 mmole) in 20 ml of dry methanol was added at 25° C. under an argon atmosphere 889 mg of cerium chloride (containing 35% water) (2.32 mmole, 1 equiv.). The reaction was stirred for 10 minutes at 25° C., cooled to 0° C. and 89.7 mg of sodium borohydride (2.32 mmole, 4 equiv.) was slowly added. After stirring for 10 minutes at 0° C., the reaction was poured into 150 ml of saturated ammonium chloride. The mixture was extracted with three 100 ml portions of ether. The ethereal extracts were washed with three 100 ml portions of water and 100 ml of brine. The organic layer was dried over anhydrous magnesium sulfate and concentrated.

The residue was purified on Waters HPLC eluting with 1:3 EtOAc/hexane to give 270 mg of title B compound and 243 mg of title C compound (56.9% yield).

TLC of title B: Silica gel, ethyl acetate/hexane (1:1); $R_f \sim 0.61$.

TLC of title C: $R_f \sim 0.51$.

D. [1β,2β(5Z),3α(1E,3S*),4β]-7-[3-(3-Cycloheptyl-3-hydroxy-1-propenyl)-7-oxabicyclo[2.2.1]hept-2-yl]-5-heptenoic acid 163 mg of the title B alcohol ester (0.42 mmole) was dissolved in 15 ml of an 80% tetrahydrofuran-water solution, chilled to 0° C. and 4.3 ml of a 1N lithium hydroxide solution was added dropwise. The reaction was stirred at 0° C., then slowly warmed up to 25° C. while stirring over a 15 hour period. The THF was evaporated under high vacuum and the residue was diluted with 10 ml of water, acidified to pH 3 with a 10% aqueous oxalic acid solution, and extracted with three 30 ml portions of ether. The organic layer was washed with three 30 ml portions of water and 30 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 4 days to give 153 mg of the title compound (97.3%).

TLC: silica gel; EtOAc/hexane (3:1) $R_f \sim 0.44$.

Analysis: Calcd (includes 0.18 mole of water): C, 72.74; H, 9.64. Found: C, 72.74; H, 9.62.

EXAMPLE 26

[1β,2β(5Z),3α(1E,3R*),4β]-7-[3-(3-Cycloheptyl-3-hydroxy-1-propenyl)-7-oxabicyclo[2.2.1]hept-2-yl]-5-heptenoic acid 153 mg of the title C alcohol ester prepared as described in Example 25 (0.39 mmole) was dissolved in 15 ml of an 80% tetrahydrofuran-water solutibn, chilled to 0° C. and 3.9 ml of a 1N lithium hydroxide solution was added dropwise. The reaction mixture was stirred at 0° C., then slowly warmed up to 25° C. while stirring over an 18 hour period. The THF was evaporated under high vacuum and the residue was diluted with 10 ml of water, acidified to pH 3 with a 10% aqueous oxalic acid solution, and extracted with three 30 ml portions of ether. The organic layer was washed with three 30 ml portions of water and 30 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 4 days to give 145 mg of the title compound (98.3%).

TLC: silica gel; EtOAc/hexane (3:1); $R_f \sim 0.34$.

Analysis: Calcd. (includes 0.17 mole of $H_2O$): C, 72.78; H, 9.64. Found: C, 72.78; H, 9.76.

EXAMPLE 27

[1β,2β(5Z),3α(1E,3S*),4β]-7-[3-(4-Cyclohexyl-3-hydroxy-1-butenyl)-7-oxabicyclo[2.2.1]hept-2-yl]-5-heptenoic acid A. [1β,2β(5Z),3α(1E,3S*),4β]-7-[3-(3-Oxo-4-cyclohexyl-1-butenyl)-7-oxabicyclo[2.2.1]hept-2-yl]-5-heptenoic acid To 402.7 mg of freshly distilled diisopropylamine (3.98 mmole, 1.05 equiv.) in 30 ml of dry toluene at −78° C. was added 2.49 ml of a 1.6M solution of n-butyllithium in hexane (3.98 mmole, 1.05 equiv.). The mixture was stirred for 5 minutes, and to this mixture at −78° C. was added 1.034 g of 2-oxo-cyclohexylpropyl dimethyl phosphonate (4.17 mmole, 1.1 equiv.). The mixture was warmed up to 25° C. while stirring. To this mixture at 25° C. was added 1.0 g of [1β,2β(5Z),3α,4β]-7-[3-formyl-7-oxabicyclo[2.2.1]-hept-2-yl]-5-heptenoic acid, methyl ester (prepared as described in Example 1) (3.79 mmole). After 4.5 hours, the reaction was quenched with 0.5 ml of glacial acetic acid, diluted with 300 ml of ether. The ethereal solution was washed with three 100 ml portions of a 5% sodium bicarbonate solution and 100 ml of brine. The organic layer was dried over anhydrous magnesium sulfate, concentrated to give 1.38 g of a crude oil. This oil was used in the next step without purification.

B. [1β,2β(5Z),3α(1E,3S*),4β]-7-[3-(4-Cyclohexyl-3-hydroxy-1-butenyl)-7-oxabicyclo[2.2.1]-hept-2-yl]-5-heptenoic acid, methyl ester and C. [1β,2β(5Z),3α(1E,3R*),4β]-7-[3-(4-Cyclohexyl-3-hydroxy-1-butenyl)-7-oxabicyclo[2.2.1]-hept-2-yl]-5-heptenoic acid, methyl ester To a solution of 1.05 g of crude title A compound in 25 ml of dry methanol was added at 25° C. under an argon atmosphere 1.04 g of cerium chloride containing 35% water (2.71 mmole, 1 equiv.). The reaction was stirred for 10 minutes at 25° C., cooled to 0° C. and 105 mg of sodium borohydride (2.71 mmole, 4 equiv.) was slowly added. After stirring for 10 minutes at 0° C., the reaction mixture was poured into 150 ml of saturated ammonium chloride. The mixture was extracted with three 100 ml portions of ether. The ethereal extracts were washed with three 100 ml portions of water and 100 ml of brine. The organic layer was dried over anhydrous magnesium sulfate and concentrated.

Separation and purification was done on LP-1 silica gel column eluting with 30% ethyl acetate in hexane to give 233 mg of title B compound and 111 mg of title C compound.

TLC of title B: silica gel; EtOAc/hexane (1:1), $R_f \sim 0.51$.

TLC of title C: $R_f \sim 0.36$.

D. [1β,2β(5Z),3α(1E,3S*),4β]-7-[3-(4-Cyclohexyl-3-hydroxy-1-butenyl)-7-oxabicyclo[2.2.1]-hept-2-yl]-5-heptenoic acid 233 mg of the title B compound (0.6 mmole) was dissolved in 25 ml of an 80% tetrahydrofuran-water solution, chilled to 0° C. and 6.0 ml of a 1N lithium hydroxide solution was added dropwise. The reaction was stirred at 0° C., then slowly warmed up to 25° C. over a 15 hour period. The THF was evaporated under high vacuum and the residue was diluted with 10 ml of water, acidified to pH 3 with a 10% aqueous oxalic acid solution, extracted with three 50 ml portions of ether. The organic layer was washed with three 50 ml portions of water and 50 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 7 days to give 206.7 mg of [1β,2β(5Z),3α(1E,3S*),4β]-7-[3-(3-cyclohexyl-3-hydroxy-1-butenyl)-7-oxabicyclo[2.2.1-]hept-2-yl]-5-heptenoic acid (91.5%).

Analysis: Calcd. (includes 0.2 mole of $H_2O$) C, 72.68; H, 9.65. Found: C, 72.68, H. 9.72.

TLC: silica gel; ethyl acetate; $R_f \sim 0.41$.

EXAMPLE 28

[1β2β(5Z),3α(1E,3R*),4β]-7-[3-(4-Cyclohexyl-3-hydroxy--butenyl)-7-oxabicyclo[2.2.1]hept-2-yl]-5-heptenoic acid 111 mg of the title C alcohol ester (prepared in Example 27) (0.28 mmole) was dissolved in 15 ml of an 80% tetrahydrofuran-water solution, chilled to 0° C. and 2.8 ml of a 1N lithium hydroxide solution was added dropwise. The reaction was stirred at 0° C., then slowly warmed up to 25° C. over a 15 hour period. The THF was evaporated under high vacuum and the residue was diluted with 10 ml of water, acidified to pH 3 with a 10% aqueous oxalic acid solution, extracted with three 30 ml portions of ether. The organic layer was washed with three 30 ml portions of water and 30 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 7 days to give 102.8 mg of [1β,2β(5Z),3α(1E,3R*),4β]-7-[3-(4-cyclohexyl-3-hydroxy-1-butenyl)-7-oxabicyclo[2.2.1-]hept-2-yl]-5-heptenoic acid.

Analysis: Calcd. for: C, 73.36; H, 9.64. Found: C, 73.03; H, 9.61.

TLC: silica gel; ethyl acetate; $R_f \sim 0.32$.

EXAMPLE 29

[1β,2β(5Z),3α(1E,3S*),4β]-7-[3-[3-Hydroxy-4-(3-thienyl)-1-butenyl]-7-oxabicyclo[2.2.1]hept-2-yl]-5-heptenoic acid A. [1β,2β(5Z),3α(1E,3S*),4β]-7-[3-[3-oxo-4-(3-thienyl)-1-butenyl]-7-oxabicyclo[2.2.1]hept-2-yl]-5-heptenoic acid To 402.7 mg of freshly distilled diisopropylamine (3.98 mmole, 1.05 equiv.) in 30 ml of dry toluene at −78° C. was added 2.47 ml of a 1.6M solution of n-butyllithium in hexane (3.98 mmole, 1.05 equiv.). The mixture was stirred for 5 minutes, and to this mixture at −78° C. was added 1.034 g of 2-oxo-3-(3-thienyl)propyl dimethyl phosphonate (4.17 mmole, 1.1 equiv.). The mixture was warmed up to 25° C. while stirring. To this mixture at 25° C. was added 1.0 g of [1β,2β(5Z),3α,4β]-

7-[3-formyl-7-oxabicyclo[2.2.1]-hept-2-yl]-5-heptenoic acid, methyl ester (prepared as described in Example 1) (3.79 mmole). After 3 hours, the reaction was quenched with 0.5 ml of glacial acetic acid, diluted with 300 ml of ether. The ethereal solution was washed with three 100 ml portions of a 5% sodium bicarbonate solution and 100 ml of brine. The organic layer was dried over anhydrous magnesium sulfate, concentrated to give 1.05 g of a crude oil. This oil was used in the next step without purification.

B. [1β,2β(5Z),3α(1E,3S*),4β]-7-[3-[3-Hydroxy-4-(3-thienyl)-1-butenyl]-7-oxabicyclo[2.2.1]-hept-2-yl]-5-heptenoic acid, methyl ester and C. [1β,2β(5Z),3α(1E,3R*),4β]-7-[3-[3-Hydroxy-4-(3-thienyl)-1-butenyl]-7-oxabicyclo[2.2.1]-hept-2-yl]-5-heptenoic acid, methyl ester To a solution of 1.427 g of crude title A compound in 30 ml of dry methanol was added at 25° C. under an argon atmosphere 1.416 g of cerium chloride containing 35% water (3.69 mmole, 1 equiv.). The reaction was stirred for 10 minutes at 25° C., cooled to 0° C. and 142.7 mg of sodium borohydride (3.69 mmole, 4 equiv.) was slowly added. After stirring for 10 minutes at 0° C., the reaction mixture was poured into 200 ml of saturated ammonium chloride. The mixture was extracted with three 100 ml portions of ether. The ethereal extracts were washed with three 100 ml portions of water and 100 ml of brine. The organi layer was dried over anhydrous magnesium sulfate and concentrated.

Separation and purification was done on Water HPLC eluting with 35% ethyl acetate in hexane to give 201 mg of title B compound and 107 mg of title C compound.

TLC of title B: silica gel; EtOAc/hexane (1:1); $R_f \sim 0.39$.

TLC of title C: $R_f \sim 0.29$.

D. [1β,2β(5Z),3α(1E,3S*),4β]-7-[3-[3-Hydroxy-4-(3-thienyl)-1-butenyl]-7-oxabicyclo[2.2.1]hept-2-yl]-5-heptenoic acid 201 mg of the title B alcohol ester (0.52 mmole) was dissolved in 20 ml of an 80% tetrahydrofuran-water solution, chilled to 0° C. and 5.2 ml of a 1N lithium hydroxide solution was added dropwise. The reaction was stirred at 0° C., then slowly warmed up to 25° C. over a 15 hour period. The THF was evaporated under high vacuum and the residue was diluted with 10 ml of water, acidified to pH 3 with a 10% aqueous oxalic acid solution, extracted with three 50 ml portions of ether. The organic layer was washed with three 30 ml portions of water and 30 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane The solvents were evaporated under high vacuum for 7 days to give 150 mg of [1β,2β(5Z),3α(1E,3S*),4β]-7-[3-[3-hydroxy-4-(3-thienyl)-1-butenyl]-7-oxabicyclo[2.2.1-]hept-2-yl]-5-heptenoic acid (76.6%).

Analysis Calcd. for: C, 66.99; H, 7.49. Found: C, 66.76; H, 7.67.

TLC:silica gel; ethyl acetate; $R_f \sim 0.53$.

EXAMPLE 30

[1β,2β(5Z),3α(1E,3R*),4β]-7-[3-[3-Hydroxy-4-(3-thienyl)-1-butenyl]-7-oxabicyclo[2.2.1]hept-2-yl]-5-heptenoic acid 170 mg of the title C alcohol ester (prepared in Example 29) (0.44 mmole) was dissolved in 20 ml of an 80% tetrahydrofuran-water solution, chilled to 0° C. and 4.4 ml of a 1N lithium hydroxide solution was added dropwise. The reaction was stirred at 0° C., then slowly warmed up to 25° C. over a 15 hour period. The THF was evaporated under high vacuum and the residue was diluted with 10 ml of water, acidified to pH 3 with a 10% aqueous oxalic acid solution, extracted with three 50 ml portions of ether. The organic layer was washed with three 30 ml portions of water and 30 ml of brine. The product was dried over anhydrous magnesium sulfate and concentrated to give an oil.

This oil was purified on a CC-7 silica gel column, eluting with a gradient of distilled pentane/ether and filtered through a polycarbonate membrane. The solvents were evaporated under high vacuum for 7 days to give 106 mg of [1β,2β(5Z),3α(1E,3R*),4β]-7-[3-[3-hydroxy-4-(3-thienyl)-1-butenyl]-7-oxabicyclo[2.2.1-]hept-2-yl]-5-heptenoic acid (63.9%).

Analysis: Calcd. for: C, 66.99; H, 7.49. Found: C, 66.80; H, 7.65.

TLC: Silica gel; ethyl acetate; $R_f \sim 0.45$.

EXAMPLE 31

[1β,2α(5Z),3α(1E,3S*),4β]-7-[3-[3-Hydroxy-4-(3-thienyl)-1-butenyl]-7-oxabicyclo[2.2.1]hept-2-yl]-5-heptenoic acid, methyl ester A. [1β,2α(5Z),3α,4β]-7-[3-formyl-7-oxabicyclo[2.2.1-]hept-2-yl]-5-heptenoic acid, methyl ester A solution of diazomethane in ether was prepared via the N-methylnitronitrosoguanidine route (from 3 g of the guanidine in 50 ml of ether with dropwise addition at 0° of 9 ml of 40% KOH). This solution (dried over KOH pellets) was added dropwise to a stirring solution of [1β,2α(5Z),3α,4β]-7-[3-(hydroxymethyl)-7-oxabicyclo[2.2.1]hept-2-yl]-5-heptenoic acid, methyl ester, prepared as described in U.S. Pat. No. 4,143,054 (2.54 g, 10 mmole) in ether (150 ml) over a 10 minute period. Stirring at 0° was continued for 30 minutes when the excess diazomethane was destroyed by the addition of acetic acid (1.5 ml). The solution was washed with NaHCO3 solution, brine and dried over Na2SO4. Concentration under vacuum yielded 2.60 g of ester.

A solution of CrO3.Pyr was prepared in anhydrous CH2Cl2 (from 5.9 g, 59 mmole, of CrO3, 9.5 ml, 118 mmole, of pyridine and 200 ml of CH2Cl2) and stirred at room temperature for 25 minutes. Eight grams of dry celite (dried at 100° overnight) was then added followed by 2.61 g (9.8 mmole) of the above ester dissolved in 5 ml of CH2Cl2. The resulting mixture was stirred under N2 for 15 minutes and then worked up. The celite-CrO3 mixture was removed by filtration and the filtrate was washed sequentially with saturated NaHCO3 solution (2×100 ml), H2O (200 ml) and brine (100 ml). After drying over Na2SO4 the mixture was concentrated under vacuum to give 2.34 g of aldehyde.

B. [1β,2α(5Z),3α(1E),4β]-7-[3-[3-oxo-4-(3-thienyl)-1-butenyl]-7-oxabicyclo[2.2.1]-hept-2-yl]-5-heptenoic acid, methyl ester NaH (50% mineral oil dispersion, 185 mg, 3.85 mmol) was suspended in dry DME (70 ml) under an argon atmosphere. 2-Oxo-3-(3-thienyl)propyldimethylphosphonate (1303 mg, 5.25 mmol) in dry DME (10 ml) was added dropwise at room temperature under vigorous stirring. A yellow colored suspension was obtained. After 90 minutes stirring, aldehyde of title A (932 mg, 3.5 mmol) in dry DME (5 ml) was added at room temperature. Stirring was continued for 3 hours. The reaction was quenched by adding acetic acid, and poured into ether (~250 ml), which was washed with saturated NaHCO$_3$, brine and dried over MgSO$_4$. Filtration and evaporation of solvents in vacuo gave a yellow green oil (1.85 g), which was purified by silica gel chromatography eluted with pet.ether/ether (4:1, 3:1, 2:1). The desired trans enone [1β,2α(5Z),3α(1E),4β]-7-[3-[3-oxo-4-(3-thienyl)-1-butenyl]-7-oxabicyclo[2.2.1]hept-2-yl]-5-heptenoic acid, methyl ester (489 mg, 36%) was obtained.

C. [1β,2α(5Z),3α(1E,3S*),4β]-7-[3-[3-Hydroxy-4-(3-thienyl)-1-butenyl]-7-oxabicyclo[2.2.1]hept-2-yl]-5-heptenoic acid, methyl ester and D. [1β,2α(5Z),3α(1E,3R*),4β]-7-[3-[3-Hydroxy-4-(3-thienyl)-1-butenyl]-7-oxabicyclo[2.2.1]hept-2-yl]-5-heptenoic acid, methyl ester The title B enone (475 mg, 1.22 mmol) was dissolved in MeOH (12 ml) and THF (1.2 ml) and cooled at 0° C. CeCl$_3$.7.6 H$_2$O (469 mg, 1.22 mmol) was added, followed by portionwise addition of NaBH$_4$ (45.3 mg, 1.22 mmol). The ice bath was removed and stirring was continued for 8 minutes. The reaction was poured into saturated NH$_4$Cl (90 ml). The products were extracted with EtOAc (4×50 ml) and dried over Na$_2$SO$_4$. Filtration and evaporation of solvents gave a viscous oil (550 mg), which was purified by silica gel column chromatography eluted with pet. ether/ether (7:3-1:1) to give the title C isomer (317 mg, 66%) and the title D isomer (115 mg, 24%).

TLC: silica gel, Et$_2$O/Pet. ether - 3:2, vanillin R$_f$=0.22.

Analysis of title C compound: Calcd for C$_{22}$H$_{30}$O$_4$S: C, 67.66; H, 7.74; S, 8.21. Found: C, 67.28; H, 7.76; S, 8.01.

EXAMPLE 32

[1β,2α(5Z),3α(1E,3R*),4β]-7-[3-[3-Hydroxy-4-(3-thienyl)-1-butenyl]-7-oxabicyclo[2.2.1]hept-2-yl]-5-heptenoic acid The Example 31D ester [1β,2α(5Z),3α(1E,3R*),4β]-7-[3-[3-hydroxy-4-[3-thienyl)-1-butenyl]-7-oxabicyclo[2.2.1]hept-2-yl]-5-heptenoic acid, methyl ester (93.7 mg, 0.24 mmol) was dissolved in THF (13 ml) and H$_2$O (2.4 ml) under an argon atmosphere. The reaction was cooled down to 0° C., where 1N-LiOH (2.4 ml) was added. The reaction was warmed to room temperature and stirring was continued for 6½ hours. The reaction was acidified with saturated oxalic acid to pH 3 and poured into H$_2$O (80 ml). The products were extracted with ether (3×40~60 ml). The combined ether layers were washed with H$_2$O (3×40 ml), brine (25 ml) and dried over MgSO$_4$. Filtration and evaporation of solvents in vacuo gave a colorless oil (88.5 mg, 98%).

TLC: Silica gel, Et$_2$O, vanillin R$_f$=0.25.

Analysis: Calc'd for C$_{21}$H$_{28}$O$_4$S: C, 66.99; H, 7.50; S, 8.52. Found: C, 66.64; H, 7.31; S, 8.52.

EXAMPLE 33

[1β,2α(5Z),3α(1E,3S*),4β]-7-[3-[3-Hydroxy-4-(3-hydroxy-4-(3-thienyl)-1-butenyl]-7-oxabicyclo[2.2.1]hept-2-yl]- 5-heptenoic acid The Example 31C ester, [1β,2α(5Z),3α(1E,3S*),4β]-7-[3-[3-hydroxy-4-(3-thienyl)-1-butenyl]-7-oxabicyclo[2.2.1]hept-2-yl]-5- heptenoic acid, methyl ester, (237 mg, 0.608 mmol) was dissolved in THF (32 ml) and H$_2$O (6 ml), and cooled at 0° C. under an argon atmosphere. 1N-LiOH (6 ml) was added and the reaction was warmed to room temperature. After 6½ hours stirring, the reaction was acidified to pH 3 with saturated oxalic acid. The reaction was poured into H$_2$O (200 ml). The products were extracted with ether (3×100~150 ml). The combined ether layers were washed with H$_2$O (3×100 ml), brine (50 ml) and dried over MgSO$_4$. Filtration and evaporation of solvents in vacuo gave a colorless oil (212.6 mg, 92%).

TLC: Silica gel, Et$_2$O, vanillin R$_f$=0.32.

Analysis: Calc'd for C$_{21}$H$_{28}$O$_4$S.0.2 H$_2$O: C, 66.36; H, 7.53; S, 8.43. Found: C, 66.51; H, 7.77; S, 8.07.

EXAMPLE 34

[1β,2α(5Z),3α(1E,3S*),4β]-7-[3-(3-Hydroxy-4-phenoxy-1-butenyl)-7-oxabicyclo[2.2.1]hept-2-yl]-5-heptenoic acid A. [1β,2α(5Z),3α(1E),4β]-7-[3-(3-Oxo-4-phenoxy-1-butenyl)-7-oxabicyclo[2.2.1]-hept-2-yl]-5-heptenoic acid Sodium hydride (264 mg of 50% in mineral oil, 5.5 mmol) was suspended in dry dimethoxyethane (50 ml) in an argon atmosphere. A solution of 2-oxo-3-phenoxypropyldimethyl phosphonate (1.9 g, 7.5 mmol) in 10 ml DME was added. The mixture became nearly clear and material began precipitating out of solution. After 45 minutes dist HMPA (hexamethyl phosphoric triamide) (5 ml) was added and the mixture was stirred an additional 45 minutes at room temperature. A solution of aldehyde [1β,2α(5Z),3α,4β]-7-[3-formyl-7-oxabicyclo[2.2.1]hept-2-yl]-5-heptenoic acid, methyl ester (1.33 g, 5 mmol) in DME (4 ml) was then added and the mixture was left stirring overnight at room temperature. The reaction was quenched by adding 0.6 ml glacial acetic acid and the solvent was removed in vacuo. The residue was dissolved in ether and washed three times with 1N HCl and twice with saturated NaHCO$_3$ solution The ether solution was dried over MgSO$_4$ and freed of solvent in vacuo to give 2.25 g oil. This was chromatographed on 110 g silica gel 60 eluting with ether-pet ether (2:3) to give 906 mg (46%) of the desired title A compound.

B. [1β,2α(5Z),3α(1E,3S*),4β]-7-[3-(3-Hydroxy-4-phenoxy-1-butenyl)-7-oxabicyclo[2.2.1]hept-2-yl]-5-heptenoic acid, methyl ester and C. [1β,2α(5Z),3α(1E,3R*),4β]-7-[3-(3-Hydroxy-4-phenoxy-1-butenyl)-7-oxabicyclo[2.2.1]-hept-2-yl]-5-heptenoic acid, methyl ester The title A compound (906 mg, 2.27 mmol) and cerium chloride hydrate (35.7%, 0.872 g, 2.27 mmol) were dissolved in 22 ml methanol and 2 ml THF in an argon atmosphere. The solution was cooled in an ice bath and sodium borohydride (86 mg, 2.27 mmol) was added portionwise in 30 seconds. The ice bath was removed and the mixture was stirred 8 minutes and then poured into 200 ml saturated NH$_4$Cl solution. The product was extracted into ethyl acetate (5×50 ml), dried and freed of solvent in vacuo leaving 0.9 g of viscous oil. This was chromatographed on 50 g silica gel 60 eluting with ether-pet ether 3:2 to give the title B isomer, 445 mg (49%) and the title C isomer 268 mg (29%).

TLC: silica gel; ether-pet ether 2:1; vanillin R$_f$'s: 0.32 & 0.21.

D. [1β,2α(5Z),3α(1E,3S*),4β]-7-[3-(3-Hydroxy-4-phenoxy-1-butenyl)-7-oxabicyclo[2.2.1]-hept-2-yl]-5-heptenoic acid The title B methyl ester described above (438 mg, 1.1 mmol) was dissolved in 55 ml THF and 10.5 ml H$_2$O in a nitrogen atmosphere. The solution was cooled in an ice bath and 11.0 ml 1N LiOH was added. The ice bath was removed and the mixture was stirred at room temperature for 6 hours. Saturated oxalic acid solution was then added to adjust the pH to 3 and the mixture was poured into 400 ml water. The product was extracted into ether (3×200 ml). The combined ether extracts were washed three times with water and once with saturated NaCl solution, dried and freed of solvent in vacuo leaving 407 mg (95%) of the title D compound in the form of a viscous oil.

TLC: silica gel; Et$_2$O; vanillin R$_f$=0.29.

Analysis: Calcd. for C$_{23}$H$_{30}$O$_5$.0.2 H$_2$O: C, 70.81; H, 7.86. Found: C, 70.86; H, 7.85.

EXAMPLE 35

[1β,2α(5Z),3α(1E,3R*),4β]-7-[3-(3-Hydroxy-4-phenoxy-1-butenyl)-7-oxabicyclo[2.2.1]hept-2-yl]-5-heptenoic acid The Example 34C methyl ester ([1β,2α(5Z),3α-(1E,3R*),4β]-7-[3-(3-hydroxy-4-phenoxy-1-butenyl)-7-oxabicyclo[2.2.1]hept-2-yl]-5-hepten oic acid, methyl ester) (121 mg, 0.3 mmol) was dissolved in 15 ml THF and 2.9 ml water in an argon atmosphere. The solution was cooled in an ice bath and 3.0 ml 1N LiOH was added. The ice bath was removed and the mixture was stirred at room temperature 6½ hours. The pH was then adjusted to 3 with a saturated solution of oxalic acid and the mixture was poured into 125 ml water. The product was extracted into ether (3×50 ml). The combined ether extracts were washed three times with water and once with saturated NaCl solution, dried over MgSO$_4$, and freed of solvent in vacuo to give 109 mg (93%) of the title compound in the form of a viscous oil.

TLC: silica gel; Et$_2$O; vanillin, R$_f$=0.15.

Analysis: Calcd. for C$_{23}$H$_{30}$O$_5$.0.2 H$_2$O: C, 70.81; H, 7.86. Found: C, 70.66; H, 7.65.

EXAMPLE 36

[1β,2α(5Z),3α(1E,3S*),4β]-7-[3-(3-Hydroxy-4-phenyl-1-butenyl)-7-oxabicyclo[2.2.1]hept-2-yl]-5-heptenoic acid A. [1β,2α(5Z),3α(1E),4β]-7-[3-(3-Oxo-4-phenyl-1-butenyl]-7-oxabicyclo[2.2.1]-hept-2-yl]-5-heptenoic acid Sodium hydride (238 mg of 50% in mineral oil, 4.95 mmol) was suspended in dry dimethoxyethane (90 ml) in an argon atmosphere. A solution of 2-oxo-3-phenyl-propyldimethyl phosphonate (1.63 g, 6.75 mmol) in 10 ml DME was added. The mixture was stirred at room temperature 90 minutes. A solution of [1β,2α(5Z)-,3α,4β]-7-[3-formyl-7-oxabicyclo[2.2.1]hept-2-yl]-5-heptenoic acid, methyl ester (prepared as described in Example 31) (1.2 g, 4.5 mmol) in 5 ml DME was added and the mixture was stirred at room temperature 4½ hours. The reaction was then quenched by adding 0.5 ml glacial acetic acid and the solvent was removed in vacuo. The residue was partitioned between ether and saturated NaHCO$_3$ solution The ether layer was washed once more with saturated NaHCO$_3$, dried over MgSO$_4$ and taken to dryness in vacuo leaving 2.25 g oil. This was chromatographed on 20 g silica gel 60 eluting with ether-pet ether 2:3 to give 980 mg (60%) of the title A compound (single spot material).

B. [1β,2α(5Z),3α(1E,3S*),4β]-7-[3-(3-Hydroxy-4-phenyl-1-butenyl)-7-oxabicyclo[2.2.1]hept-2-yl]-5-heptenoic acid, methyl ester and C. [1β,2α(5Z),3α(1E,3R*),4β]-7-[3-(3-Hydroxy-4-phenyl-1-butenyl)-7-oxabicyclo[2.2.1]hept-2-yl]-5-heptenoic acid, methyl ester The title A compound (980 mg, 2.6 mmol) and cerium (III) chloride hydrate (35.7% H$_2$O, 0.982 g, 2.6 mmol) were dissolved in 25 ml methanol and 2 ml THF in an argon atmosphere. The solution was cooled in an ice bath and sodium borohydride (97 mg, 2.6 mmol) was added portionwise in 30 seconds. The ice bath was removed and the mixture was stirred for 8 minutes, then poured into saturated NH$_4$Cl solution (200 ml). The product was extracted into ethyl acetate (5×50 ml) dried and freed of solvent in vacuo leaving 930 mg viscous oil. This was chromatographed on 65 g silica gel 60 eluting with ether-pet ether 3:2 to give 446 mg (45%) of the title B methyl ester and 156 mg (16%) of the title C isomer.

TLC's: silica gel, Et$_2$O-P.E.3:2, vanillin R$_f$'s - 0.44 and 0.30.

D. [1β,2α(5Z),3α(1E,3S*),4β]-7-[3-(3-Hydroxy-4-phenyl-1-butenyl)-7-oxabicyclo[2.2.1]-hept-2-yl]-5-heptenoic acid The title B methyl ester described above (440 mg, 1.14 mmol) was dissolved in 58 ml THF and 11 ml H$_2$O in an argon atmosphere. The solution was cooled in an ice bath and 11.4 ml 1N LiOH was added with stirring. The ice bath was removed and the mixture was stirred at room temperature 6 hours. Saturated oxalic acid solution was then added to adjust the pH to 3 and the mixture was poured into 400 ml water. The product was extracted into ether (3×200 ml). The combined ether extracts were washed three times with water and once with saturated NaCl solution, dried and freed of solvent in vacuo leaving 425 mg (98%) of the title compound in the form of an oil.

TLC: silica gel, Et$_2$O, vanillin. R$_f$=0.18.

Analysis: Calc'd for C$_{23}$H$_{30}$O$_4$.0.3 H$_2$O: C, 73.49, H, 8.21. Found: C, 73.66; H, 8.51.

EXAMPLE 37

[1β,2α(5Z),3α(1E,3R*),4β]-7-[3-(3-Hydroxy-4-phenyl-1-butenyl)-7-oxabicyclo[2.2.1]hept-2-yl]-5-heptenoic acid The Example 36C methyl ester ([1β,2α(5Z),3α-(1E,3R*),4β]-7-[3-(3-hydroxy-4-phenyl-1-butenyl)-7-oxabicyclo[2.2.1]hept-2-yl]-5-hepteno ic acid, methyl ester) (150 mg, 0.39 mmol) was dissolved in 20 ml THF and 3.8 ml water in an argon atmosphere. The solution was cooled in an ice bath and 3.9 ml 1N LiOH was added. The ice bath was removed and the mixture was stirred at room temperature 6 hours. The pH was then adjusted to 3 with a saturated solution of oxalic acid and the mixture was poured into 150 ml water. The product was extracted into ether (3×50 ml). The combined ether extracts were washed three times with water and once with saturated NaCl solution, dried over MgSO$_4$ and freed of solvent in vacuo to give 142 mg (97%) of the title compound B.

TLC—silica gel, Et$_2$O, vanillin R$_f$=0.12.

Analysis: Calcd for C$_{23}$H$_{30}$O$_4$.0.2M H$_2$O: C, 73.84; H, 8.19. Found: C, 74.00; H, 8.39.

EXAMPLE 38

[1β,2β(5Z),3α(3S*),4β]-7-[3-(3-Hydroxyl-1-octynyl)-7-oxabicyclo[2.2.1]hept-2-yl]-5-heptenoic acid A. [1β,2β(5Z),3α(1EZ),4β]-7-[3-(2-bromo-3-oxo-1-octenyl)-7-oxabicyclo[2.2.1]-hept-2-yl]-5-heptenoic acid, methyl ester To a slurry of 50% sodium hydride in mineral oil (144 mg, 3 mmol) in 40 ml of anhydrous dimethoxyethane (DME) is added a solution of 1-bromo-2-oxo-heptyl-dimethylphosphonate (963.2 mg, 3.2 mmol) in 5 ml of DME. The mixture is stirred at 25° for 90 minutes. A solution of [1β,2β(5Z),3α,4β]-7-[3-formyl-7-oxabicyclo[2.2.1]-hept-2-yl]-5-heptenoic acid, methyl ester (prepared as described in Example 1) (700 mg, 2.6 mmol) in 5 ml of DME is added and the mixture is stirred at 25° for 3 hours. The reaction is quenched with 0.2 ml glacial acetic acid and the solvent is removed in vacuo. The residue is diluted with ether and washed with a saturated NaHCO$_3$ solution. The ether layer is dried over MgSO$_4$, filtered and taken to dryness in vacuo to provide 1.2 g of an oil. This is chromatographed on silica gel eluting with ethylacetate hexane to give 994.0 mg of the title A compound as a mixture of E and Z isomers.

B. [1β,2β(5Z),3α(3S*R*,1EZ),4β]-7-[3-(2-Bromo-3-hydroxyl-1-octenyl)-7-oxabicyclo[2.2.1]-hept-2-yl]-5-heptenoic acid, methyl ester To 994 mg (2.1 mmol) of the title A ketone and 979.5 mg (2.5 mmol) of cerium chloride heptahydrate in 20 ml of methanol at 0° is added 94 mg (2.5 mmol) of sodium borohydride. The reaction is stirred for 10 minutes, poured into ml of a saturated NH$_4$Cl solution and dried over anhydrous MgSO$_4$ to afford 1.0 g of the title B compound as an oil.

C. [1β,2β(5Z),3α(3S*),4β]-7-[3-(3-Hydroxyl-1-octynyl)-7-oxabicyclo[2.2.1]hept-2-yl]-5-heptenoic acid, methyl ester and D. [1β,2β(5Z),3α(3R*),4β]-7-[3-(3-Hydroxyl-1-octynyl)-7-oxabicyclo[2.2.1]hept-2-yl]-5-heptenoic acid, methyl ester To 1.0 g (2.1 mmol) of the title B compound in 10 ml of anhydrous tetrahydrofuran is added 480 mg (4.3 mmol) of potassium t-butoxide. The reaction is stirred for 15 minutes, acidified with 0.1 N HCl and extracted with ethyl acetate, washed with saturated NaHCO$_3$, and dried over anhydrous magnesium sulfate to afford 862 mg of an oil. This material is purified by silica chromatography using 1:1 ether-hexane to provide 310 mg of the title C isomer and 253 mg of the title D isomer; R$_f$—0.45 and R$_f$0.40, respectively, in 1:1 ether-petroleum ether.

E. [1β,2β(5Z),3α(3S*),4β]-7-[3-(3-Hydroxyl-1-octynyl)-7-oxabicyclo[2.2.1]hept-2-yl]-5-heptenoic acid To 310 mg (0.79 mmol) of the title C ester is dissolved in 40 ml of THF and 10 ml of water, cooled to 0° and 6.9 ml of a 1N LiOH solution is added. The reaction is stirred for 6 hours at 25°, acidified to pH 3 with 10% oxalic acid, diluted with 300 ml of water and extracted with three 200 ml portions of ether. The etheral layer is washed with water and brine and dried over anhydrous MgSO$_4$ to afford 2.82 mg of the title compound.

EXAMPLE 39

[1β,2β(5Z),3α(3R*),4β]-7-[3-(3-Hydroxyl-1-octynyl)-7-oxabicyclo[2.2.1]hept-2-yl]-5-heptenoic acid To 253 mg (0.64 mmol) of the title D ester of Example 38 is dissolved in 40 ml of THF and 10 ml of water, cooled to 0°, and 7 ml of 1N LiOH is added. The reaction is stirred for 6 hours and acidified to pH 3 with oxalic acid, diluted with 200 ml of water and extracted with three 200 ml portions of ether The ethereal layer is washed with water and brine and dried over MgSO$_4$ to afford 2.26 mg of the title compound.

EXAMPLES 40 AND 41

[1β,2β(5Z),3α(1E,3S*),4β]-6-[3-(3-Hydroxy-3-cyclohexyl-1-propenyl)-7-oxabicyclo[2.2.1]hept-2-yl)-1-(1H-tetrazol-5-yl)-4-h exene and

[1β,2β(5Z),3α(1E,3R*),4β]-6-[3-(3-Hydroxy-3-cyclohexyl-1-propenyl)-7-oxabicyclo[2.2.1]hept-2-yl]-1-(1H-tetrazol-5-yl)-4-hexene A. [1β,2β(5Z),3β,4β]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)-butyl phosphonium bromide in 100 ml of tetrahydrofuran (THF) at 0° is added 1.39 g (11.8 mmole) potassium t-butoxide. The reaction is stirred at 25° for 30 minutes and (endo)octahydro-5,8-epoxy-1H-benzopyran-3-ol (prepared as described in U.S. Pat. No. 4,143,054 is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO$_3$ solution, washed with 100 ml of ether, acidified with dilute HCl to pH 3, and extracted with three 500 ml portions of ethyl acetate. The combined organic solutions are dried over anhydrous MgSO$_4$, and purified by silica chromatography using a 5% methanol in methylene chloride eluent to provide 756 mg of title A compound.

B. [1β,2β(5Z),3β,4β]-7-[3-formyl-7-oxabicyclo[2.2.1]hept-2-yl]-1-(1H-tetrazol-5-yl)-4-hexene To 756 mg (2.5 mmole) of title A compound in 15 ml of anhydrous CHCl$_2$ under argon at 25° is added 110 mg (5.4 mmole) of pyridiniumchlorochromate. The reaction is stirred for 3 hours, diluted with 100 ml of ether, filtered through florosil, and evaporated to afford 672 mg of the title B compound.

C. [1β,2β(5Z),3α,4β]-7-[3-formyl-7-oxabicyclo[2.2.1]hept-2-yl]-1-(1H-tetrazol-5-yl)-4-hexane To 690 mg (2.3 mmole) of the title B alcohol in methanol is added 66 mg (1.25 mmole) of sodium methoxide. The reaction is stirred at 25° for 2 hours, diluted with 50 ml of saturated NH$_4$Cl, and extracted with four 100 ml portions of ether. The ethereal layer is washed with brine and dried over MgSO$_4$ to afford 685 mg of the title C compound.

D. [1β,2β(5Z),3α(1E),4β]-7-[3-(3-Oxo-3-cyclohexyl-1-propenyl)-7-oxabicyclo[2.2.1]hept-2-yl)-1-(1H-tetrazol-5-yl)-4-hexene To 190 mg of 50% sodium hydride in mineral oil (3.9 mmole) in 60 ml of anhydrous dimethoxyethane (DME) is added 880 mg (3.9 mmole) of 2-oxo-2-cyclohexylethyldimethylphosphonate. The mixture is stirred at 25°

C. for 1.5 hours. To this solution at 25° is added 685 mg of title C compound in 10 ml of DME. After 1 hour the reaction is quenched with 0.5 ml of glacial acetic acid, concentrated, dissolved in 500 ml of ether. The ethereal solution is washed with 100 ml of water and 100 ml of brine and dried over MgSO4 to afford, following silica chromatography using a 5% methanol in CH2Cl2 eluent, 823 mg of title D compound.

E. [1β,2β(5Z),3α(1E,3S*),4β]-6-[3-(3-Hydroxy-3-cyclohexyl-1-propenyl)-7-oxabicyclo[2.2.1]hept-2-yl)-1-(1H-tetrazol-5-yl)-4-hexene and F. [1β,2β(5Z),3α(1E,3R*),4β]-6-[3-(3-Hydroxy-3-cyclohexyl-1-propenyl)-7-oxabicyclo[2.2.1]hept-2-yl]-1-(1H-tetrazol-5-yl)-4 -hexene To a solution 823 mg (2.15 mmole) of title D compound in 20 ml of dry methanol is added at 25° under argon 890 mg (2.32 mmole) of cerium chloride heptahydrate. The reaction is cooled to 0° and 89.0 mg (2.32 mmole) of sodium borohydride is added. The reaction is stirred for 10 minutes, diluted with 150 ml of saturated NH4Cl, and extracted with three 100 ml portions of ether, washed with water and dried over anhydrous magnesium sulfate. The residue is purified on a Waters HPLC, eluting with 2% methanol in methylenechloride to afford 232 mg of title E compound and 211 mg of title F compound.

EXAMPLE 42

[1β,2β(5Z),3α(1E,3S*,4R*S*),4β]-7-[3-(3-hydroxy-4-methyl-oct-1-ene-6-ynyl]-5-heptenoic acid A. [1β,2β(5Z),3α(1E,4R*S*),4β]-7-[3-(3-oxo-4-methyl-oct-1-ene-6-ynyl]-5-heptenoic acid, methyl ester To a slurry of 301.6 mg of 50% sodium hydride in mineral oil and 150 ml of anhydrous dimethoxyethane (DME) is added 1.32 g (5.7 mmole) of 2-oxo-3-methyl-hept-5-yne dimethylphosphonate (prepared as described in U.S. Pat. No. 4,235,930) in 15 ml of DME at 0° C. under an argon atmosphere. The mixture is stirred at 25° for 1.5 hours. To the solution at 25° is added 1.05 g (3.9 mmole) of [1β,2β(5Z),3α,4β]-7-[3-formyl-7-oxabicyclo[2.2.1]hept-2-yl]-5-heptenoic acid, methyl ester (prepared as described in Example 1) in 15 ml of DME. After 1 hour the reaction is quenched with 0.7 ml of glacial acetic acid, concentrated, dissolved in 500 ml of ether, washed with three 100 ml portions of 5% NaHCO3 and 100 ml of brine. The organic layer is dried over MgSO4 and concentrated to give 1.66 g of crude title A compound.

B. [1β,2β(5Z),3α(1E,3S*,4R*S*),4β]-7-[3-(3-Hydroxy-4-methyl-oct-1-ene-6-ynyl]-5-heptenoic acid, methyl ester and C. [1β,2β(5Z),3α(1E,3R*,4R*S*),4β]-7-[3-(3-Hydroxy-4-methyl-oct-1-ene-6-ynyl]-5-heptenoic acid, methyl ester To a solution of crude title A compound in 30 ml of dry methanol is added at 25° C. under argon 1.8 g (4.6 mmole) of cerium chloride heptahydrate. This mixture is cooled to 0° C. and 180 mg (4.6 mmole) of sodium borohydride is added. This mixture is stirred for 10 minutes at 0°, diluted with 200 ml of saturated NH4Cl and extracted with three 100 ml portions of ether. This ethereal layer is washed with water and brine, and dried over anhydrous MgSO4.

The residue is purified on a WatersHPLC, eluting with 1:4 EtOAc/hexane to afford 232 mg of title B compound and 216 mg of title C compound.

D. [1β,2β(5Z),3α(1E,3S*,4R*S*),4β]-7-[3-(3-Hydroxy-4-methyl-oct-1-ene-6-ynyl]-5-heptenoic acid To 232 mg (0.6 mmole) of the title B alcohol ester dissolved in 30 ml of 80% tetrahydrofuran-water solution at 0° is added 5.5 ml of a 1 N lithium hydroxide solution. The reaction mixture is diluted with 10 ml of water, acidified to pH 3 with oxalic acid, and extracted with three 100 ml portions of ether and washed with brine. The product is dried over anhydrous MgSO4 to afford 172 mg of the title compound.

EXAMPLE 43

[1β,2β(5Z),3α(1E,3R*,4R* S*),4β]-7-[3-(3-Hydroxy-4-methyl-oct-1-ene-6-ynyl]-5-heptenoic acid Following the procedure outlined in Example 42 part D, substituting the title C compound for the title B compound, the above title compound is obtained.

EXAMPLE 44

[1β,2β(5Z),3α(1E,3S*,4R*S*,5Z),4β]-7-[3-(3-Hydroxy-4-methyl-1,5-octadiene]-5-heptenoic acid Following the procedure outlined in Example 42, substituting cis-2-oxo-3-methyl-hept-5-ene dimethylphosphonate [obtained by the catalytic reduction of 2-oxo-3-methyl-hept-5-yne dimethylphosphonate, see Journal American Chemical Society, 78, 2518 (1956)] for 2-oxo-3-methyl-hept-5-yne dimethylphosphonate the above title compound is obtained.

EXAMPLE 45

[1β,2β(5Z),3α(1E,3R*,4R*S*,5Z),4β]-7-[3-[3-Hydroxy-4-methyl-1,5-octadiene]-5-heptenoic acid Following the procedure outlined in Example 43, substituting cis-2-oxo-3-methyl-hept-5-ene dimethylphosphonate for 2-oxo-3-methyl-hept-5-yne dimethylphosphonate, the above title compound is obtained.

EXAMPLE 46

[1β,2β(5Z),3α(1E,3S*)4β]-7-[3-(3-Cyclohexyl-3-hydroxy-1-propenyl)-7-oxabicyclo[2.2.1]hept-2-yl]-N-hydroxy-5-heptenamide To 200 mg (0.53 mmole) of title C1 compound from Example 1 in 20 ml of 95% ethanol is added 365.7 mg (5.3 mmole) of hydroxyamine hydrochloride and 434.6 mg (5.3 mmole) of sodium acetate. The reaction is refluxed for 18 hours under an argon atmosphere, cooled to 25°, diluted with 200 ml of ether wash with 20 ml of water and 20 ml of brine, and dried over anhydrous magnesium sulfate to afford, following chromatography on silica gel, eluting with 5% methanol in dichloromethane, 105.6 mg of the title compound.

EXAMPLE 47

[1β,2β(5Z),3α(1E,3S*),4β]-7-[3-[3-(3-Pyridyl)-3-hydroxy-1-propenyl]-7-oxabicyclo[2.2.1]hept-2-yl]-5-heptenoic acid By substituting 2-oxo-2-(3-pyridyl)ethyldimethylphosphonate (prepared as described hereinbefore) for 2-oxo-2-cyclohexylethyldimethylphosphonate in Example 1,the title compound is obtained.

EXAMPLE 48

[1β,2β(5Z),3α(1E,3S*),4β]-7-[3-[4-(3-Pyridyl)-3-hydroxy-1-butenyl]-7-oxabicyclo[2.2.1]hept-2-yl]-5-heptenoic acid By substituting 2-oxo-3-(3-pyridyl)propyldimethylphosphonate for 2-oxo-2-cyclohexylethyldimethylphosphonate in Example 1, the title compound is obtained.

EXAMPLES 49 AND 50

[1β,2α(5Z),3α(1E,3α,4α),4β]-7-[3-(3-Hydroxy-4-phenyl-1-pentenyl)-7-oxabicyclo[2.2.1]hept-2-yl]-5-heptenoic acid (fast moving isomer A) and

[1β,2α(5Z),3α(1E,3α,4β), 4β]-7-[3-(3-Hydroxy-4-phenyl-1-pentenyl)-7-oxabicyclo[2.2.1]hept-2-yl]-5-heptenoic acid (fast moving isomer B)

A. Methyl 2-phenylpropionate

2-Phenylpropionic acid (8.4 g, 56 mmol) in methanol (180 ml) and concentrated $H_2SO_4$ (2 ml) were heated at reflux for 4 hours. The reaction was cooled down to room temperature and concentrated in vacuo (~30 ml), which was poured into ice water (~100 ml). The products were extracted with $Et_2O$ (150 ml×3), which was washed with saturated $NaHCO_3$, $H_2O$ and dried over $MgSO_4$. Filtration and evaporation of solvent yielded a yellow oil (8.9 g), which was distilled to give a colorless oil (8.34 g, 51 mmol, 91%, b.p. 73° C./1.5 mm Hg).

B. 2-Oxo-3-phenylbutyl dimethyl phosphonate n-BuLi (1.6M, 62.5 ml, 100 mmol) was added dropwise to a magnetically stirred solution of dimethyl methyl phosphonate (12.4 g, 100 mmol) in THF (90 ml) at −78° C. Stirring was continued for 30 minutes at −78° C. Then Part A ester (8.2 g, 50 mmol) was added dropwise to give a yellow colored solution. After 3 hours stirring at −78° C., the reaction was warmed to room temperature and stirred for 1 hour. The reaction was quenched by addition of AcOH to pH 5~6. The solvent was removed in vacuo and $H_2O$ (100 ml) was added. The products were extracted with $CH_2Cl_2$ (100 ml×3), which was washed with saturated $NaHCO_3$, $H_2O$ and dried over $MgSO_4$. Filtration and evaporation of solvent left a yellow oil. This was fractionated to give the desired compound (8.1 g, 31.6 mmol, 63%, b.p. 142°–144°/0.2 mm Hg).

C. [1β,2α(5Z),3α(1E),4β]-7-[3-(3-Oxo-4-phenyl-1-pentenyl)-7-oxabicyclo[2.2.1]hept-2-yl]-5-heptenoic acid, methyl ester Sodium hydride (201 mg of 50% in mineral oil, 4.18 mmol) was suspended in distilled dimethoxyethane (70 ml) in an argon atmosphere and treated with a solution of title B phosphonate (1.45 g, 4.7 mmol) in DME (10 ml). The mixture was stirred at room temperature 90 minutes. A solution of [1β, 2α(5Z),3α, 4β]-7-[3-formyl-7-oxabicyclo[2.2.1]hept-2-yl]-5-heptenoic acid, methyl ester (prepared as described in Example 5) (1.031 g, 3.8 mmol) in DME (5 ml) was then added and the mixture was stirred overnight at room temperature. The reaction was quenched by adding glacial acetic acid (0.5 ml) and the solvent was removed in vacuo. Ether and saturated $NaHCO_3$ were added and the layers were separated. The ether layer was washed once with saturated $NaHCO_3$ solution, dried over $MgSO_4$, filtered and taken to dryness in vacuo leaving a viscous oil. This was chromatographed on silica gel 60 (110 g) eluting with ether-pet ether (2:3) to give 992 mg (66%) of title C compound as an oil. A faster moving material (98 mg, 6.5%) was also isolated and identified by $^1H$ NMR as the cis double bond isomer.

D. [1β,2α(5Z),3α(1E,3α,4α),4β]-7-[3-(3-Hydroxy-4-phenyl -1-pentenyl)-7-oxabicyclo[2.2.1]hept-2-yl]-5-heptenoic acid, methyl ester (fast moving isomer A)

Title C compound (0.99 g, 2.49 mmol) and $CeCl_3.7.6-H_2O$ (0.954 g, 2.49 mmol) were dissolved in methanol (25 ml) and THF (2 ml). The solution was cooled in an ice bath and $NaBH_4$ (94.1 mg, 2.5 mmol) was added portionwise in 30 seconds. The ice bath was removed and the mixture was stirred 10 minutes, then poured into saturated $NH_4Cl$ solution (200 ml). The product was extracted into ethyl acetate (5×50 ml). The combined ethyl acetate extracts were dried ($MgSO_4$), filtered and freed of solvent in vacuo to give a viscous oil (0.953 g). This was chromatographed on silica gel (60 g) eluting with ether-pet ether (3:2) to give 616 mg of nearly clean faster moving isomer and 150 mg of (15%) of slower moving isomer ([1β,2α(5Z),3α(1E,3β),4β]-7-[3-(3-hydroxy-4-phenyl-1-pentenyl)-7-oxabicyclo[2.2.1]hept-2-yl]-5-heptenoic acid, methyl ester). TLC's silica gel; $Et_2O$-pet ether 3:2; vanillin $R_f$'s 0.35 and 0.25. The faster moving isomer A was rechromatographed eluting with the same solvent to give 605 mg (61%) of title D compound.

E. [1β,2α(5Z),3α(1E,3α,4α),4β]-7-[3-(3-Hydroxy-4-phenyl-1-pentenyl)-7-oxabicyclo[2.2.1]hept-2-yl]-5-heptenoic acid (fast moving isomer A) and [1β,2α(5Z),3α(1E,3α,4β),4β]-7-[3-(3-Hydroxy-4-phenyl-1-pentenyl)-7-oxabicyclo[2.2.1]hept-2-yl]-5-heptenoic acid (fast moving isomer B)

The title D methyl ester (599 mg, 1.5 mmol) was dissolved in THF (75 ml) and water (13.5 ml) and treated with 1N LiOH solution (15 ml). The mixture was stirred at room temperature in an argon atmosphere for 5 hours. The pH was adjusted to 3 by adding saturated oxalic acid solution and then the mixture was poured into water (450 ml). The product was extracted into ether (3×200 ml). The combined ether extracts were washed with water (3×200 ml) and saturated NaCl solution (1×200 ml), dried ($MgSO_4$), filtered and taken to dryness in vacuo leaving 544 mg (94%) of oil. This was chromatographed on silica gel 60 eluting with 3% MeOH in $CH_2Cl_2$ to give two isomers. The faster moving isomer A is [1β,2α(5Z),3α(1E,3α,4α), 4β]-7-[3-(3-hydroxy-4-phenyl-1-pentenyl)-7-oxabicyclo[2.2.-]hept-2-yl]-5-heptenoic acid and a slower moving isomer B (205 mg) is [1β,2α(5Z),3α(1E,3α,4β),4β]-7-[3-(3-hydroxy-4-phenyl-1-pentenyl)-7-oxabicyclo[2.2.1]hept-2-yl]-5-heptenoic acid. Mixed fractions accounted for an additional 112 mg-total yield 78%. TLC's silica gel, 5% MeOH in $CH_2Cl_2$, vanillin $R_f$'s 0.40 and 0.32.

Anal Calcd for $C_{24}H_{32}O_4$: C, 74.97; H, 8.39. Found: C, 74.84; H, 8.42.

TLC and spectral data indicates this sample in >95% faster moving material (Isomer A).

EXAMPLE 51

1β,2α(5Z),3α(1E,3β),4β]-7-[3-(3-Hydroxy-4-phenyl-1-pentenyl)-7-oxabicyclo[2.2.1]hept-2-yl]-5-heptenoic acid (slow moving isomer)

The slow moving isomer of methyl ester described in Examples 49 and 50 namely, [1β,2α(5Z),3α(1E,3β),4β]-7-[3-(3-hydroxy-2-yl]-5-heptenoic pentenyl)-7-oxabicyclo[2.2.1]hept-2-yl]-5-heptenoic acid, methyl ester (144 mg, 0.36 mmol) was dissolved in THF (18 ml) and water (3.2 mg). 1N LiOH solution (3.6 ml) was added and the mixture was stirred at room temperature in an argon atmosphere for 5 hours. A saturated solution of oxalic acid was added to adjust the pH to 3 and the solution was poured into water (150 ml). The product was extracted into ether (3×75 ml) and the combined ether extracts were washed with water (3×75 ml) and saturated NaCl solution (75 ml). The solution was dried (MgSO$_4$), filtered and the solvent was removed in vacuo to give the title product, 136 mg (98%). TLC-silica gel, 5% MeOH in CH$_2$Cl$_2$, vanillin R$_f$=0.22.

Anal Calcd for C$_{24}$H$_{32}$O$_4$: C, 74.94; H, 8.39. Found: C, 74.58; H, 8.36.

EXAMPLE 52

[1β,2α(5Z),3α(1E,3α),4β]-7-[3-[3-Hydroxy-4-(2-methylphenyl)-1-butenyl]-7-oxabicyclo[2.2.1]-hept-2-yl]-5-heptenoic acid (fast moving isomer)

A. 2-Oxo-3-(2-Methylphenyl)propyl dimethyl phosphonate

A solution of distilled dimethyl methylphosphonate (9.1 ml, 10.5 g, 77 mmol) in distilled THF (130 ml) was cooled to −78° in an argon atmosphere and treated dropwise in 30 minutes with a solution of 1.15N n-butyl lithium (70 ml, 80 mmol) in hexane. After addition was complete the mixture was stirred at −78° C. for 30 minutes. A solution of the methyl ester of o-tolylacetic acid (6.56 g, 40 mmol) in THF (7 ml) was added dropwise in 15 minutes. After stirring at −78° C. for 3.5 hours the cooling bath was removed and stirring was continued for 1 hour. The reaction was quenched by adding HOAc to pH 6. The solvent was removed in vacuo. Water (100 ml) was added to the residue and the product was extracted into CH$_2$Cl$_2$ (3×100 ml). The combined extracts were washed once with saturated NaHCO$_3$ solution and once with water, dried (MgSO$_4$) and freed of solvent in vacuo. The residue was distilled to give 3.8 g (37%) of the title compound, b.p. 133°–135°/0.1 mmHg.

B. [1β,2α(5Z),3α(1E,3α),4β]-7-[3-[3-Oxo-4-(2-methylphenyl)-1-butenyl]-7-oxabicyclo[2.2.1]hept-2-yl]-5-heptenoic acid, methyl ester Sodium hydride (201 mg of 50% in mineral oil, 4.18 mmol) was suspended in distilled dimethoxyethane (70 ml) in an argon atmosphere. A solution of title A phosphonate (1.46 g, 5.7 mmol) in DME (7 ml) was added. The mixture was stirred at room temperature 90 minutes. A solution of [1β,2α(5Z),3α,4β]-7-[3-formyl-7-oxabicyclo[2.2.1]hept-2-yl]-5-heptenoic acid, methyl ester (prepared as described in Example 5) (1.031 g, 3.8 mmol) in DME (5 ml) was added and the mixture was left stirring overnight at room temperature. The reaction was quenched by adding HOAc (0.5 ml). The solvent was removed in vacuo and ether and saturated NaHCO$_3$ solution were added to the residue. The layers were separated and the ether layer was washed with NaHCO$_3$ solution; dried (MgSO$_4$), and freed of solvent in vacuo leaving a yellow oil. This was chromatographed on silica gel 60 (110 g) eluting with ether-pet ether 1:2 to give 930 mg (61%) of title B compound which crystallized on standing. TLC-silica gel, Et$_2$O-P.E 1:1, U.V. +vanillin R$_f$0.33. Faster moving material (R$_f$=0.45) was also isolated (410 mg, 27%) and characterized as the cis double bond isomer.

C. [1β, 2α(5Z), 3α(1E,3α),4β]-7-[3-[3-Hydroxy-4-(2-methylphenyl)-1-butenyl]-7-oxabicyclo[2.2.1]hept-2-yl]-5-heptenoic acid, methyl ester (fast moving isomer)

Title B compound (930 mg, 2.33 mmol) and CeCl$_3$.7.6 H$_2$O (896 ml, 2.33 mmol) were dissolved in methanol (25 ml) and THF (4 ml). After cooling to 0°–5° C., NaBH$_4$ (88 mg, 2.33 mmol) was added portionwise in 30 sec. The ice bath was removed and the mixture was stirred 10 minutes, and then poured into saturated NH$_4$Cl solution (175 ml). The product was extracted into ethyl acetate (5×50 ml), dried (MgSO$_4$) and freed of solvent in vacuo leaving an oil. This was chromatographed on silica gel 60 (110 g), eluting with ether-pet ether 3:2 to give 479 mg (51%) title C fast moving isomer and 184 mg (20%) of slow moving isomer. TLC: silica gel, Et$_2$O-P.E 3:2, vanillin R$_f$=0.39 (FMI) and 0.21 (SMI).

D. [1β,2α(5Z),3α(1E,3α),4β]-7-[3-[3-Hydroxy-4-(2-methylphenyl)-1-butenyl]-7-oxabicyclo[2.2.1]hept-2-yl]-5-heptenoic acid (fast moving isomer)

The title C methyl ester (fast moving isomer) (479 mg, 1.2 mmol) was dissolved in THF (60 ml) and water (11 ml) in an argon atmosphere. Lithium hydroxide solution (1N, 12.0 ml) was added and the mixture was stirred at room temperature 6 hours. Saturated oxalic acid solution was added to adjust the pH to 3 and the mixture was then poured into water (450 ml). The product was extracted into ether (3×200 ml). The combined ether extracts were washed with water (3×200 ml) and saturated NaCl solution (1×200 ml), dried (MgSO$_4$) and freed of solvent in vacuo. The oil was purified by chromatography on silica gel 60 (50 g), eluting with 3% MeOH in CH$_2$Cl$_2$ to give the title product (296.5 mg, 64%). TLC-silica gel, 5% MeOH in CH$_2$Cl$_2$, vanillin R$_f$=0.24.

Anal Calcd for C$_{24}$H$_{32}$O$_4$: C, 74.97; H, 8.39. Found: C, 74.91; H, 8.63.

EXAMPLE 53

[1β,2α(5Z),3α(1E,3β),4β]-7-[3-[3-Hydroxy-4-(2-methylphenyl)-1-butenyl]-7-oxabicyclo[2.2.1]hept-2-yl]-5-heptenoic acid (slow moving isomer)

The slow moving isomer [1β,2α(5Z),3α(1E,3β),4β]-7-[3-[3-Hydroxy-4-(2-methylphenyl)-1-butenyl]-7-oxabicyclo2.2.1]hept-2-yl]-5-heptenoic acid, methyl ester (prepared as described in Example 52, part C), (184 mg, 0.46 mmol) was dissolved in THF (25 ml) and water (4 ml) in an argon atmosphere and treated with 1N LiOH solution (4.6 ml). The mixture was stirred at room temperature for 6.5 hours; the pH was then adjusted to 3 by adding a saturated solution of oxalic acid. The solution was poured into water (150 ml) and the product was extracted into ether (3×75 ml). The combined ether extracts were washed with water (3×75 ml) and saturated NaCl solution (75 ml), dried (MgSO$_4$) and freed of solvent in vacuo to give the title product, 165 mg (93%) as a viscous oil. TLC: silica gel, 5% MeOH in CH$_2$Cl$_2$, vanillin R$_f$=0.17.

Anal Calcd for C$_{24}$H$_{32}$O$_4$: C, 74.97; H, 8.39. Found: C, 74.91; H, 8.56.

EXAMPLE 54

[1β,2α(5Z),3α(1E,3α),4β]-7-[3-[3-Hydroxy-4-(3-methylphenyl)-1-butenyl]-7-oxabicyclo[2.2.1]-hept-2-yl]-5-heptenoic acid (fast moving isomer)

A. 2-Oxo-3-(3-methylphenyl)propyl dimethyl phosphonate

A solution of distilled dimethyl methylphosphonate (9.1 ml, 10.5 g, 77 mmol) in distilled THF (130 ml) was cooled to −78° C. in an argon atmosphere and treated dropwise in 30 minutes with a solution of 1.15N n-butyl lithium (70 ml, 80 mmol) in hexane. After addition was complete, the mixture was stirred at −78° C. for 30 minutes. A solution of the methyl ester of m-tolylacetic acid (6.56 g, 40 mmol) in 7 ml THF was then added dropwise over a period of 15 minutes. After stirring at −78° C. 3½ hours the cooling bath was removed and the mixture was stirred an additional 60 minutes. The reaction was quenched by adding acetic acid to pH 6. The solvent was removed in vacuo and water (70 ml) was added to the residue. The product was extracted into $CH_2Cl_2$ (3×100 ml). The combined extracts were washed once with water, dried ($MgSO_4$) and freed of solvent in vacuo. The residue was distilled in vacuo to give the title A phosphonate (5.6 g, 55%) boiling 133°–135°/0.1 mm.

B. [1β, 2α(5Z), 3α(1E,3α),4β]-7-[3-[3-Oxo-4-(3-methylphenyl)-1-butenyl]-7-oxabicyclo[2.2.1]hept-2-yl]-5-heptenoic acid, methyl ester Sodium hydride (201 mg of 50% in mineral oil, 4.18 mmol) was suspended in distilled dimethoxyethane in an argon atmosphere. A solution of title A phosphonate (1.46 g, 5.7 mmol) in DME (7 ml) was added. The mixture became nearly clear and then a fluffy solid began precipitating out. After stirring at room temperature 90 minutes a solution of [1β,2α(5Z),3α,4β]-7-[3-formyl-7-oxabicyclo[2.2.1]hept-2-yl]-5-heptenoic acid, methyl ester (1.031 g, 3.8 mmol) in DME (5 ml) was added. The mixture was left stirring overnight at room temperature then quenched by adding glacial HOAc (0.5 ml). The solvent was removed in vacuo. Ether and saturated $NaHCO_3$ solution were added to the residue. The layers were separated and the ether layer was washed once with $NaHCO_3$ solution, dried ($MgSO_4$), and freed of solvent in vacuo leaving a yellow oil. This was chromatographed on silica gel 60 (110 g) eluting with ether-pet ether 1:2 to give 1.009 g (67%) of title B compound as a colorless oil. TLC-silica gel, ether-pet ether 1:1, vanillin $R_f$=0.34. A faster moving material ($R_f$=0.42) was also isolated (262 mg, 17%) and identified as the cis double bond isomer.

C. [1β,2α(5Z),3α(1E,3α),4β]-7-[3-[3-Hydroxy-4-(3-methylphenyl)-1-butenyl]-7-oxabicyclo[2.2.1]hept-2-yl]-5-heptenoic acid, methyl ester Title B compound (1.005 g, 2.5 mmol) and $CeCl_3.7.6-H_2O$ (0.968 g, 2.5 mmol) were dissolved in methanol (25 ml) and THF (2 ml). The solution was cooled in an ice bath and $NaBH_4$ (95.5 mg, 2.5 mmol) was added portionwise in 30 seconds. The ice bath was removed and the mixture was stirred 8 minutes, then poured into saturated $NH_4Cl$ solution (200 ml). The product was extracted into ethyl acetate (5×50 ml), dried and freed of solvent in vacuo. The remaining oil was chromatographed on silica gel 60 (110 g) eluting with ether-pet ether (1:1 and then 3:2) to give 634 mg (63%) of fast moving isomer and 210 mg (21%) of slow moving isomer. TLC: silica gel, $Et_2O$-P.E 3:2, vanillin $R_f$=0.35 (FMI) and 0.15 (SMI).

D. [1β,2α(5Z),3α(1E,3α),4β]-7-[3-[3-Hydroxy-4-(3-methylphenyl)-1-butenyl]-7-oxabicyclo[2.2.1]hept-2-yl]-5-heptenoic acid (fast moving isomer)

The title C fast moving isomer of the methyl ester (634 mg, 1.59 mmol) was dissolved in distilled THF (75 ml) and water (14 ml) in an argon atmosphere. The solution was treated with 1N LiOH solution (15.9 ml) and stirred at room temperature 6 hours. A saturated solution of oxalic acid was added to pH 3 and the solution was poured into water (450 ml). The product was extracted into ether (3×200 ml). The combined ether extracts were washed with water (3×200 ml) and saturated NaCl solution (1×200 ml), dried ($MgSO_4$) and freed of solvent in vacuo leaving a colorless oil. This was chromatographed on silica gel 60 (50 g) eluting with 3% MeOH in $CH_2Cl_2$ to give the title product, 513 mg (84%) as a colorless oil. TLC: silica gel, 5% MeOH in $CH_2Cl_2$, vanillin $R_f$=0.27.

Anal Calcd for $C_{24}H_{32}O_4$: C, 74.97; H, 8.39. Found: C, 74.98; H, 8.42.

EXAMPLE 55

1β,2α(5Z),3α(1E,3β),4β]-7-[3-[3-Hydroxy-4-(3-methylphenyl)-1-butenyl]-7-oxabicyclo[2.2.1]hept-2-yl]-5-heptenoic acid (slow moving isomer)

The slow moving isomer of the methyl ester prepared in Example 54, Part C, that is [1β,2α(5Z),3α(-1E,3β),4β]-7-[3-[3-hydroxy-4-(3-methylphenyl)-1-butenyl]-7-oxabicyclo[2.2.1]-hept-2-yl]-5-heptenoic acid, methyl ester (210 mg, 0.53 mmol) was dissolved in THF (25 ml) and water (5 ml) in an argon atmosphere. Lithium hydroxide solution (1N, 5.3 ml) was added and the mixture was stirred at room temperature 6.5 hours. The pH was adjusted to 3 by adding saturated oxalic acid solution and then the solution was poured into water (150 ml). The product was extracted into ether (3×75 ml). The combined extracts were washed with water (3×75 ml) and saturated NaCl solution (75 ml), dried ($MgSO_4$) and freed of solvent in vacuo to give the title product as a colorless oil (191 mg, 94%). TLC-silica gel, 5% MeOH in $CH_2Cl$, vanillin $R_f$=0.18.

Anal Calcd for $C_{24}H_{32}O_4$: C, 74.97; H, 8.39. Found: C, 75.09; H, 8.39.

EXAMPLE 56

1β,2α(5Z),3α(1E,3α),4β]-7-[3-[3-Hydroxy-4-methyl-4-phenyl-1-pentenyl)-7-oxabicyclo[2.2.1]-hept-2-yl]-5-heptenoic acid (fast moving isomer)

A. 2-Oxo-3-methyl-3-phenylbutyl dimethyl phosphonate

Sodium hydride (374.4 mg of 50% in mineral oil, 7.8 mmol) was washed with freshly distilled THF (5 ml) and suspended in THF (78 ml). 2-Oxo-3-phenylbutyl dimethyl phosphonate (prepared as described in Example 49, Part B), (2.0 g, 7.8 mmol) was added dropwise at 0° C. The mixture was stirred one hour at room temperature then cooled to −78° C. and treated with a solution of n-BuLi in hexane (4.85 ml of 1.7M solution, 7.8 mmol). The reaction was stirred at −78° C. for 15 minutes and at 0° C. for 1 hour. Methyl iodide (1.5 ml, 24 mmol) was added and the mixture was stirred at 0° C. for 1 hour, then quenched by adding glacial acetic acid. The mixture was carefully poured into saturated $NaHCO_3$ solution and the product was extracted into ethyl acetate (3×150 ml). The combined extracts were washed with saturated $NaHCO_3$ solution and saturated NaCl solution, dried ($Na_2SO_4$) and freed of solvent in vacuo to give a brown oil. This was distilled by kugelrohr to give the title A phosphonate, 1.9 g (92%) boiling 170°/0.15 mm.

B. [1β,2α(5Z),3α(1E,3α),4β]-7-[3-(3-Oxo-4-methyl-4-phenyl-1-pentenyl)-7-oxabicyclo[2.2.1]hept-2-yl]-5-heptenoic acid, methyl ester Sodium hydride (201 mg of 50% in mineral oil, 4.18 mmol) was suspended in 70 ml distilled dimethoxyethane in an argon atmosphere. A solution of title A phosphonate (1.54 g, 5.7 mmol) in DME (7 ml) was added and the mixture was stirred at room temperature 90 minutes. [1β,2α(5Z),3α,4β]-7-[3-Formyl-7-oxabicyclo[2.2.1]hept-2-yl]-5-heptenoic acid, methyl ester (1.031 g, 3.8 mmol) in DME (5 ml) was added and the reaction mixture was left stirring overnight at room temperature. The reaction was quenched by adding glacial acetic acid (0.5 ml) and the solvent was removed in vacuo. Ether and saturated NaHCO$_3$ solution were added to the residue. The layers were separated and the ether layer was washed once with saturated NaHCO$_3$ solution, dried (MgSO$_4$) and freed of solvent in vacuo leaving a yellow oil. This was chromatographed on silica gel 60, eluting with ether-pet ether (2:5) to give title B compound (1.0 g, 64%) as an oil. TLC: silica gel, Et$_2$O-P.E. (1:1), vanillin R$_f$=0.48.

C. [1β,2α(5Z),3α(1E,3α),4β]-7-[3-[3-Hydroxy-4-methyl-4-phenyl-1-pentenyl]-7-oxabicyclo[2.2.1]hept-2-yl]-5-heptenoic acid, methyl ester (fast moving isomer)

The title B ketone (1.0 g, 2.43 mmol) and CeCl$_3$.7.6 H$_2$O (0.932 g, 2.43 mmol) were dissolved in MeOH (25 ml). The solution was cooled in an ice bath and treated portionwise in 30 sec. with NaBH$_4$ (92 mg, 2.43 mmol). The ice bath was removed and the mixture was stirred 8 minutes, then poured into sat'd NH$_4$Cl solution (200 ml). The product was extracted into EtOAc (5×50 ml), dried (MgSO$_4$) and freed of solvent in vacuo to give an oil. This was chromatographed on silica gel 60 (60 g), eluting with ether-pet ether 2:3 to give title C fast moving isomer (690 mg, 69%) and slow moving isomer (97 mg, 9.7%). TLC: silica gel, Et$_2$O-P.E. 3:2, vanillin R$_f$'s 0.46 (FMI) and 0.32 (SMI).

D. [1β,2α(5Z),3α(1E,3α),4β]-7-[3-[3-Hydroxy-4-methyl-4-phenyl-1-pentenyl]-7-oxabicyclo[2.2.1]hept-2-yl]-5-heptenoic acid (fast moving isomer)

The fast moving isomer of methyl ester (title C) (680 mg, 1.67 mmol) was dissolved in THF (75 ml) and water (15 ml). Lithium hydroxide solution (16.7 ml of 1N solution) was then added and the mixture was stirred at room temperature 7 hours. A saturated solution of oxalic acid was added to pH 3 and the solution was poured into water (450 ml). The product was extracted into ether (3×200 ml) and the combined extracts were washed with water (3×200 ml) and saturated NaCl solution (1×200 ml), dried (MgSO$_4$) and freed of solvent in vacuo. The oil was chromatographed on silica gel 60 (40 g) eluting with 3% MeOH in CH$_2$Cl$_2$ to give the title product (545 mg, 82%). TLC-silica gel, 5% MeOH in CH$_2$Cl$_2$, vanillin R$_f$=0.32.

Anal Calcd for C$_{24}$H$_{35}$O$_4$: C, 75.34; H, 8.60. Found: C, 75.07; H, 8.37.

EXAMPLE 57

[1β,2α(5Z),3α(1E,3β),4β]-7-[3-(3-Hydroxy-4-methyl-4-phenyl-1-pentenyl)-7-oxabicyclo[2.2.1]-hept-2-yl]-5-heptenoic acid (slow moving isomer)

The slow moving isomer of methyl ester prepared in Example 56, Part C, that is [1β,2α(5Z), 3α(1E,3β),4β]-7-[3-(3-hydroxy-4-methyl-4-phenyl-1-pentenyl)-7-oxabicyclo[2.2.1]hept-2-yl]-5-heptenoic acid, methyl ester (95 mg, 0.23 mmol) was dissolved in tetrahydrofuran (12 ml) and water (2 ml). Lithium hydroxide solution (2.3 ml of 1N) was added and the mixture was stirred at room temperature 6.5 hours. Saturated oxalic acid solution was added to pH 3 and the solution was poured into water (100 ml). The product was extracted into ether (3×50 ml). The combined ether extracts were washed with water (3×50 ml) and saturated NaCl solution (1×50 ml), dried (MgSO$_4$) and freed of solvent in vacuo to give the title product as an oil (91 mg, 99%). TLC: silica gel, 5% MeOH in CH$_2$Cl$_2$, vanillin R$_f$=0.2.

Anal Calcd for C$_{25}$H$_{34}$O$_4$: C, 75.34; H, 8.60. Found: C, 75.64; H, 8.44.

EXAMPLE 58

[1β,2α(5Z),3α(1E,3α),4β]-7-[3-[3-Hydroxy-3-(1-methylcyclohexyl)-1-propenyl]-7-oxabicyclo[2.2.1-]hept-2-yl]-5-heptenoic acid (fast moving isomer)

A. 2-Oxo-2-(1-methylcyclohexyl)dimethyl phosphonate n-BuLi (1.15M solution in hexane, 70 ml, 80 mmol) was added dropwise to a stirred solution of distilled dimethyl methylphosphonate (9.1 ml, 10.5 g, 77 mmol) in THF (130 ml) at −78° C. Stirring was continued for 30 minutes at −78° and then a solution of the methyl ester of 1-methyl-1-cyclohexanecarboxylic acid (6.24 g, 40 mmol) in THF (8 ml) was added dropwise over a period of 15 minutes. The mixture was stirred at −78° C. for 3.5 hours and then at room temperature for 2 hours. The reaction was quenched by addition of HOAc to pH ~6. The solvent was removed in vacuo and water (70 ml) was added to the residue. The product was extracted into CH$_2$Cl$_2$ (3×100 ml). The combined extracts were washed once with water, dried (MgSO$_4$) and freed of solvent in vacuo leaving an oil. This was distilled to give the title compound (6.0 g, 60.5%) boiling 120°–122°/0.2 mm.

B. [1β,2α(5Z),3α(1E,3α),4β]-7-[3-[3-Oxo-3-(1-methylcyclohexyl)-1-propenyl]-7-oxabicyclo[2.2.1]hept-2-yl]-5-heptenoic acid, methyl ester Sodium hydride (201 mg of 50% in mineral oil, 4.18 mmol) was suspended in distilled dimethoxyethane (70 ml) in an argon atmosphere and treated with a solution of title A phosphonate (1.42 g, 5.7 mmol) in DME (7 ml). The mixture was stirred at room temperature 90 minutes. A solution of [1β,2α(5Z),3α,4β]-7-[3-formyl-7-oxabicyclo[2.2.1]hept-2-yl]-5-heptenoic acid, methyl ester (1.031 g, 3.8 mmol) in DME (5 ml) was added and the mixture was left stirring overnight at room temperature. The reaction was quenched by adding glacial acetic acid (0.5 ml) and the solvent was removed in vacuo. Ether and saturated NaHCO$_3$ solution were added and the layers were separated. The ether layer was washed once with saturated NaHCO$_3$ solution, dried (MgSO$_4$), and freed of solvent in vacuo leaving a yellow oil. This was chromatographed on silica gel 60 (110 g), eluting with ether-pet ether 1:2 to give title B compound, 1.241 g as an oil.

TLC-silica gel, Et$_2$O-PE 1:1, vanillin R$_f$0.48. A faster moving material (50 mg, 3%) (R$_f$0.56) was also isolated and identified as the cis double bond isomer.

C. [1β, 2α(5Z),3α(1E,3α), 4β]-7-[3-[3-Hydroxy-3-(1-methylcyclohexyl)-1-propenyl]-7-oxabicyclo[2.2.1-]hept-2-yl]-5-heptenoic acid, methyl ester (fast moving isomer)

Title B compound (1.226 g, 3.1 mmol) and CeCl$_3$.7.6 H$_2$O (1.18 g, 3.1 mmol) were dissolved in methanol (30 ml) and THF (2 ml). The solution was cooled in an ice bath and sodium borohydride (117 mg, 3.1 mmol) was added portionwise over a period of 30 seconds. The ice bath was removed and the mixture was stirred 8 minutes, then poured into saturated NH$_4$Cl solution (200 ml). The product was extracted into EtOAc (5×50 ml), dried and freed of solvent in vacuo leaving an oil (1.22 g). This was chromatographed on silica gel (80 g) eluting with ether-pet ether (1:1) to give 930 mg of material enriched in title C fast moving isomer and 142 mg (12%) of slow moving isomer. TLC-silica gel, Et$_2$O-PE 3:2, vanillin R$_f$=0.41 (FMI) and 0.2 (SMI). The fast moving isomer was rechromatographed on silica gel 60 eluting with 10% ethyl acetate in benzene to give clean title C compound (602 mg, 50%).

D. [1β,2α(5Z),3α(1E,3α),4β]-7-[3-[3-Hydroxy-3-(1-methylcyclohexyl)-1-propenyl]-7-oxabicyclo[2.2.1]hept-2-yl]-5-heptenoic acid (fast moving isomer)

The title C methyl ester (fast moving isomer, 602 mg, 1.54 mmol) was dissolved in THF (75 ml) and water (14 ml) in an argon atmosphere and treated with 1N LiOH solution (15.4 ml). The mixture was stirred at room temperature 6.5 hours. The pH was then adjusted to 3 by adding saturated oxalic acid solution and the solution was poured into water (450 ml). The product was extracted into ether (3×200 ml). The combined ether extracts were washed with water (3×200 ml) and saturated NaCl solution (1×200 ml), dried and freed of solvent in vacuo leaving 574 mg of oil. This was purified by chromatography on silic gel 60 (40 g), eluting with 3% MeOH in CH$_2$Cl$_2$ to give title product (479 mg, 83%) as a colorless oil. TLC:silica gel, 5% MeOH in CH$_2$Cl$_2$, vanillin R$_f$=0.56.

Anal Calcd for C$_{23}$H$_{36}$O$_4$: C, 73.37; H, 9.64. Found: C, 73.06; H, 9.70.

EXAMPLE 59

[1β,2α(5Z),3α(1E,3β),4β]-7-[3-[3-Hydroxy-3-(1-methylcyclohexyl)-1-propenyl]-7-oxabicyclo[2.2.1]-hept-2-yl]-5-heptenoic acid (slow moving isomer)

The slow moving methyl ester prepared in Example 58, Part C, that is [1β,2α(5Z),3α(1E, 3β),4β]-7-[3-[3-hydroxy-3-(1-methylcyclohexyl)-1-propenyl]-7-oxabicyclo[2.2.1]hept-2-yl]-5-heptenoic acid, methyl ester (142 mg, 0.36 mmol) was dissolved in THF (18 ml) and water (3.2 ml) in an argon atmosphere. The solution was treated with 1N LiOH solution (3:6 ml) and stirred at room temperature 6.5 hours. A saturated solution of oxalic acid was added to pH 3 and the mixture was poured into water (150 ml). The product was extracted into ether (3×75 ml). The combined ether extracts were washed with water (3×75 ml) and saturated NaCl solution (1×75 ml), dried (MgSO$_4$) and freed of solvent in vacuo leaving 132 mg of oil. This was chromatographed on silica gel 60 (15 g) eluting with 3% MeOH in CH$_2$Cl to give the title product (slow moving isomer), (97mg, 72%). TLC:silica gel, 5% MeOH in CH$_2$Cl$_2$, vanillin R$_f$=0.18.

Anal Calcd for C$_{23}$H$_{35}$O$_4$: C, 73.37; H, 9.64. Found: C, 73.24; H, 9.67.

EXAMPLE 60

[1β,2α(5Z),3α(1E,3α),4β]-7-[3-[3-Hydroxy-4-(4-methylphenyl)-1-butenyl]-7-oxabicyclo[2.2.1]hept-2-yl]-5-heptenoic acid (fast moving isomer)

A. 2-Oxo-3-(4-methylphenyl)propyl dimethyl phosphonate

A solution of distilled dimethyl methylphosphonate (5.6 ml, 6.44 g, 47 mmol) in dist. THF (80 ml) was cooled to −78° C. in an argon atmosphere and treated dropwise in 30 minutes with a solution of 1.65M n-butyl lithium in hexane (30 ml, 49 mmol). After addition was complete, the mixture was stirred at −78° for 30 minutes. A solution of the methyl ester of p-tolylacetic acid (4.025 g, 24.5 mmol) in 5 ml THF was added dropwise in 15 minutes. After stirring at −78° C. for 3.5 hours the cooling bath was removed and the mixture was stirred an additional 60 minutes. The reaction was quenched by adding acetic acid to pH 6. The solvent was removed in vacuo and water(75 ml) was added to the residue. The product was extracted into CH$_2$Cl$_2$ (3×75 ml). The combined extracts were washed once with saturated NaHCO$_3$ solution (75 ml) and once with water (75 ml), dried (MgSO$_4$) and freed of solvent in vacuo leaving an oil. This was distilled in vacuo to give the title phosphonate (3.06 g, 49%) boiling 132°-134°/0.1 mm.

B. [1β,2α(5Z),3β(1E,3α),4β]-7-[3-[3-Oxo-4-(4-methylphenyl)-1-butenyl]-7-oxabicyclo[2.2.1]hept-2-yl]-5-heptenoic acid, methyl ester Sodium hydride (201 mg of 50% in mineral oil, 4.18 mmol) was suspended in distilled dimethoxyethane (70 ml) in an argon atmosphere. A solution of title A phosphonate (1.46 g, 5.7 mmol) in DME (7 ml) was added. A fluffy solid precipitated out. After stirring at room temperature 90 minutes a solution of [1β,2α(5Z),3α, 4β]-7-[3-formyl-7-oxabicyclo[2.2.1]hept-2-yl]-5-heptenoic acid, methyl ester, prepared as described in Example 5, (1.03 g, 3.8 mmol) in DME (5 ml) was added. The mixture was left stirring overnight at room temperature, then quenched by adding glacial HOAc (0.5 ml). The solvent was removed in vacuo. Ether and saturated NaHCO$_3$ solution were added to the residue. The layers were separated and the organic layer was washed once with NaHCO$_3$ solution, dried (MgSO$_4$) and freed of solvent in vacuo to give material which crystallized on standing. This was chromatographed on silica gel 60 eluting with ether-pet ether 1:3 to give 1.064 g (70%) of title B compound which crystallized. TLC:silica gel, ether-pet ether 1:1, vanillin R$_f$=0.36. A faster moving material (R$_f$=0.43) was also isolated (228 mg, 15%) and identified as the cis double bond isomer.

C. [1β,2α(5Z),3α(1E,3α),4β]-7-[3-[3-Hydroxy-4-(4-methylphenyl)-1-butenyl]-7-oxabicyclo[2.2.1]hept-2-yl]-5-heptenoic acid, methyl ester Title B compound (1.06 g, 2.66 mmol) and CeCl$_3$.7.6 H$_2$O (1.02 g, 2.66 mmol) were dissolved in methanol (25 ml) and THF (2 ml). The solution was cooled in an ice bath and NaBH$_4$ (101 mg, 2.66 mmol) was added portionwise in 30 seconds. The cooling bath was removed and the mixture was stirred 10 minutes, then poured into saturated NH$_4$Cl solution (175 ml). The product was extracted into ethyl acetate (5×50 ml), dried (MgSO$_4$), and freed of solvent in vacuo leaving an oil. This was chromatographed on silica gel (100 g) eluting with Et$_2$O-P.E 3:2 to give 602 mg (57%) of title C compound (fast moving isomer) and 185 mg (17%) of slow moving isomer. TLC:silica gel, Et$_2$O-P.E 3:2, vanillin R$_f$=0.35 (FMI) and 0.12 (SMI).

D. [1β,2α(5Z),3α(1E,3α),4β)-7-[3-[3-Hydroxy-4-(4-methylphenyl)-1-butenyl]-7-oxabicyclo[2.2.1]hept-2-yl]-5-heptenoic acid (fast moving isomer)

The fast moving isomer of methyl ester (title C) (602 mg, 1.5 mmol) was dissolved in THF (75 ml) and water (14 ml) in an argon atmosphere. The solution was treated with 1N LiOH solution (15 ml) and stirred at room temperature 7 hours. Saturated oxalic acid solution was added to pH 3 and the solution was poured into water (450 ml). The product was extracted into ether (3×200 ml). The combined ether extracts were washed with water (3×200 ml) and saturated NaCl solution (1×200 ml), dried (MgSO$_4$) and freed of solvent in vacuo. The remaining oil was chromatographed on silica gel 60 (50 g) eluting with 3% MeOH in CH$_2$Cl$_2$ to give clean title product (416 mg, 72%) as a colorless oil.

TLC:silica gel, 5% MeOH in CH$_2$Cl$_2$, vanillin R$_f$=0.30. Anal Calcd for C$_{24}$H$_{32}$O$_4$ C, 74.97; H, 8.39. Found: C, 75.08; H, 8.48.

EXAMPLE 61

[1β,2α(5Z),3α(1E,3β), 4β]-7-[3-[3-Hydroxy-4-(4-methylphenyl)-1-butenyl]-7-oxabicyclo[2.2.1]hept-2-yl]-5-heptenoic acid (slow moving isomer)

The slow moving isomer of methyl ester, described in Example 60 part B,(185 mg, 0.46 mmol) was dissolved in THF (25 ml) and water (4 ml) in an argon atmosphere. 1N LiOH solution (4.6 ml) was added and the mixture was stirred at room temperature 7 hours. The pH was adjusted to 3 by adding saturated oxalic acid solution and the solution was then poured into water (150 ml). The product was extracted into ether (3×75 ml). The combined extracts were washed with water (3×75 ml) and saturated NaCl solution (75 ml), dried (MgSO$_4$) and freed of solvent in vacuo to give the title product as a colorless oil (177 mg, 99%). TLC:silica gel, 5% MeOH in CH$_2$Cl$_2$, vanillin R$_f$=0.23.

Anal Calcd for C$_{24}$H$_{32}$O$_4$: C, 74.97; H, 8.39. Found: C, 74.80; H, 8.08.

EXAMPLE 62

[1β,2α(5Z),3α(1E,3α,4α),4β]-7-[3-(3-Hydroxy-4-phenyl-1-hexenyl)-7-oxabicyclo[2.2.1]hept-2-yl]-5-heptenoic acid (fast moving isomer)

A. 2-Oxo-3-phenylpentyl dimethyl phosphonate

A solution of distilled dimethyl methyl-phosphonate (12.8 ml, 14.75 g, 108 mmol) in distilled THF (180 ml) was cooled to −78° C. in an argon atmosphere. While stirring, a solution of n-butyl lithium in hexane (1.65M, 68 ml, 112.4 mmol) was added dropwise over a period of 30 minutes. The mixture was stirred at −78° for an additional 30 minutes and then treated dropwise in 15 minutes with a solution of the methyl ester of 2-phenylbutyric acid (10.0 g, 56.2 mmol) in THF (15 ml). Stirring at −78° C. was continued for 3.5 hours. The cooling bath was then removed and after 75 minutes glacial acetic acid was added to pH 6. Most of the solvent was then removed in vacuo and water (100 ml) was added. The product was extracted into CH$_2$Cl$_2$ (3×125 ml). The combined extracts were washed with saturated NaHCO$_3$ solution (1×100 ml) and water (1×100 ml), dried (MgSO$_4$) and freed of solvent in vacuo. The title phosphonate was distilled giving 10.5 g (69%) boiling 134°–136°/0.1 mm.

B. [1β,2α(5Z),3α(1E,3α,4α),4β]-7-[3-[3-Oxo-4-phenyl-1-hexenyl)-7-oxabicyclo-[2.2.1]hept-2-yl]-5-heptenoic acid, methyl ester Sodium hydride (50% in mineral oil, 201 mg, 4.18 mmol) was suspended in distilled dimethoxyethane (70 ml) in an argon atmosphere. A solution of title A phosphonate (1.54 g, 5.7 mmol) in DME (7 ml) was added. After stirring at room temperature for 90 minutes a solution of [1β,2α(5Z),3α,4β]-7-[3-formyl-7-oxabicyclo[2.2.1]hept-2-yl]-5-heptenoic acid, methyl ester (1.03 g, 3.8 mmol) in DME (5 ml) was added. The mixture was stirred overnight at room temperature and then quenched by adding glacial acetic acid (0.5 ml). The solvent was removed in vacuo. Ether and saturated NaHCO$_3$ solution were added to the residue and the layers were separated. The ether layer was washed once with saturated NaHCO$_3$ solution, dried (MgSO$_4$) and freed of solvent in vacuo leaving an oil. This was purified by HPLC followed by chromatography on 100 g silica gel 60, eluting with ether-pet ether (1:3) to give 1.130 g (72%) of title compound as an oil. TLC: silica gel, Et$_2$O-P.E 1:1, UV and vanillin R$_f$=0.43.

C. [1β,2α(5Z),3α(1E,3α,4α),4β]-7-[3-[3-Hydroxy-4-phenyl-1-hexenyl]-7-oxabicyclo-[2.2.1]hept-2-yl]-5-heptenoic acid, methyl ester Title B compound (1.125 g, 2.73 mmol) and CeCl$_3$.7.6 H$_2$O (1.047 g, 2.73 mmol) were dissolved in methanol (25 ml) in an argon atmosphere. The solution was cooled in an ice bath and NaBH$_4$ (104 mg, 2.73 mmol) was added portionwise in 20 seconds. The cooling bath was removed and after stirring 8 minutes the mixture was poured into saturated NH$_4$Cl solution (175 ml). The product was extracted into ethyl acetate (5×50 ml), dried (MgSO$_4$) and freed of solvent in vacuo. The remaining oil was chromatographed on silica gel 60 (100 g) eluting with ether-pet ether (55:45) to give title C product fast moving isomer) 660 mg, 58%, and slow moving isomer (186 mg, 16.5%) TLC: silica gel, Et$_2$O-P.E 3:2, vanillin R$_f$=0.51 (fast moving isomer) and 0.24 (slow moving isomer).

D. [1β,2α(5Z),3α(1E,3α,4β),4β]-7-[3-(3-Hydroxy-4-phenyl-1-hexenyl)-7-oxabicyclo-[2.2.1]hept-2-yl]-5-heptenoic acid (fast moving isomer)

The fast moving isomer from Part C (655 mg, 1.58 mmol) was dissolved in THF (75 ml) and water (14 ml) in an argon atmosphere and treated with 1N LiOH solution (15.8 ml). The mixture was stirred at room temperature 6.5 hours and then acidified to pH 3 with saturated oxalic acid solution. After pouring into water (450 ml), the product was extracted into ether (3×200 ml). The combined extracts were washed with water (3×200 ml) and saturated NaCl solution (200 ml), dried (MgSO$_4$) and freed of solvent in vacuo. The remaining oil showed 2 major spots on TLC:silica gel, 5% MeOH/CH$_2$CL$_2$, vanillin R$_f$=0.49 (fast moving isomer A) and R$_f$=0.40 (fast moving isomer B). This was chromatographed on silica gel 60 (80 g) eluting with 3% MeOH in CH$_2$Cl$_2$ to give 3 pools—238 mg greatly enriched in the title isomer A, 114 mg mixture and 194 mg enriched in isomer B. (Total recovery 546 mg, 86.7%). The title isomer A enriched pool was rechromatographed on silica gel 60 (40 g), eluting with 2% MeOH in CH$_2$Cl$_2$ to give 180.1 mg of title isomer A appearing clean on TLC.

Anal Calcd for C$_{25}$H$_{34}$O$_4$: C, 75.34; H, 8.60. Found: C, 75.53; H, 8.61.

Material became a waxy solid on standing.

EXAMPLE 63

[1β,2α(5Z),3α(1E,3α,4β),4β-7-[3-(3-Hydroxy-4-phenyl-1-hexenyl)-7-oxabicyclo[2.2.1]hept-2-yl]-5-heptenoic acid (fast moving isomer B)

The pool (194 mg) described in Example 62 Part D as being enriched in isomer B was rechromatographed on silica gel 60 (30 g), eluting with 2.5% MeOH in CH$_2$CL$_2$ to give the title isomer, 95.4 mg (fast moving isomer B). TLC indicates this is >95% pure with the contaminant being isomer A (Example 62). TLC:silica gel, 5% MeOH/CH$_2$Cl$_2$ vanillin R$_f$=0.40, trace at 0.49 (A). Anal Calcd for C$_{25}$H$_{34}$O$_4$ : C, 75.34; H, 8.60. Found: C, 75.28; H, 8.36.

EXAMPLE 64

[1β,2α(5Z),3α(1E,3β),4β]-7-[3-(3-Hydroxy-4-phenyl-heptenyl)-7-oxabicyclo[2.2.1]hept-2-yl]-5-heptenoic acid (slow moving isomer)

The slow moving isomer described in Example 62, Part C (182 mg, 0.44 mmol) was dissolved in THF (25 ml) and water (4 ml) in an argon atmosphere and treated with 1N LiOH solution (4.4 ml). After stirring at room temperature 7 hours the pH was adjusted to 3 by adding saturated oxalic acid solution. The mixture was poured into water (150 ml) and extracted with ether (3×75 ml). The combined ether extracts were washed with water (3×75 ml) and saturated NaCl solution (75 ml), dried MgSO$_4$) and freed of solvent in vacuo leaving 172 mg oil. TLC:silica gel, 5% MeOH/CH$_2$Cl$_2$, vanillin showed a major spot R$_f$=0.34 (Isomer B) and a much smaller spot R$_f$=0.42 (Isomer A Example 62). The oil was chromatographed on silica gel 60 (30 g) eluting with 3% MeOH in CH$_2$Cl$_2$, to give the title product (100.6 mg, 57%) as a waxy solid. TLC:silica gel, 7% MeOH in CH$_2$Cl$_2$, vanillin R$_f$=0.34 (B), small amount R$_f$=0.42 (Isomer A). The sample is estimated to be 95% isomer B. Also obtained from the column was 26 mg rich in Isomer A and 21 mg of mixture (greater percentage is B).

Anal Calcd for C$_{25}$H$_{34}$O$_4$: C, 75.34; H, 8.60. Found: C, 75.37; H, 8.50.

What is claimed is:

1. A method of inhibiting bronchoconstriction, which comprises administering to the circulatory system of a mammalian host an effective amount of a compound having the structural formula

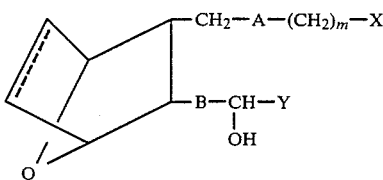

and including all stereoisomers thereof; wherein
A and B may be the same or different and A is CH=CH or (CH$_2$)$_2$, B is CH=CH, C≡C, or (CH$_2$)$_2$; m is 1 to 8;
X is OH;

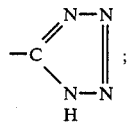

CO$_2$R$^1$ wherein R$^1$ is H or lower alkyl; or

wherein Z is H, lower alkyl, or aryl, SO$_2$—Q (wherein Q is lower alkyl or aryl),

or OR$^2$ wherein R$^2$ is H;
Y is substituted alkyl (wherein the substituent is halo, lower alkoxy, alkyl-aryl, haloalkyl, cycloalkyl or alkylcycloalkyl); aryl-lower alkyl; alkenyl containing 3 to 6 carbons; alkynyl containing 3 to 6 carbons; aryl (which may be unsubstituted or substituted with lower alkyl, halogen or lower alkoxy); cycloalkyl; substituted cycloalkyl; cycloalkylalkyl; substituted cycloalkylalkyl; or phenoxymethyl;
wherein alkyl or lower alkyl by itself or as part of another group contains 1 to 12 carbons, cycloalkyl by itself or as part of another group contains 3 to 12 carbons in the ring portion, aryl by itself or as part of another group refers to a monocyclic or bicyclic aromatic ring which contains 6 to 10 carbons in the ring portion, and the cycloalkyl group by itself or as part of another group may be substituted with 1 or 2 halogens, 1 or 2 lower alkyl groups or lower alkoxy groups (the above substituents not being adjacent to sterically hindered groups);
and ~~~~ represents a single bond or double bond, with the proviso that where ~~~~ represents a double bond, A is CH=CH and B is CH=CH or (CH$_2$)$_2$ and Y is other than alkenyl or alkynyl, or a pharmaceutically acceptable salt thereof.

2. The method as defined in claim 1 wherein X in said compound is

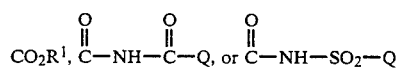

and wherein Q is phenyl or lower alkyl.

3. The method as defined in claim 1 wherein Y in said compound is phenyl, phenyl-alkyl, cycloalkyl or cycloalkyl-alkyl.

4. The method as defined in claim 1 wherein Y is

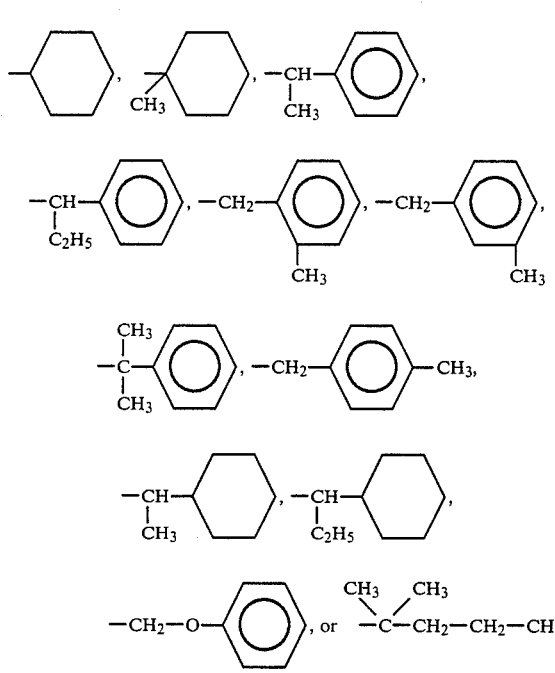

5. The method as defined in claim 1 wherein said compound has the name [1β,2β(5Z),3α(1E,3S*),4β[-7-

[3-(3-cyclohexyl-3-hydroxy-1-propenyl)-7-oxabicyclo[2.2.1]hept-2-yl]-5-heptenoic acid or [1β,2β(5Z),3α(-1E,3R*),4β]-7-[3-(3-cyclohexyl-3-hydroxy-1-propenyl)-7-oxabicyclo[2.2.1]hept-2-yl]-5-heptenoic acid or methyl esters of each.

6. The method as defined in claim 1 wherein said compound has the name [1β,2β(5Z),3α(1E,3S*),4β]-7-[3-(3-hydroxy-4,4-dimethyl-1-octenyl)-7-oxabicyclo[2.2.1]hept-2-yl]-5-heptenoic acid or [1β,2β(5Z),3α(-1E,3R*),4β]- 7-[3-(3-hydroxy-4,4-dimethyl-1-octenyl)-7-oxabicyclo[2.2.1]hept-2-yl]-5-heptenoic acid or methyl esters of each.

7. The method as defined in claim 1 wherein said compound has the name [1β,2β(5Z),3α(1E,3S*),4β]-7-[3-(3-hydroxy-4-phenyl-1-butenyl)-7-oxabicyclo[2.2.1-]hept-2-yl]-5-heptenoic acid or [1β,2β(5Z),3α(-1E,3R*),4β]-7-[3-(3-hydroxy-4-phenyl-1-butenyl)-7-oxabicyclo[2.2.1]hept-2-yl]-5-heptenoic acid or methyl esters of each.

8. The method as defined in claim 1 wherein said compound has the name [1β,2α(5Z),3α(1E,3S*),4β]-7-[3-(3-cyclohexyl-3-hydroxy-1-propenyl)-7-oxabicyclo[2.2.1]hept-2-yl]-5-heptenoic acid.

9. The method as defined in claim 1 wherein said compound has the name [1β,2β(5Z),3α(1E,3S*),4β]-7-[3-(4-cyclohexyl-3-hydroxy-1-butenyl)-7-oxabicyclo[2.2.1]hept-2-yl-5-heptenoic acid or [1β,2β(5Z),3α(-1E,3R*),4β]-7-[3-(4-cyclohexyl-3-hydroxy-1-butenyl)-7-oxabicyclo[2.2.1]hept-2-yl]-5-heptenoic acid or methyl esters of each.

10. The method as defined in claim 1 wherein said compound has the name [1β,2α(5Z,3α(1E,3S*),4β]-7-[3-(3-hydroxy-4-phenyl-1-butenyl)-7-oxabicyclo[2.2.1-]hept-2-yll-5-heptenoic acid or its methyl ester.

11. The method as defined in claim 1 wherein said compound has the name [1β,2α(5Z),3α(1E,3α,4α),4β]-7-[3-(3-hydroxy-4-phenyl-1-pentenyl)-7-oxabicyclo[2.2.1]hept-2-yl]-5-heptenoic acid; [1β,2α(5Z),3α(-1E,3α,4β), 4β]-7-[3-(3-hydroxy-4-phenyl-1-pentenyl)-7-oxabicyclo[2.2.1]hept-2-yl]-5-heptenoic acid; or [1β,2α(5Z),3α(1E,3β),4β]-7-oxabicyclo[2.2.1]hept-2-yl-5-heptenoic acid or [1β,2α(5Z),3α(1E,3β),4β]-7-[3-(3-hydroxy-4-phenyl-1-pentenyl)-7-oxabicyclo[2.2.1-]hept-2-yl]-5-heptenoic acid or methyl esters of each.

12. The method as defined in claim 1 wherein said compound has the name [1β,2α(5Z),3α(1E,3α), 4β]-7-[3-[3-hydroxy-4-(2-methylphenyl)-1-butenyl]-7-oxabicyclo[2.2.1]hept-2-yl]-5-heptenoic acid or [1β,2α(5Z),3α(1E,3β),4β]-7-[3-[3-hydroxy-4-(2-methylphenyl)-1-butenyl]-7-oxabicyclo [2.2.1]hept-2-yl]-5-heptenoic acid or methyl esters of each.

13. The method as defined in claim 1 wherein said compound has the name [1β,2α(5Z),3α(1E,3α),4β]-7-[3-[3-hydroxy-4-(3-methylphenyl)-1-butenyl]-7-oxabicyclo[2.2.1]hept-2-yl-5-heptenoic acid or [1β,2α(5Z),3α(1E,3β),4β]-7-[3-[3-hydroxy-4-(3-methylphenyl)-1-butenyl]-7-oxabicyclo [2.2.1]hept-2-yl]-5-heptenoic acid or methyl esters of each.

14. The method as defined in claim 1 wherein said compound has the name 1β,2α(5Z), 3α(1E, 3α),4β]-7-[3-3-hydroxy-4-methyl-4-phenyl-1-pentenyl)-7-oxabicyclo 2.2.1 ]hept-2-yl]-5-heptenoic acid or 1β,2α(5Z),3α(-1E,3β),4β]-7-[3-3-hydroxy-4-methyl-4-phenyl-1-pentenyl)-7-oxabicyclo [2.2.1]hept-2-yl-5-heptenoic acid esters of each.

15. The method as defined in claim 1 wherein said compound has the name [1β,2α(5Z),3α(1E, 3α),4β-7-[3-[3-hydroxy-3-(1-methylcyclohexyl)-1-propenyl-7-oxabicyclo [2.2.1 ]hept-2 -yl-5-heptenoic acid or [1β,2α(5Z),3α(1E,3β),4β]-7-[3-[3-hydroxy-3-(1-methyl-yl-cyclohexyl)-1-propenyl-]7-oxabicyclo[2.2.1 ]hept-2-yl]-5-heptenoic acid or methyl esters of each.

16. The method as defined in claim 1 wherein said compound has the name [1β,2α(5Z),3α(1E,3α),4β]-7-[3-[3-hydroxy-4-(4-methylphenyl)-1-butenyl]-7-oxabicyclo[2.2.1]hept-2-yl]-5-heptenoic acid or [1β,2α(5Z),3α(1E,3β),4β]-7-[3-[3-hydroxy-4-methylphenyl)-1-butenyl]-7-oxabicyclo [2.2.1]hept-2-yl-5-heptenoic acid or methyl esters of each.

17. The method as defined in claim 1 wherein said compound has the name [1β,2α(5Z),3α(1E,3α,4α),4β]-7-[3-3-hydroxy-4-phenyl-1-hexenyl-7-oxabicyclo [2.2.1]hept-2-yl]-5-heptenoic acid; or [1β,2α(5Z),3α(-1E,3α,4β),4β]-7-[3-3-hydroxy-4-phenyl-1-hexenyl)-7-oxabicyclo [2.2.1]hept-2-yl]-5-heptenoic acid or [1β,2α(5Z),3α(1E,3β),4β]-7-[3-3-hydroxy-4-phenyl-1-heptenyl)-7-oxabicyclo[2.2.1]hept-2-yl]-5-heptenoic acid or methyl esters of each.

18. The method as defined in claim 1 wherein said compound is administered in an amount within the range of from about 1 to about 100 mg/kg.

19. A composition for inhibiting bronchoconstriction comprising an effective amount of a compound having the structural formula

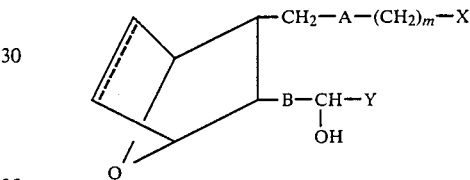

and including all stereoisomers thereof; wherein
A and B may be the same or different and A is CH=CH or (CH$_2$)$_2$, B is CH=CH, C≡C, or (CH$_2$)$_2$; m is 1 to 8;
X is OH;

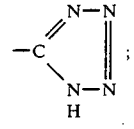

CO$_2$R$^1$ wherein R$^1$ is H or lower alkyl; or

wherein Z is H, lower alkyl, or aryl, SO$_2$—Q (wherein Q is lower alkyl or aryl),

or OR$^2$ wherein R$^2$ is H;
Y is aryl-lower alkyl; alkenyl, alkynyl cycloalkyl; substituted cycloalkyl; cycloalkylalkyl, substituted cycloalkylalkyl, or phenoxymethyl;
wherein alkyl or lower alkyl by itself or as part of another group contains 1 to 12 carbons, cycloalkyl by itself or as part of another group contains 3 to 12 carbons in the ring portion, aryl by itself or as part of another group refers to a monocyclic or bicyclic armomatic ring which contains 6 to 10 carbons in the ring potion, and the cycloalkyl group by itself or as part of another group may be substituted with 1 or 2 halogens, 1 or 2 lower alkyl groups or lower alkoxy groups (the above substituents not being adjacent to sterically hindered groups);

and ⚊⚊ represents a single bond or double bond with the proviso that where ⚊⚊ represents a double bond, A is CH=CH and B is CH=CH or (CH$_2$)$_2$ and Y is other than alkenyl or alkynyl, or a pharmaceutically acceptable salt thereof, and a pharmaceutically accpetable carrier therefor.

20. A method of inhibiting bronchoconstriction associated with asthma, which comprises administering to a mammalian host an effective amount of a compound having the structural formula

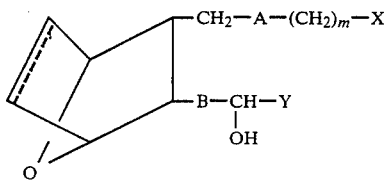

and including all stereoisomers thereof; wherein

A and B may be the same or different and A is CH=CH or (CH$_2$)$_2$, B is CH=CH, C≡C, or (CH$_2$)$_2$; m is 1 to 8;

X is OH;

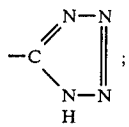

CO$_2$R$^1$ wherein R$^1$ is H or lower alkyl; or

wherein Z is H, lower alkyl, or aryl, SO$_2$—Q (wherein Q is lower alkyl or aryl),

or OR$^2$ wherein R$^2$ is H;

Y is substituted alkyl (wherein the substituent is halo, lower alkoxy, alkyl-aryl, haloalkyl, cycloalkyl or alkylcycloalkyl) aryl-lower alkyl; alkenyl containing 3 to 6 carbons; alkynyl containing 3 to 6 carbons; aryl (which may be unsubstituted or substituted with lower alkyl, halogen or lower alkoxy), cycloalkyl; substituted cycloalkyl; cycloalkylalkyl, substituted cycloalkylalkyl, or phenoxymethyl;

wherein alkyl or lower alkyl by itself or as part of another group contains 1 to 12 carbons, cycloalkyl by itself or as part of another group contains 3 to 12 carbons in the ring portion, aryl by itself or as part of another group refers to a monocyclic or bycyclic aromatic ring which contains 6 to 10 carbons in the ring portion, and the cycloalkyl group by itself or as part of another group may be substituted with 1 or 2 halogens, 1 or 2 lower alkyl groups or lower alkoxy groups (the above substituents not being adjacent to sterically hindered groups);

and ⚊⚊ represents a single bond or double bond with the proviso that where ⚊⚊ represents a double bond, A is CH=CH and B is CH=CH or (CH$_2$)$_2$ and Y is other than alkenyl or alkynyl, or a pharmaceutically acceptable salt thereof.

* * * * *

UNITED STATES PATENT AND TRADEMARK OFFICE
CERTIFICATE OF CORRECTION

PATENT NO. : 4,537,904   Page 1 of 2
DATED : August 27, 1985
INVENTOR(S) : David L. Snitman et al.

It is certified that error appears in the above-identified patent and that said Letters Patent is hereby corrected as shown below:

Column 4, line 25, after the last structure insert a period (.).
At the bottom of Column 4, " $\xrightarrow[\text{Pd/C}]{H_2}$ (A is $(CH_2)_2$ or -CH=CH-) " should read -- $\xrightarrow[\text{Pd/C}]{H_2}$ (A is $(CH_2)_2$ or -CH=CH-) --.

Column 13, line 55, delete "A = $-(CH_2)_2-$ or -CH=CH-".
Column 15, the third structure should read -- 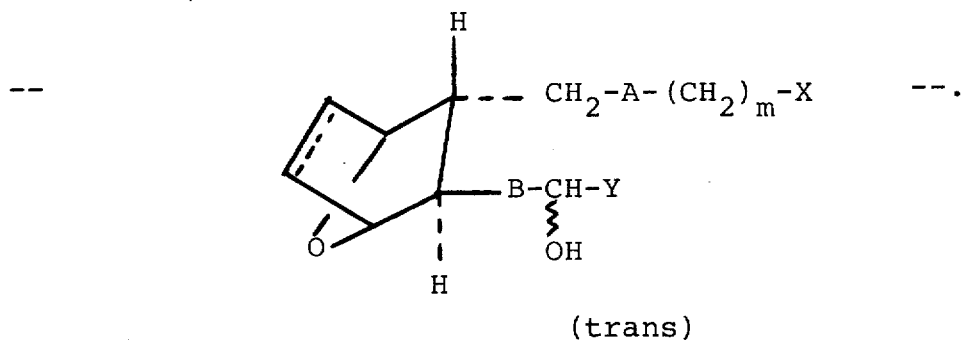 --.

(trans)

Column 32, line 59, "solutibn" should read --solution--.
Column 34, line 25, "oxy--butenyl" should read --oxy-1-butenyl--.
Column 38, line 49, after "tion" insert a period (.).
Column 38, line 58, "oxabicycIo" should read --oxabicyclo--.
Column 39, line 33, "hepten oic" should read --heptenoic--.
Column 40, line 5, "20 g" should read --120 g--.
Column 40, line 58, "hepteno ic" should read --heptenoic--.
Column 41, line 39, "into ml" should read --into 200 ml--.
Column 48, line 43, "2.2.1]" should read --[2.2.1]--.
Column 52, line 67, after "gel" insert --60--.
Column 54, line 10, "3β" should read --3α--.

UNITED STATES PATENT AND TRADEMARK OFFICE
CERTIFICATE OF CORRECTION

PATENT NO. : 4,537,904

DATED : August 27, 1985

INVENTOR(S) : David L. Snitman et al.

It is certified that error appears in the above-identified patent and that said Letters Patent is hereby corrected as shown below:

Column 55, line 2, after "$C_{24}H_{32}O_4$" insert a colon (:) --.
Column 56, line 20, "fast" should read --(fast--.
Column 56, line 24, "4β" first occurrence should read --4α--.
Column 58, line 15, "armomatic" should read --aromatic--.
Column 59, line 32, "(5Z" should read --(5Z)--.
Column 59, delete line 41.
Column 59, line 42, delete "2-yl-5-heptenoic acid or".
Column 60, line 9, "4-" should read --4-(4- --.
Column 60, line 10, "2-yl" should read --2-yl]--.
Column 61, line 3, "armomatic" should read --aromatic--.
Column 61, line 5, "potion" should read --portion--.
Column 61, line 20, "accpetable" should read --acceptable--.
Column 62, line 34, "bycy" should read --bicy--.
Column 2, line 65 should read --The term "lower alkynyl" or "alkynyl" refers to an--.

Signed and Sealed this

Eleventh Day of November, 1986

Attest:

DONALD J. QUIGG

Attesting Officer    Commissioner of Patents and Trademarks